US011786593B2

(12) United States Patent
Heywood et al.

(10) Patent No.: US 11,786,593 B2
(45) Date of Patent: Oct. 17, 2023

(54) METHOD OF MONOMERISATION OF RECOMBINANT ANTIBODY MOLECULES

(71) Applicant: UCB BIOPHARMA SRL, Brussels (BE)

(72) Inventors: Sam Philip Heywood, Slough (GB); Gavin Barry Wild, Slough (GB); Razwan Hanif, Slough (GB); Christopher John Le Page, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 240 days.

(21) Appl. No.: 17/078,127

(22) Filed: Oct. 23, 2020

(65) Prior Publication Data
US 2021/0069328 A1 Mar. 11, 2021

Related U.S. Application Data

(63) Continuation of application No. 15/566,307, filed as application No. PCT/EP2016/059051 on Apr. 22, 2016, now Pat. No. 10,828,366.

(30) Foreign Application Priority Data

Apr. 22, 2015 (GB) .................................. 1506870

(51) Int. Cl.
| | | |
|---|---|---|
| A61K 39/395 | (2006.01) | |
| C07K 1/113 | (2006.01) | |
| C07K 16/28 | (2006.01) | |
| C07K 16/18 | (2006.01) | |
| C07K 5/12 | (2006.01) | |
| C07C 323/12 | (2006.01) | |
| C07C 323/25 | (2006.01) | |

(52) U.S. Cl.
CPC ...... *A61K 39/39591* (2013.01); *C07K 1/1133* (2013.01); *C07K 1/1136* (2013.01); *C07K 16/18* (2013.01); *C07K 16/2878* (2013.01); *C07C 323/12* (2013.01); *C07C 323/25* (2013.01); *C07K 5/123* (2013.01); *C07K 2317/31* (2013.01)

(58) Field of Classification Search
None
See application file for complete search history.

(56) References Cited

U.S. PATENT DOCUMENTS

| | | |
|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,453,363 A | 9/1995 | Rudolph et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,667,425 A | 9/1997 | Pineau et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,331,415 B1 | 12/2001 | Cabilly et al. |
| 10,828,366 B2* | 11/2020 | Heywood ........ A61K 39/39591 |
| 10,829,565 B2* | 11/2020 | Heywood ............ C07K 16/468 |
| 2006/0147444 A1 | 7/2006 | Huston et al. |
| 2007/0021591 A1 | 1/2007 | Movius, IV et al. |
| 2007/0191272 A1 | 8/2007 | Stemmer et al. |

(Continued)

FOREIGN PATENT DOCUMENTS

| | | |
|---|---|---|
| EP | 0392745 | 11/1994 |
| EP | 0438474 | 5/1996 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Maeda, Y. et al. "Effective renaturation of denatured and reduced immunoglobulin G in vitro without assistance of chaperone" *Protein Engineering*, 1996, pp. 95-100, vol. 9, No. 1.
Tsumoto, K. et al. "Highly efficient recovery of functional single-chain Fv fragments from inclusion bodies overexpressed in *Escherichia coli* by controlled introduction of oxidizing reagent—application to a human single-chain Fv fragment" *Journal of Immunological Methods*, Oct. 1, 1998, pp. 119-129, vol. 219, Nos. 1-2.

(Continued)

*Primary Examiner* — Phuong Huynh
(74) *Attorney, Agent, or Firm* — SALIWANCHIK, LLOYD & EISENSCHENK

(57) ABSTRACT

The present invention provides method of increasing the percentage of monomer in a composition of recombinantly expressed antibody molecules characterised in that the antibody molecule comprises at least one Fv with specificity for an antigen of interest comprising one VH and one VL wherein said VH and VL are connected directly or indirectly via one or more linkers and are stabilised by a disulfide bond therebetween, said method comprises: a) a conversion step of treating the composition with a denaturant selected from urea and/or Guanidine hydrochloride; b) wherein step a) is performed in the presence of a reducing agent or after treatment with a reducing agent.

15 Claims, 24 Drawing Sheets

Specification includes a Sequence Listing.

(56) References Cited

U.S. PATENT DOCUMENTS

| | | | | |
|---|---|---|---|---|
| 2009/0191261 | A1* | 7/2009 | Xu | A61P 35/00 424/178.1 |
| 2011/0229933 | A1 | 9/2011 | Krishnan et al. | |
| 2012/0142033 | A1 | 6/2012 | Fujiwara et al. | |
| 2012/0252098 | A1 | 10/2012 | Gagnon | |
| 2013/0066054 | A1 | 3/2013 | Humphreys et al. | |
| 2018/0100007 | A1 | 4/2018 | Heywood et al. | |
| 2018/0142039 | A1 | 5/2018 | Heywood et al. | |

FOREIGN PATENT DOCUMENTS

| | | |
|---|---|---|
| EP | 0463151 | 6/1996 |
| EP | 0546073 | 9/1997 |
| WO | WO 86/01533 | 3/1986 |
| WO | WO 89/00195 | 1/1989 |
| WO | WO 89/01476 | 2/1989 |
| WO | WO 90/02809 | 3/1990 |
| WO | WO 91/09967 | 7/1991 |
| WO | WO 91/10737 | 7/1991 |
| WO | WO 92/01047 | 1/1992 |
| WO | WO 92/02551 | 2/1992 |
| WO | WO 92/18619 | 10/1992 |
| WO | WO 92/22583 | 12/1992 |
| WO | WO 93/06231 | 4/1993 |
| WO | WO 93/11236 | 6/1993 |
| WO | WO 95/15982 | 6/1995 |
| WO | WO 95/20401 | 8/1995 |
| WO | WO 98/20734 | 5/1998 |
| WO | WO 98/25971 | 6/1998 |
| WO | WO 03/031581 | 4/2003 |
| WO | WO 03/092623 | 11/2003 |
| WO | WO 2004/051268 | 6/2004 |
| WO | WO 2004/106377 | 12/2004 |
| WO | WO 2005/003169 | 1/2005 |
| WO | WO 2005/003170 | 1/2005 |
| WO | WO 2005/003171 | 1/2005 |
| WO | WO 2005/117984 | 12/2005 |
| WO | WO 2005/117986 | 12/2005 |
| WO | WO 2006/031560 | 3/2006 |
| WO | WO 2006/047340 | 5/2006 |
| WO | WO 2007/014170 | 2/2007 |
| WO | WO 2008/038024 | 4/2008 |
| WO | WO 2009/040562 | 4/2009 |
| WO | WO 2010/019493 | 2/2010 |
| WO | WO 2010/035012 | 4/2010 |
| WO | WO 2010/151688 | 12/2010 |
| WO | WO 2011/030107 | 3/2011 |
| WO | WO 2011/036460 | 3/2011 |
| WO | WO 2011/061492 | 5/2011 |
| WO | WO 2011/086091 | 7/2011 |
| WO | WO 2011/117648 | 9/2011 |
| WO | WO 2011/117653 | 9/2011 |
| WO | WO 2013/068563 | 5/2013 |
| WO | WO 2013/068571 | 5/2013 |
| WO | WO 2013/168178 | 11/2013 |
| WO | WO 2014/019727 | 2/2014 |
| WO | WO 2014/081954 | 5/2014 |
| WO | WO 2015/134785 | 9/2015 |
| WO | WO 2015/197772 | 12/2015 |
| WO | WO 2016/169992 | 10/2016 |
| WO | WO 2016/170137 | 10/2016 |
| WO | WO 2016/170138 | 10/2016 |
| WO | WO 2018/031858 | 2/2018 |

OTHER PUBLICATIONS

Kurucz, I. et al. "A bacterially expressed single-chain Fv construct from the 2B4 T-cell receptor" *Proc. Natl. Acad. Sci.*, May 1993, pp. 3830-3834, vol. 90.

Swennen, D. et al. "Secretion of active anti-Ras single-chain Fv antibody by the yeasts *Yarrowia lipolytica* and *Kluyveromyces lactis*" *Microbiology*, 2002, pp. 41-50, vol. 148.

Tai, M-S. et al. "Targeting c-erbB-2 Expressing Tumors Using Single-Chain FV Monomers and Dimers" *Cancer Research*, Dec. 1, 1995, pp. 5983s-5989s, vol. 55.

Yang, Z. et al. "Highly Efficient Production of Soluble Proteins from Insoluble Inclusion Bodies by a Two-Step-Denaturing and Refolding Method" *PLoS One*, Jul. 29, 2011, pp. 1-8, vol. 6, No. 7.

Written Opinion in International Application No. PCT/EP2016/059051, dated Jul. 19, 2016, pp. 1-6.

Duan, Y. et al. "A novel disulfide-stabilized single-chain variable antibody fragment against rabies virus G protein with enhanced in vivo neutralizing potency" *Molecular Immunology*, 2012, pp. 188-196, vol. 51.

Search Report for Application No. GB1506870.3, dated Feb. 1, 2016, pp. 1-6.

Adair, J. R. et al. "Therapeutic Antibodies" *Drug Design Reviews*, 2005, pp. 1-11.

Ames, R. S. et al. "Conversion of murine Fabs isolated from a combinatorial phage display library to full length immunoglobulins" *Journal of Immunological Methods*, 1995, pp. 177-186, vol. 184.

Babcook, J. S. et al. "A novel strategy for generating monoclonal antibodies from single, isolated lymphocytes producing antibodies of defined specificities" *Proc. Natl. Acad. Sci. USA*, Jul. 1996, pp. 7843-7848, vol. 93.

Bird, R. E. et al. "Single-Chain Antigen-Binding Proteins" *Science*, Oct. 21, 1988, pp. 423-426, vol. 242.

Brinkmann, U. et al. "A recombinant immunotoxin containing a disulfide-stabilized Fv fragment" *Proc. Natl. Acad. Sci. USA*, Aug. 1993, pp. 7538-7542, vol. 90.

Brinkmann, U. et al. "Phage display of disulfide-stabilized Fv fragments" *Journal of Immunological Methods*, 1995, pp. 41-50, vol. 182.

Burton, D. R. et al. "Human Antibodies from Combinatorial Libraries" *Advances in Immunology*, 1994, pp. 191-280, vol. 57.

Chothia, C. et al. "Canonical Structures for the Hypervariable Regions of Immunoglobulins" *J. Mol. Biol.*, 1987, pp. 901-917, vol. 196.

Dubowchik, G. M. et al. "Receptor-mediated and enzyme-dependent targeting of cytotoxic anticancer drugs" *Pharmacology & Therapeutics*, 1999, pp. 67-123, vol. 83.

Glockshuber, R. et al. "A Comparison of Strategies To Stabilize Immunoglobulin $F_v$-Fragments" *Biochemistry*, 1990, pp. 1362-1367, vol. 29, No. 6.

Harris, R. J. "Processing of C-terminal lysine and arginine residues of proteins isolated from mammalian cell culture" *Journal of Chromatography A*, 1995, pp. 129-134, vol. 705.

Hellstrom, K. E. et al. "Antibodies for Drug Delivery" *Controlled Drug Delivery, 2nd Ed.*, 1987, pp. 623-653.

Holliger, P. et al. "Engineered antibody fragments and the rise of single domains" *Nature Biotechnology*, Sep. 2005, pp. 1126-1136, vol. 23, No. 9.

Jung, S.-H. et al. "Design of Interchain Disulfide Bonds in the Framework Region of the Fv Fragment of the Monoclonal Antibody B3" *Proteins: Structure, Function, and Genetics*, 1994, pp. 35-47, vol. 19.

Kettleborough, C. A. et al. "Isolation of tumor cell-specific single-chain Fv from immunized mice using phage-antibody libraries and the re-construction of whole antibodies from these antibody fragments" *Eur. J. Immunol.*, 1994, pp. 952-958, vol. 24.

Kohler, G. et al. "Continuous cultures of fused cells secreting antibody of predefined specificity" *Nature*, Aug. 7, 1975, pp. 495-497, vol. 256.

Kozbor, D. et al. "The production of monoclonal antibodies from human lymphocytes" *Immunology Today*, 1983, pp. 72-79, vol. 4, No. 3.

Luo, D. et al. "Vl-Linker-Vh Orientation-Dependent Expression of Single Chain Fv Containing an Engineered Disulfide-Stabilized Bond in the Framework Regions" *J. Biochem.*, 1995, pp. 825-831, vol. 118.

Mountain, A. et al. "Engineering Antibodies for Therapy" *Biotechnology and Genetic Engineering Reviews*, 1992, pp. 1-143, vol. 10. No. 1.

Orlandi, R. et al. "Cloning immunoglobulin variable domains for expression by the polymerase chain reaction" *Proc. Natl. Acad. Sci. USA.*, May 1989, pp. 3833-3837, vol. 86.

(56) References Cited

OTHER PUBLICATIONS

Persic, L. et al. "An integrated vector system for the eukaryotic expression of antibodies or their fragments after selection from phage display libraries" *Gene*, 1997, pp. 9-18, vol. 187.

Rajagopal, V. et al. "A form of anti-Tac(Fv) which is both single-chain and disulfide stabilized: comparison with its single-chain and disulfide-stabilized homologs" *Protein Engineering*, 1997, pp. 1453-1459, vol. 10, No. 12.

Reiter, Y. et al. "Stabilization of the Fv Fragments in Recombinant Immunotoxins by Disulfide Bonds Engineered into Conserved Framework Regions" *Biochemistry*, 1994, pp. 5451-5459, vol. 33.

Reiter, Y. et al. "Improved Binding and Antitumor Activity of a Recombinant Anti-erbB2 Immunotoxin by Disulfide Stabilization of the Fv Fragment" *The Journal of Biological Chemistry*, Jul. 15, 1994, pp. 18327-18331, vol. 269, No. 28.

Riechmann, L. et al. "Reshaping human antibodies for therapy" *Nature*, Mar. 24, 1988, pp. 1-6, vol. 332.

Thorpe, P. E. et al. "The Preparation and Cytotoxic Properties of Antibody-Toxin Conjugates" *Immunological Rev.*, 1982, pp. 119-158, vol. 62.

Verma, R. et al. "Antibody engineering: Comparison of bacterial, yeast, insect and mammalian expression systems" *Journal of Immunological Methods*, 1998, pp. 165-181, vol. 216.

Ward, E. S. et al. "Binding activities of a repertoire of single immunoglobulin variable domains secreted from *Escherichia coli*" *Nature*, Oct. 12, 1989, pp. 544-546, vol. 341.

Wells, J. A. et al. "Cassette mutagenesis: an efficient method for generation of multiple mutations at defined sites" *Gene*, 1985, pp. 315-323, vol. 34.

Young, N. M. et al. "Thermal stabilization of a single-chain Fv antibody fragment by introduction of a disulphide bond" *FEBS Letters*, 1995, pp. 135-139, vol. 377.

Zhu, Z. et al. "Remodeling domain interfaces to enhance heterodimer formation" *Protein Science*, 1997, pp. 781-788, vol. 6.

Stancovski, I. et al. "Mechanistic aspects of the opposing effects of monoclonal antibodies to the ERBB2 receptor on tumor growth" *Proc. Natl. Acad. Sci. USA*, Oct. 1991, pp. 8691-8695, vol. 88.

Golay, J. et al. "Mechanism of action of therapeutic monoclonal antibodies: Promises and pitfalls of in vitro and in vivo assays" *Archives of Biochemistry and Biophysics*, 2012, pp. 146-153, vol. 526.

Yu, L. et al. "Interaction between Bevacizumab and Murine VEGF-A: A Reassessment" *IOVS*, Feb. 2008, pp. 522-527, vol. 49, No. 2.

\* cited by examiner

FIGURE 9
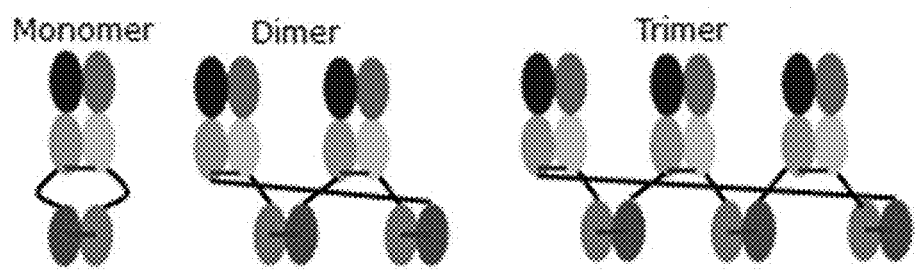
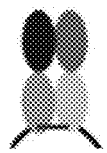
Fab = Heavy and Light Chain of Fab with a disulfide bond between the heavy and light chain and linkers joined to C-terminus of the constant region of the heavy chain and light chain to join to the dsFv
dsFv = disulfide stabilised Fv and linkers to join to the Fab

Figure 10

(a) Light chain variable region of antibody A26 specific to OX40 (SEQ ID NO:7)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKR (b) Heavy chain variable region of antibody A26 specific to OX40 (SEQ ID NO:8)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS (c)
CDRH1:    NYGIH (SEQ ID NO:1)
CDRH2:    SISPSGGLTYYRDSVKG (SEQ ID NO:2)
CDRH3:    GGEGIFDY (SEQ ID NO:3)
CDRL1:    RATQSIYNALA (SEQ ID NO:4)
CDRL2:    NANTLHT (SEQ ID NO:5)
CDRL3:    QQYYDYPLT (SEQ ID NO:6)

(d) Light chain of anti-OX40 antibody Fab component (SEQ ID NO:9)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC (e) Heavy chain of anti-OX40 antibody Fab component (SEQ ID NO:10)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSC

Figure 11

(a) Heavy chain of anti-albumin Fv component (SEQ ID NO:11)
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSS (b) Light chain of anti-albumin Fv component (SEQ ID NO:12)
DIQMTQSPSSVSASVGDRVTITCQSSPSVWSNFLSWYQQKPGKAPKLLIYEASKLTSGVP
SRFSGSGSGTDFTLTISSLQPEDFATYYCGGGYSSISDTTFGCGTKVEIKRT (c) Linker 1 (SEQ ID NO:13)
SGGGGSGGGGTGGGGS (d) Linker 2 (SEQ ID NO:14)
GGGGSGGGGSGGGGS (e) A26 Fab Heavy-(G4S,G4T,G4S)-645dsFv(gH5) (SEQ ID NO:15)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCSGGGGSGGGGTGGGGS
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSS (f) A26 Fab Light-(3xG4S)-645dsFv(gL4) (SEQ ID NO:16)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGECGGGGSGGGGSGGGGSDIQMTQSP
SSVSASVGDRVTITCQSSPSVWSNFLSWYQQKPGKAPKLLIYEASKLTSGVPSRFSGSGS
GTDFTLTISSLQPEDFATYYCGGGYSSISDTTFGCGTKVEIKRT

Figure 12

(a)    645gH1 heavy chain variable domain (SEQ ID NO:17)
EVQLLESGGGLVQPGGSLRLSCAVSGIDLSNYAINWVRQAPGKCLEWIGIIWASGTTFYA
TWAKGRFTISRDSTTVYLQMNSLRAEDTAVYYCARTVPGYSTAPYFDLWGQGTLVTVS
S (b)    645gL1 light chain variable domain (SEQ ID NO:18)
DIVMTQSPSSVSASVGDRVTITCQSSPSVWSNFLSWYQQKPGKAPKLLIYEASKLTSGVP
SRFKGSGSGTDFTLTISSLQPEDFATYYCGGGYSSISDTTFGCGTKVEIK (c)    A26 Fab Heavy-( 3xG4S)-645dsFv(gH1) (SEQ ID NO:19)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCSGGGGSGGGGSGGGGS
EVQLLESGGGLVQPGGSLRLSCAVSGIDLSNYAINWVRQAPGKCLEWIGIIWASGTTFYA
TWAKGRFTISRDSTTVYLQMNSLRAEDTAVYYCARTVPGYSTAPYFDLWGQGTLVTVS
S (d)    A26 Fab Light-(3xG4S)-645dsFv(gL1) (SEQ ID NO:20)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGECSGGGGSGGGGSGGGGSDIVMTQS
PSSVSASVGDRVTITCQSSPSVWSNFLSWYQQKPGKAPKLLIYEASKLTSGVPSRFKGSG
SGTDFTLTISSLQPEDFATYYCGGGYSSISDTTFGCGTKVEIK

Figure 13 a) DNA encoding Heavy chain A26-645(gH5) including *E.coli* OmpA leader (SEQ ID NO:21)

<u>ATGAAGAAGACTGCTATAGCGATCGCAGTGGCGCTAGCTGGTTTCGCCACCGTGGC
GCAAGCT</u>GAAGTTCAGCTGGTCGAGTCTGGAGGCGGGCTTGTCCAGCCTGGAGGGA
GCCTGCGTCTCTCTTGTGCAGCAAGCGGTTTCACGTTCACCAACTACGGTATCCACT
GGATTCGTCAGGCACCAGGTAAAGGTCTGGAATGGGTAGCCTCTATCTCTCCGTCTG
GTGGTCTGACGTACTACCGTGACTCTGTCAAAGGTCGTTTCACCATCTCTCGTGATG
ACGCGAAAAACTCTCCGTACCTGCAAATGAACTCTCTGCGTGCAGAAGATACCGCA
GTGTACTACTGCGCTACTGGTGGTGAAGGTATCTTCGACTACTGGGGTCAGGGTACC
CTGGTAACTGTCTCGAGCGCTTCTACAAAGGGCCCAAGCGTTTTCCCACTGGCTCCG
TCCTCTAAATCCACCTCTGGTGGTACGGCTGCACTGGGTTGCCTGGTGAAAGACTAC
TTCCCAGAACCAGTTACCGTGTCTTGGAACTCTGGTGCACTGACCTCTGGTGTTCAC
ACCTTTCCAGCAGTTCTCCAGTCTTCTGGTCTGTACTCCCTGTCTAGCGTGGTTACCG
TTCCGTCTTCTTCTCTGGGTACTCAGACCTACATCTGCAACGTCAACCACAAACCGTC
CAACACCAAGGTCGACAAAAAGTCGAGCCGAAATCCTGTAGTGGAGGTGGGGGCT
CAGGTGGAGGCGGGACCGGTGGAGGTGGCAGCGAGGTTCAACTGCTTGAGTCTGGA
GGAGGCCTAGTCCAGCCTGGAGGGAGCCTGCGTCTCTCTTGTGCAGTAAGCGGCATC
GACCTGAGCAATTACGCCATCAACTGGGTGAGACAAGCTCCGGGGAAGTGTTTAGA
ATGGATCGGTATAATATGGGCCAGTGGGACGACCTTTTATGCTACATGGGCGAAAG
GAAGGTTTACAATTAGCCGGGACAATAGCAAAAACACCGTGTATCTCCAAATGAAC
TCCTTGCGAGCAGAGGACACGGCGGTGTACTATTGTGCTCGCACTGTCCCAGGTTAT
AGCACTGCACCCTACTTCGATCTGTGGGGACAAGGGACCCTGGTGACTGTTTCAAGT
TAA b) DNA encoding Heavy chain A26-645(gH5) (SEQ ID NO:22)

GAAGTTCAGCTGGTCGAGTCTGGAGGCGGGCTTGTCCAGCCTGGAGGGAGCCTGCG
TCTCTCTTGTGCAGCAAGCGGTTTCACGTTCACCAACTACGGTATCCACTGGATTCGT
CAGGCACCAGGTAAAGGTCTGGAATGGGTAGCCTCTATCTCTCCGTCTGGTGGTCTG
ACGTACTACCGTGACTCTGTCAAAGGTCGTTTCACCATCTCTCGTGATGACGCGAAA
AACTCTCCGTACCTGCAAATGAACTCTCTGCGTGCAGAAGATACCGCAGTGTACTAC
TGCGCTACTGGTGGTGAAGGTATCTTCGACTACTGGGGTCAGGGTACCCTGGTAACT
GTCTCGAGCGCTTCTACAAAGGGCCCAAGCGTTTTCCCACTGGCTCCGTCCTCTAAA
TCCACCTCTGGTGGTACGGCTGCACTGGGTTGCCTGGTGAAAGACTACTTCCCAGAA
CCAGTTACCGTGTCTTGGAACTCTGGTGCACTGACCTCTGGTGTTCACACCTTTCCAG
CAGTTCTCCAGTCTTCTGGTCTGTACTCCCTGTCTAGCGTGGTTACCGTTCCGTCTTCT
TCTCTGGGTACTCAGACCTACATCTGCAACGTCAACCACAAACCGTCCAACACCAAG
GTCGACAAAAAGTCGAGCCGAAATCCTGTAGTGGAGGTGGGGGCTCAGGTGGAGG
CGGGACCGGTGGAGGTGGCAGCGAGGTTCAACTGCTTGAGTCTGGAGGAGGCCTAG
TCCAGCCTGGAGGGAGCCTGCGTCTCTCTTGTGCAGTAAGCGGCATCGACCTGAGCA
ATTACGCCATCAACTGGGTGAGACAAGCTCCGGGGAAGTGTTTAGAATGGATCGGT

Figure 13 (continued)

ATAATATGGGCCAGTGGGACGACCTTTTATGCTACATGGGCGAAAGGAAGGTTTAC
AATTAGCCGGGACAATAGCAAAAACACCGTGTATCTCCAAATGAACTCCTTGCGAG
CAGAGGACACGGCGGTGTACTATTGTGCTCGCACTGTCCCAGGTTATAGCACTGCAC
CCTACTTCGATCTGTGGGGACAAGGGACCCTGGTGACTGTTTCAAGTTAA

Figure 14
a) DNA encoding Light chain A26-645(gL4) including E.coli OmpA leader (SEQ ID NO:23)
ATGAAAAAGACAGCTATCGCAATTGCAGTGGCGTTGGCTGGTTTCGCGACCGTTGCG
CAAGCTGATATCCAGATGACCCAGAGCCCAAGCAGTCTCTCCGCCAGCGTAGGCGA
TCGTGTGACTATTACCTGTCGTGCAACCCAGAGCATCTACAACGCTCTGGCTTGGTA
TCAGCAGAAACCGGGTAAAGCGCCAAAACTCCTGATCTACAACGCGAACACTCTGC
ATACTGGTGTTCCGTCTCGTTTCTCTGCGTCTGGTTCTGGTACGGACTCTACTCTGAC
CATCTCCTCTCCAGCCGGAAGATTTCGCGACCTACTACTGCCAGCAGTACTACGA
TTACCCACTGACGTTTGGTGGTGGTACCAAAGTTGAGATCAAACGTACGGTTGCAGC
TCCATCCGTCTTCATCTTTCCACCGTCTGACGAACAGCTCAAATCTGGTACTGCTTCT
GTCGTTTGCCTCCTGAACAACTTCTATCCGCGTGAAGCGAAAGTCCAGTGGAAAGTC
GACAACGCACTCCAGTCTGGTAACTCTCAGGAATCTGTGACCGAACAGGACTCCAA
AGACTCCACCTACTCTCTGTCTAGCACCCTGACTCTGTCCAAAGCAGACTACGAGAA
ACACAAAGTGTACGCTTGCGAAGTTACCCATCAGGGTCTGAGCTCTCCGGTTACCAA
ATCCTTTAATAGAGGGGAGTGTGGTGGCGGTGGCAGTGGTGGTGGAGGTTCCGGAG
GTGGCGGTTCAGACATACAAATGACCCAGAGTCCTTCATCGGTATCCGCGTCCGTTG
GCGATAGGGTGACTATTACATGTCAAAGCTCCTAGCGTCTGGAGCAATTTTCTAT
CCTGGTATCAACAGAAACCGGGGAAGGCTCCAAAACTTCTGATTTATGAAGCCTCG
AAACTCACCAGTGGAGTTCCGTCAAGATTCAGTGGCTCTGGATCAGGGACAGACTTC
ACGTTGACAATCAGTTCGCTGCAACCAGAGGACTTTGCGACCTACTATTGTGGTGGA
GGTTACAGTAGCATAAGTGATACGACATTTGGGTGCGGTACTAAGGTGGAAATCAA
ACGTACCTAA b) DNA encoding Light chain A26-645(gL4) (SEQ ID NO:24)
GATATCCAGATGACCCAGAGCCCAAGCAGTCTCTCCGCCAGCGTAGGCGATCGTGT
GACTATTACCTGTCGTGCAACCCAGAGCATCTACAACGCTCTGGCTTGGTATCAGCA
GAAACCGGGTAAAGCGCCAAAACTCCTGATCTACAACGCGAACACTCTGCATACTG
GTGTTCCGTCTCGTTTCTCTGCGTCTGGTTCTGGTACGGACTCTACTCTGACCATCTC
CTCTCCAGCCGGAAGATTTCGCGACCTACTACTGCCAGCAGTACTACGATTACCC
ACTGACGTTTGGTGGTGGTACCAAAGTTGAGATCAAACGTACGGTTGCAGCTCCATC
CGTCTTCATCTTTCCACCGTCTGACGAACAGCTCAAATCTGGTACTGCTTCTGTCGTT
TGCCTCCTGAACAACTTCTATCCGCGTGAAGCGAAAGTCCAGTGGAAAGTCGACAA
CGCACTCCAGTCTGGTAACTCTCAGGAATCTGTGACCGAACAGGACTCCAAAGACTC
CACCTACTCTCTGTCTAGCACCCTGACTCTGTCCAAAGCAGACTACGAGAAACACAA
AGTGTACGCTTGCGAAGTTACCCATCAGGGTCTGAGCTCTCCGGTTACCAAATCCTT
TAATAGAGGGGAGTGTGGTGGCGGTGGCAGTGGTGGTGGAGGTTCCGGAGGTGGCG
GTTCAGACATACAAATGACCCAGAGTCCTTCATCGGTATCCGCGTCCGTTGGCGATA
GGGTGACTATTACATGTCAAAGCTCCTAGCGTCTGGAGCAATTTTCTATCCTGGT
ATCAACAGAAACCGGGGAAGGCTCCAAAACTTCTGATTTATGAAGCCTCGAAACTC
ACCAGTGGAGTTCCGTCAAGATTCAGTGGCTCTGGATCAGGGACAGACTTCACGTTG Figure 14 (continued)

ACAATCAGTTCGCTGCAACCAGAGGACTTTGCGACCTACTATTGTGGTGGAGGTTAC
AGTAGCATAAGTGATACGACATTTGGGTGCGGTACTAAGGTGGAAATCAAACGTAC
CTAA

Figure 15 a) DNA encoding Heavy chain A26-645(gH5) including B72.3 leader sequence (SEQ ID NO:25)
<u>ATGGAATGGTCCTGGGTCTTCCTGTTTTTCCTTTCTGTCACAACCGGGGTGCACAGCG</u>
AGGTGCAGCTCGTCGAGTCTGGAGGCGGGCTTGTCCAGCCTGGAGGGAGCCTGCGT
CTCTCTTGTGCAGCAAGCGGTTTCACGTTCACCAACTACGGTATCCACTGGATTCGTC
AGGCACCAGGTAAAGGTCTGGAATGGGTAGCCTCTATCTCTCCGTCTGGTGGTCTGA
CGTACTACCGTGACTCTGTCAAAGGTCGTTTCACCATCTCTCGTGATGACGCGAAAA
ACTCTCCGTACCTGCAGATGAACTCTCTGCGTGCAGAAGATACCGCAGTGTACTACT
GCGCTACTGGTGGTGAAGGTATCTTCGACTACTGGGGTCAGGGTACCCTGGTAACTG
TCTCAAGCGCTTCTACAAAGGGCCCATCGGTCTTCCCCCTGGCACCCTCCTCCAAGA
GCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACACCTTCCC
GGCTGTCCTACAGTCCTCTGGACTCTACTCCCTCAGCAGCGTGGTGACCGTGCCCTC
CAGCAGCTTGGGCACCCAGACCTACATCTGCAACGTGAATCACAAGCCCAGCAACA
CCAAGGTGGACAAGAAAGTTGAGCCCAAATCTTGTTCCGGAGGTGGCGGTTCCGGA
GGTGGCGGTACCGGTGGCGGTGGATCCGAAGTCCAGCTGCTTGAATCCGGAGGCGG
ACTCGTGCAGCCCGGAGGCAGTCTTCGCTTGTCCTGCGCTGTATCTGGAATCGACCT
GAGCAATTACGCCATCAACTGGGTGAGACAGGCACCTGGGAAATGCCTCGAATGGA
TCGGCATTATATGGGCTAGTGGGACGACCTTTTATGCTACATGGGCGAAGGGTAGAT
TCACAATCTCACGGGATAATAGTAAGAACACAGTGTACCTGCAGATGAACTCCCTGC
GAGCAGAGGATACCGCCGTTTACTATTGTGCTCGCACTGTCCCAGGTTATAGCACTG
CACCCTACTTTGATCTGTGGGGGCAGGGCACTCTGGTCACCGTCTCGAGTTGA b) DNA encoding Heavy chain A26-645(gH5) (SEQ ID NO:26)
GAGGTGCAGCTCGTCGAGTCTGGAGGCGGGCTTGTCCAGCCTGGAGGGAGCCTGCG
TCTCTCTTGTGCAGCAAGCGGTTTCACGTTCACCAACTACGGTATCCACTGGATTCGT
CAGGCACCAGGTAAAGGTCTGGAATGGGTAGCCTCTATCTCTCCGTCTGGTGGTCTG
ACGTACTACCGTGACTCTGTCAAAGGTCGTTTCACCATCTCTCGTGATGACGCGAAA
AACTCTCCGTACCTGCAGATGAACTCTCTGCGTGCAGAAGATACCGCAGTGTACTAC
TGCGCTACTGGTGGTGAAGGTATCTTCGACTACTGGGGTCAGGGTACCCTGGTAACT
GTCTCAAGCGCTTCTACAAAGGGCCCATCGGTCTTCCCCCTGGCACCCTCCTCCAAG
AGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCC
CGGCTGTCCTACAGTCCTCTGGACTCTACTCCCTCAGCAGCGTGGTGACCGTGCCCT
CCAGCAGCTTGGGCACCCAGACCTACATCTGCAACGTGAATCACAAGCCCAGCAAC
ACCAAGGTGGACAAGAAAGTTGAGCCCAAATCTTGTTCCGGAGGTGGCGGTTCCGG
AGGTGGCGGTACCGGTGGCGGTGGATCCGAAGTCCAGCTGCTTGAATCCGGAGGCG
GACTCGTGCAGCCCGGAGGCAGTCTTCGCTTGTCCTGCGCTGTATCTGGAATCGACC
TGAGCAATTACGCCATCAACTGGGTGAGACAGGCACCTGGGAAATGCCTCGAATGG
ATCGGCATTATATGGGCTAGTGGGACGACCTTTTATGCTACATGGGCGAAGGGTAGA Figure 15 (continued)

TTCACAATCTCACGGGATAATAGTAAGAACACAGTGTACCTGCAGATGAACTCCCTG
CGAGCAGAGGATACCGCCGTTTACTATTGTGCTCGCACTGTCCCAGGTTATAGCACT
GCACCCTACTTTGATCTGTGGGGGCAGGGCACTCTGGTCACCGTCTCGAGTTGA

Figure 16 a) DNA encoding Light chain A26-645(gL4) including B72.3 leader sequence (SEQ ID NO:27)
<u>ATGTCAGTTCCCACACAGGTGCTGGGCCTGCTTCTGTTGTGGCTCACCGATGCTAGG
TGT</u>GATATCCAGATGACCCAGAGTCCAAGCAGTCTCTCCGCCAGCGTAGGCGATCGT
GTGACTATTACCTGTCGTGCAACCCAGAGCATCTACAACGCTCTGGCTTGGTATCAG
CAGAAACCGGGTAAAGCGCCAAAACTCCTGATCTACAACGCGAACACTCTGCATAC
CGGTGTTCCGTCTCGTTTCTCTGCGTCTGGTTCTGGTACGGACTCTACTCTGACCATC
TCCTCTCTGCAGCCGGAAGATTTCGCGACCTACTACTGCCAGCAGTACTACGATTAC
CCACTGACGTTTGGTGGTGGTACCAAAGTTGAGATCAAACGTACGGTGGCTGCACCA
TCTGTCTTCATCTTCCCCCATCTGATGAGCAGTTGAAGTCTGGCACTGCCTCTGTTG
TGTGCCTGCTGAATAACTTCTACCCTAGAGAGGCCAAAGTCCAGTGGAAGGTGGAT
AACGCCCTTCAATCCGGAAACTCCCAGGAGAGTGTCACTGAGCAGGACTCAAAGGA
CTCCACCTATAGCCTTAGCAGCACACTGACACTGAGCAAGGCTGACTACGAGAAAC
ACAAGGTCTACGCCTGCGAAGTGACACATCAAGGCCTGAGCTCACCCGTGACAAAG
AGCTTTAACAGGGGAGAGTGTGGTGGAGGTGGCTCTGGCGGTGGTGGCTCCGGAGG
CGGAGGAAGCGACATCCAGATGACCCAGAGCCCTTCCTCTGTAAGCGCCAGTGTCG
GAGACAGAGTGACTATTACCTGCCAAAGCTCCCCTTCAGTCTGGTCCAATTTTCTAT
CCTGGTACCAGCAAAAGCCCGGAAAGGCTCCTAAATTGCTGATCTACGAAGCAAGC
AAACTCACCAGCGGCGTGCCCAGCAGGTTCAGCGGCAGTGGGTCTGGAACTGACTT
TACCCTGACAATCTCCTCACTCCAGCCCGAGGACTTCGCCACCTATTACTGCGGTGG
AGGTTACAGTAGCATAAGTGATACGACATTTGGATGCGGCACTAAAGTGGAAATCA
AGCGTACCTGA b) DNA encoding Light chain A26-645(gL4) (SEQ ID NO:28)
GATATCCAGATGACCCAGAGTCCAAGCAGTCTCTCCGCCAGCGTAGGCGATCGTGT
GACTATTACCTGTCGTGCAACCCAGAGCATCTACAACGCTCTGGCTTGGTATCAGCA
GAAACCGGGTAAAGCGCCAAAACTCCTGATCTACAACGCGAACACTCTGCATACCG
GTGTTCCGTCTCGTTTCTCTGCGTCTGGTTCTGGTACGGACTCTACTCTGACCATCTC
CTCTCTGCAGCCGGAAGATTTCGCGACCTACTACTGCCAGCAGTACTACGATTACCC
ACTGACGTTTGGTGGTGGTACCAAAGTTGAGATCAAACGTACGGTGGCTGCACCATC
TGTCTTCATCTTCCCCCATCTGATGAGCAGTTGAAGTCTGGCACTGCCTCTGTTGTG
TGCCTGCTGAATAACTTCTACCCTAGAGAGGCCAAAGTCCAGTGGAAGGTGGATAA
CGCCCTTCAATCCGGAAACTCCCAGGAGAGTGTCACTGAGCAGGACTCAAAGGACT
CCACCTATAGCCTTAGCAGCACACTGACACTGAGCAAGGCTGACTACGAGAAACAC
AAGGTCTACGCCTGCGAAGTGACACATCAAGGCCTGAGCTCACCCGTGACAAAGAG
CTTTAACAGGGGAGAGTGTGGTGGAGGTGGCTCTGGCGGTGGTGGCTCCGGAGGCG
GAGGAAGCGACATCCAGATGACCCAGAGCCCTTCCTCTGTAAGCGCCAGTGTCGGA
GACAGAGTGACTATTACCTGCCAAAGCTCCCCTTCAGTCTGGTCCAATTTTCTATCCT
GGTACCAGCAAAAGCCCGGAAAGGCTCCTAAATTGCTGATCTACGAAGCAAGCAAA
CTCACCAGCGGCGTGCCCAGCAGGTTCAGCGGCAGTGGGTCTGGAACTGACTTTACC

Figure 16 (continued)

CTGACAATCTCCTCACTCCAGCCCGAGGACTTCGCCACCTATTACTGCGGTGGAGGT
TACAGTAGCATAAGTGATACGACATTTGGATGCGGCACTAAAGTGGAAATCAAGCG
TACCTGA

FIGURE 17
(a) Heavy chain variable domain of anti-albumin antibody (no ds) (SEQ ID NO:29)
EVQLLESGGGLVQPGGSLRLSCAVSGIDLSNYAINWVRQAPGKGLEWIGIIWASGTTFY
ATWAKGRFTISRDNSKNTVYLQMNSLRAEDTAVYYCARTVPGYSTAPYFDLWGQGTL
VTVSS
(b) Heavy chain variable domain of anti-albumin antibody (ds) (SEQ ID NO:30)
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSS
(c) Light chain variable domain of anti-albumin antibody (no ds) (SEQ ID NO:31)
DIQMTQSPSSVSASVGDRVTITCQSSPSVWSNFLSWYQQKPGKAPKLLIYEASKLTSGVP
SRFSGSGSGTDFTLTISSLQPEDFATYYCGGGYSSISDTTFGGGTKVEIKRT
(d) Light chain variable domain of anti-albumin antibody (ds) (SEQ ID NO:32)
DIQMTQSPSSVSASVGDRVTITCQSSPSVWSNFLSWYQQKPGKAPKLLIYEASKLTSGVP
SRFSGSGSGTDFTLTISSLQPEDFATYYCGGGYSSISDTTFGCGTKVEIKRT (e) Linker 1 (SEQ ID NO:33)    SGGGGSGGGGTGGGGS
(f) Linker 2 (SEQ ID NO:34)    GGGGSGGGGSGGGGS 645 gH5gL4 specific to albumin (SEQ ID NO: 35)
GAGGTTCAGCTGCTGGAGTCTGGAGGCGGGCTTGTCCAGCCTGGAGGGAGCCTGCG
TCTCTCTTGTGCAGTAAGCGGCATCGACCTGTCCAACTACGCGATTAACTGGGTACG
TCAGGCACCGGGTAAAGGTCTGGAATGGATCGGCATCATCTGGGCCTCTGGTACGA
CCTTCTACGCTACTTGGGCCAAAGGTCGTTTCACCATCTCCCGTGACAACTCTAAAA
ACACCGTGTACCTGCAGATGAACTCTCTGCGTGCGGAAGACACTGCGGTTTACTATT
GCGCGCGTACCGTTCCGGGCTATTCTACTGCACCGTACTTCGACCTGTGGGGTCAGG
GTACTCTGGTTACCGTCTCGAGTGGAGGTGGCGGTTCTGGCGGTGGCGGTTCCGGTG
GCGGTGGATCGGGAGGTGGCGGTTCTGATATCCAGATGACCCAGAGTCCAAGCAGT
GTTTCCGCCAGCGTAGGCGATCGTGTGACTATTACCTGTCAGTCCTCTCCGAGCGTTT
GGTCCAACTTCCTGAGCTGGTACCAGCAGAAACCGGGTAAAGCCCCGAAACTGCTG
ATCTACGAGGCGTCTAAACTGACCTCTGGTGTACCGTCCCGTTTCTCTGGCTCTGGCT
CTGGTACGGACTTCACTCTGACCATCTCCTCTCTGCAGCCGGAAGACTTTGCAACGT

Figure 17 (continued)

ACTACTGCGGTGGTGGTTACTCTTCCATCTCTGACACCACGTTCGGTGGAGGCACCA
AAGTTGAAATCAAACGTACGCATCACCATCACCATCACCATCACCATCAC 645 gH5gL4 specific to albumin (SEQ ID NO: 36)
EVQLLESGGGLVQPGGSLRLSCAVSGIDLSNYAINWVRQAPGKGLEWIGIIWASGTTFY
ATWAKGRFTISRDNSKNTVYLQMNSLRAEDTAVYYCARTVPGYSTAPYFDLWGQGTL
VTVSSGGGGSGGGGSGGGGSGGGGSDIQMTQSPSSVSASVGDRVTITCQSSPSVWSNFL
SWYQQKPGKAPKLLIYEASKLTSGVPSRFSGSGSGTDFTLTISSLQPEDFATYYCGGGYS
SISDTTFGGGTKVEIKRTHHHHHHHHHH 645 gH5gL4ds specific to albumin (SEQ ID NO: 37)
GAGGTTCAGCTGCTGGAGTCTGGAGGCGGGCTTGTCCAGCCTGGAGGGAGCCTGCG
TCTCTCTTGTGCAGTAAGCGGCATCGACCTGTCCAACTACGCGATTAACTGGGTACG
TCAGGCACCGGGTAAATGCCTGGAATGGATCGGCATCATCTGGGCCTCTGGTACGAC
CTTCTACGCTACTTGGGCCAAAGGTCGTTTCACCATCTCCCGTGACAACTCTAAAAA
CACCGTGTACCTGCAGATGAACTCTCTGCGTGCGGAAGACACTGCGGTTTACTATTG
CGCGCGTACCGTTCCGGGCTATTCTACTGCACCGTACTTCGACCTGTGGGGTCAGGG
TACTCTGGTTACCGTCTCGAGTGGAGGTGGCGGTTCTGGCGGTGGCGGTTCCGGTGG
CGGTGGATCGGGAGGTGGCGGTTCTGATATCCAGATGACCCAGAGTCCAAGCAGTG
TTTCCGCCAGCGTAGGCGATCGTGTGACTATTACCTGTCAGTCCTCTCCGAGCGTTTG
GTCCAACTTCCTGAGCTGGTACCAGCAGAAACCGGGTAAAGCCCCGAAACTGCTGA
TCTACGAGGCGTCTAAACTGACCTCTGGTGTACCGTCCCGTTTCTCTGGCTCTGGCTC
TGGTACGGACTTCACTCTGACCATCTCCTCTCTGCAGCCGGAAGACTTTGCAACGTA
CTACTGCGGTGGTGGTTACTCTTCCATCTCTGACACCACGTTCGGTTGTGGCACCAA
AGTTGAAATCAAACGTACGCATCACCATCACCATCACCATCACCATCAC 645 gH5gL4ds specific to albumin (SEQ ID NO: 38)
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSSGGGGSGGGGSGGGGSGGGGSDIQMTQSPSSVSASVGDRVTITCQSSPSVWSNFLS
WYQQKPGKAPKLLIYEASKLTSGVPSRFSGSGSGTDFTLTISSLQPEDFATYYCGGGYSSI
SDTTFGCGTKVEIKRTHHHHHHHHHH FIGURE 18
Fab-2x dsscFv formats and Fab-dsscFv-dsFv format
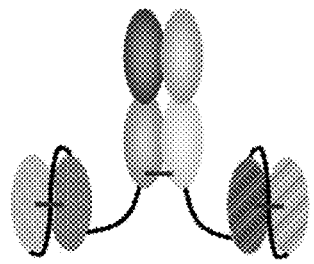
Fab#2-(HC)-dsscFv#3-(LC)-dsscFv#4
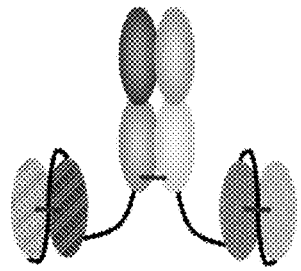
Fab#2-(LC)-dsscFv#3-(HC)-dsscFv#4
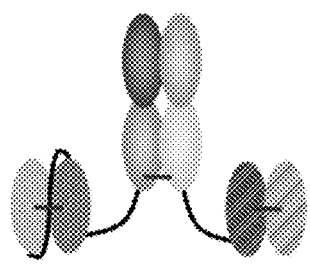
Fab-(HC)dsscFv-(LC)dsFv
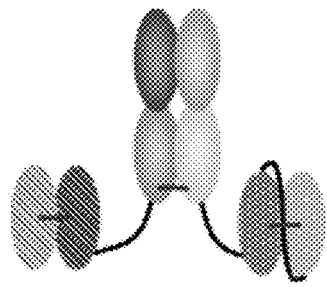
Fab-(HC)dsFv-(LC)dsscFv Fab(HC)-LHdsscFv  Fab(HC)-HLdsscFv  Fab(LC)-LHdsscFv  Fab(LC)-HLdsscFv

METHOD OF MONOMERISATION OF RECOMBINANT ANTIBODY MOLECULES

CROSS-REFERENCE TO RELATED APPLICATIONS

This application is a continuation of U.S. application Ser. No. 15/566,307, filed Oct. 13, 2017, now U.S. Pat. No. 10,828,366, which is the U.S. national stage application of International Patent Application No. PCT/EP2016/059051, filed Apr. 22, 2016.

The Sequence Listing for this application is labeled "Seq-List.txt" which was created on Oct. 12, 2017 and is 62 KB. The entire content of the sequence listing is incorporated herein by reference in its entirety.

The present disclosure relates to a method for increasing the amount of monomer in a composition of recombinantly expressed antibody molecules and compositions obtained or obtainable from the method described herein.

Therapeutic monoclonal antibodies have become a very important class of therapeutic agents. As discloses in WO2010/019493 purification and formulation of these antibody molecules represents a challenge. However, it is vitally important that only material of the highest quality is employed in therapeutic applications.

It has been well known in the art that recombinant proteins, particularly those expressed in prokaryotes, are not biologically active if they do not fold into the proper tertiary structure but form large aggregates of incorrectly folded protein, also referred to as inclusion bodies. The use of chaotropes to effectively denature and dissolve such protein aggregates is known in the art. For example, WO2007/014170 discusses many of the problems associated with the aggregation of recombinant protein compositions and discloses a buffering system comprising sodium acetate and/or sodium chloride and a chaotropic agent. The method is disclosed with respect to the deaggregation of a specific antibody format called a small modular immunopharmaceutical product which comprises a single chain binding domain and an FC region using a chaotrope in acidic buffer solution. The single chain binding domain does not contain a stabilizing disulfide bond.

Novel antibody formats often require the presence of a least one Fv region comprising a variable light domain (VL) and variable heavy domain (VH) wherein the variable domains are not in their natural state of being joined at the C-terminus to the constant light domain (CL) or constant heavy domain (CH1). In a naturally occurring whole antibody molecule the presence of the CL and CH1 domains acts to stabilize the paring of the VL and VH. Accordingly, in the absence of the CL and CH1 domains the variable domains are prone to dynamic exchange with variable domains of adjacent molecules. One way to stop this dynamic process is by the introduction of a disulfide bond between the $V_H$ and $V_L$ which locks down the v-region pairing and prevents dynamic exchange. However, the presence of the disulfide bond can also act to stabilize unwanted multimers of the antibody.

Novel antibody formats also often comprise linkers. However, the presence of the linkers may result in the formation of unwanted multimers when the variable domain in one molecule pairs with a variable domain in another molecule thereby joining the two molecules together. The presence of a disulfide bond in the Fv then acts to stabilize the multimeric species.

An example of a known bispecific antibody format is the Fab-dsFv antibodies as described in detail in WO2010/035012 and WO2011/036460. This antibody format has the propensity to form multimers which comprise two or more monomers, as shown in FIG. 9. Similar multimeric species also occur in compositions comprising disulphide bonded scFv molecules wherein the VH from one scFv pairs with the VL from a separate scFv to form disulfide stabilized Fv pair which joins two scFv molecules together resulting in a dimer of two scFvs. Further pairings of variable domains in separate molecules can create larger multimeric species.

Known methods of purification, such as chromatography, are capable of separating large multimeric species from smaller monomeric species but inevitably result in a lower overall yield of antibody. Accordingly, for bispecific antibody formats there is a great need for methods to address the problem of unwanted multimeric species in compositions of antibody.

The method of the present disclosure provides a solution to the above problem by reducing the amount of multimer in compositions comprising antibody molecules. The present disclosure is especially useful to provide compositions of monomeric monoclonal antibodies molecules suitable for human use.

Thus there is provided a method of increasing the percentage of monomer in a composition of recombinantly expressed antibody molecules characterised in that the antibody molecule comprises at least one Fv with specificity for an antigen of interest comprising one VH and one VL wherein said VH and VL are connected directly or indirectly via one or more linkers and are stabilised by a disulfide bond therebetween, said method comprises:

a) a conversion step of treating the composition with a denaturant selected from urea and/or Guanidine hydrochloride;

b) wherein step a) is performed in the presence of a reducing agent or after treatment with a reducing agent.

Employing the process described herein to recombinantly expressed antibody molecule advantageously increases the amount of monomer in the composition. Furthermore, the method herein can be easily and cost-effectively employed on a commercial scale.

The method of the present invention is capable of converting multimeric species into monomers, thereby increasing the percentage of monomer. The conversion step advantageously allows the reducing agent to reduce the disulfide bond between the VH and VL and the multimeric species to partially denature and thereby disassembling the multimers. The method also allows the VH and VL domains to form Fv pairs within single antibody molecules and the reformation of the stabilizing disulfide bond between the VH and VL resulting in monomers. Accordingly, in contrast to known uses of urea and guanidine to dissolve protein aggregates which have not correctly folded, the inventors have surprisingly shown that urea and/or guanidine and a reducing agent can be used to convert antibody multimers that have formed due to the presence of one or more linkers and a stabilizing disulfide bond to antibody monomers without fully denaturing the antibody. The method of the present invention also advantageously allows the correct disulfide bonds to be reformed to produce the desired monomers.

It has been shown that reducing agent alone does not provide more than at most 25% monomer using β-mea. However, the combination of a reducing agent and a mild denaturant has been shown to provide much higher levels of monomer, for example in the region of 80% monomer.

In one embodiment the increase in the concentration of monomer is 2, 3 or 4 fold. The method of the present invention preferably provides a recombinant antibody composition following the conversion step which comprises at least 50%, at least 60%, at least 70%, 75%, 80%, 85% or at least 90% antibody in monomeric form.

In one embodiment there is provided a composition obtained or obtainable from the process.

The invention also provides use of the composition obtained from the method disclosed herein for use in treatment.

BRIEF DESCRIPTION OF THE FIGURES

FIG. 9 shows a monomeric Fab-dsFv and multimeric versions of Fab-dsFv.

FIGS. 10 to 17 show various antibody molecule sequences and components thereof.

FIG. 18 shows example antibody formats.

DETAILED DESCRIPTION

Figure 1:
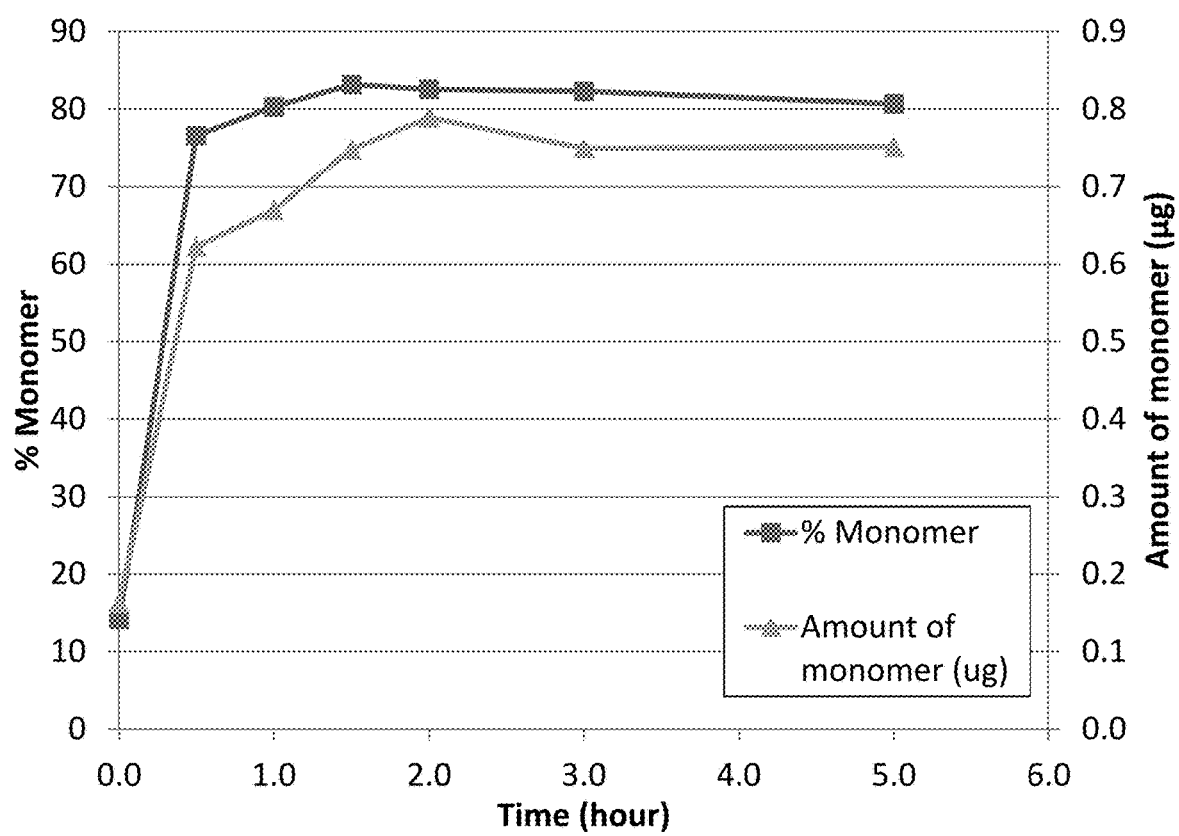
FIG. 1 shows % monomer and amount of monomer obtained after addition of β-mea to the purified antibody A26 Fab-645dsFv at room temperature, obtained by SE-UPLC analysis.

The term multimers or multimeric form as used herein refers to antibody forms consisting of the domains from two or more antibody monomers in which all of the domains are correctly folded and paired. By way of example, multimers may be formed from two or more antibody monomers wherein each VH domain is paired with a VL domain to form a complementary Fv region, such as shown for a Fab-dsFv in FIG. 9.

In one embodiment increasing the percentage of monomer as employed herein refers to obtaining a numerical value of monomeric antibody molecule that is a higher percentage of the total target protein yield compared to the monomer antibody molecule percentage obtain before the process of the present disclosure was applied. For example, the percentage monomer may be at least 30% of the initial yield of antibody molecules and after applying the present process the percentage monomer may be at least 50%, at least 60%, at least 70%, at least 75%, at least 80%, at least 85% or at least 90%. In one embodiment the absolute numerical value i.e. yield of isolated monomer is higher after performing the process of the present disclosure.

Yield or total protein as employed herein refers to the combined value of antibody molecule species in the composition. In one embodiment the value of the yield employed is the value before processing according to the present disclosure.

In one embodiment the value of the yield employed is the amount of total protein (antibody molecule species) recovered after performing the process according to the present disclosure.

The total protein (antibody molecule species) recovered after performing the process of the present disclosure will be reduced because inevitably processing results in some loses.

Target protein refers to the recombinant antibody molecule that is expressed.

Recombinant protein is protein, such as an antibody molecule expressed employing recombinant techniques.

Unless the context indicates otherwise antibody concentration as employed herein, also referred to as the feed concentration, refers to material comprising the target protein and multimers thereof the concentration of all antibody species including monomers and multimers. In one embodiment, the antibody concentration is the concentration of antibody in the composition following a step of Protein A purification to remove impurities from the composition.

The reducing agent as employed herein refers to a reducing agent capable of reducing a disulfide bond in the molecule in question, such as the antibody. The reducing agent in the presence of an antibody comprising one or more disulfide bonds has the capacity, under appropriate conditions, to reduce the disulfide bond, for example to a form —SH. In one embodiment the reducing agent itself comprises a single thiol group, two thiol groups or three or more thiol groups. Alternatively, the reducing agent does not comprise a thiol group itself.

Thiol as employed herein refers to a group comprising the entity —SH.

In one embodiment the reducing agent is selected from the group comprising: glutathione (GSH), ethylene sulfite, 2-mercaptoethanol (BME), 2-mercaptoethylamine including salts thereof such as hydrochloride (also referred to as BMEA, bMEA or B-mea, β-mea or βmea), cysteine, such as cysteine-HCl, phosphorous acid and dithiothreitol (DTT), TCEP (tris(2-carboxyethyl)phosphine), THP (tris(hydroxypropyl)phosphine).

The use of reducing agents, particularly thiol reducing agents comprising a single thiol group, is beneficial as the desired disulfide bond between the variable regions of monomers forms naturally after performing the process i.e. without the need to perform a specific oxidation step at the end of the process. Examples of thiol reducing agents comprising one thiol group include, but are not limited to, glutathione, mercaptoethanol (such as 2-mercaptoethanol), mercaptoethylamine (such as 2-mercaptoethylamine) and cysteine (such as cysteine-HCl).

In one embodiment the thiol reducing agent is mercaptoethanol (such as 2-mercaptoethanol), mercaptoethylamine (such as 2-mercaptoethylamine), and in particular 2-mercaptoethylamine (also referred to as BMEA, bMEA or B-mea, β-mea or βmea).

A further benefit of the method according to the present disclosure is that antibody molecule is not unfolded by the conditions employed. That is to say deactivation resulting from unfolding appropriately folded polypeptides/proteins is minimised and the need to refold the antibody is avoided. In one embodiment, wherein the antibody comprises multiple disulfide bonds not all disulfide bonds in the antibody are reduced. Thus in molecules such as so-called Fab-dsFv intra-chain disulfide bonds in the Fab fragment and the Fv of the antibody are not reduced by the method of the present invention. β-mea is particularly advantageous for Fab-dsFv molecules.

In one embodiment the concentration of reducing agent is in the range 1 mM to 150 mM, for example 10 to 150 mM, 50 to 150 mM, 80 to 150 mM, 90 to 140, 95 to 135 mM, such as 60, 70, 75, 80, 85, 90, 95, 100, 105, 110, 115, 120, 125, 130, 135, 140, 145 or 150 mM.

In one embodiment the concentration of the urea, guanidine or combination thereof is in the range 1 to 5 molar.

Urea as used herein refers to an organic compound also known as carbamide, with the chemical formula $CO(NH_2)_2$.

Guanidine as employed herein has the formula $HNC(NH_2)_2$ or a salt thereof. Preferably guanidine hydrochloride is used.

In one embodiment the denaturant in step a) is urea. In one embodiment the concentration of urea in the treatment according to the present disclosure is in the range 1 to 5 molar, for example 2 to 5 molar, 2.5 to 5 molar, 3 to 5 molar, 4 to 5 molar, 4.0 to 4.9 molar or 4.5 to 4.9 molar, such as 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8 or 4.9 molar, in particular 4.7 molar. In one embodiment the concentration of urea is less than 5 molar.

In one embodiment the concentration of urea is in the range 3 to 5M and the reducing agent is 2-mercaptoethylamine at a concentration in the range 10 to 150 mM. In one embodiment the concentration of urea is in the range 3 to 5M and the reducing agent is 2-mercaptoethylamine at a concentration in the range 50 to 150 mM. In one embodiment the concentration of urea is in the range 3 to 5M and the reducing agent is 2-mercaptoethylamine at a concentration in the range 80 to 150 mM. In one embodiment the concentration of urea is in the range 4 to 5M and the reducing agent is 2-mercaptoethylamine at a concentration in the range 80 to 150 mM. In one embodiment the concentration of urea is in the range 4.5 to 4.9M and the reducing agent is 2-mercaptoethylamine at a concentration in the range 95 to 135 mM. In one embodiment the concentration of urea is 4.7M and the reducing agent is 2-mercaptoethylamine at a concentration of 115 mM.

In one embodiment the denaturant in step a) is guanidine hydrochloride (also referred to as guanidine). In one embodiment the concentration of guanidine is selected from 1.0 to 2.5M, 1.0 to 2.0M, 0.5 to 1.5M, such as 1.0M.

In one embodiment the concentration of guanidine is in the range 0.5 to 1.5M and the reducing agent is 2-mercaptoethylamine at a concentration in the range 10 to 150 mM. In one embodiment the concentration of guanidine is in the range 0.5 to 1.5M and the reducing agent is 2-mercaptoethylamine at a concentration in the range 10 to 50 mM. In one embodiment the concentration of guanidine is 1.0M and the reducing agent is 2-mercaptoethylamine at a concentration of 10 mM.

In one embodiment both urea and guanidine are used together as the denaturant in step a) with specific concentrations as described above. Alternatively, either urea or guanidine is used as the denaturant in step a).

In one embodiment the reducing agent is added to the recombinant antibody molecule composition, before adding the urea, guanidine or combination thereof.

In this embodiment the step a) may be performed after treatment with the reducing agent. In this embodiment, the reducing agent may remain in the composition during treatment with the denaturant or the reducing agent is removed prior to step a). The stronger the reducing agent the more likely it is to be suited for use in a pre-treatment step and be removed prior to step a). Accordingly, in one embodiment wherein the reducing agent is selected from phosphorous acid, DDT, TCEP and THP, the reducing agent is removed prior to step a). If required, the reducing agent may be removed prior to step a) by routine techniques including diafiltration and the like.

Alternatively the reducing agent remains in the composition during treatment with the denaturant in step a) and this is particularly of benefit for reducing agents which contain a single thiol group such as the reducing agents selected from glutathione, mercaptoethanol (such as 2-mercaptoethanol), mercaptoethylamine (such as 2-mercaptoethylamine) and cysteine (such as cysteine-HCl).

In one embodiment the reducing agent is added to the recombinant antibody molecule composition, after adding the urea, guanidine or combination thereof.

In one embodiment the reducing agent is added to the recombinant antibody molecule composition, concomitant with adding the urea, guanidine or combination thereof.

In the above embodiments, wherein the reducing agent is added prior to treatment with the denaturant in step a) and remains in the composition during treatment with the denaturant in step a) or is added after adding the denaturant or is added concomitant with the denaturant, the reducing agent may be removed during or after step a) by routine techniques including diafiltration and the like.

In one embodiment, method comprises a further step of removing the urea and/or guanidine.

In one embodiment, following removal of the urea and/or guanidine, the method comprises a further step of subjecting the composition to oxidizing conditions after step a) in order to reform the one or more disulfide bonds in the antibody. This embodiment may be of benefit if a reducing agent such as phosphorous acid, DDT, TCEP or THP is used. Alternatively, the method does not comprise a step of subjecting the composition to oxidising conditions after step a). An oxidising step is not required particularly when a reducing agent comprising a single thiol group such as glutathione, mercaptoethanol (such as 2-mercaptoethanol), mercaptoethylamine (such as 2-mercaptoethylamine) and cysteine (such as cysteine-HCl) is used.

In one embodiment the temperature at which the method is performed is at ambient temperature, for example in the range 15 to 25° C., such as 18, 19, 20, 21, 22, 23, 24 or 25° C. Suitably the method is performed in the range 18 to 25° C., such as 18 to 22° C.

A temperature in the range as employed herein does not necessarily mean the composition is held at the same temperature for the duration of the process, however the composition is generally held at one or more temperatures in the stated range, during the period over which the method is performed. If and when, the temperature drifts or shifts outside the range during treatment the controller will take steps to bring the composition within the desired range.

In the method of the present invention the conversion step is suitably carried out for a period of at least 5 minutes, at least 15 minutes or at least 30 minutes. In one embodiment the period over which the antibody molecule composition is treated according to the present disclosure is in the range 1 to 70 hours, for example 2 to 60 hours, such as 3 to 50 hours, 3 to 10 hours, 4 to 6 hours, 5 to 6 hours, 4.5 to 5.5 hours in particular 4, 5, 6, 7, 8, 9, 10, 11, 12, 13, 14, 15, 16, 17, 18, 19, 20, 21, 22, 23, 24, 25 hours. In one embodiment the period is around 4 to 6 hours, such as 4 to 5 hours or 5 to 6 hours.

In one embodiment the method according to the present disclosure comprises stirring, for example where the stirring in the range 100 to 1200 rpm, such as 100, 200, 300, 400, 500, 600, 700, 800, 900, 1000, 1100 or 1200 rpm.

In one embodiment one or more steps of the process are performed at a pH in the range 3.5 to 9, for example 3.8, 4, 4.5, 5, 5.5, 6, 6.5, 7, 7.5, or 8. In one embodiment wherein an amino acid is present in the composition, the pH of the composition is adjusted to pH 7 using a pH adjusting agent, for example phosphoric acid, prior to treatment according to the present disclosure. This step of pH adjustment is particularly advantageous when lysine is added, which may be at a high pH of around pH10. In this embodiment, the use of a pH adjustment step to pH 7 improves yield of the recombinant protein. In one embodiment one or more steps of the process are performed at a pH in the range 3.5 to 9, for example 3.8, 4, 4.5, 5, 5.5, 6, 6.5, 7, 7.5, or 8.

In one embodiment the concentration of antibody molecule in the composition is in the range 1 to 5 g/L, for example 2 to 4 or 2 to 3 g/L, in particular 2.75 g/L.

In one embodiment, the antibody molecule composition does not comprise a salt at a concentration of between 0.1M to 8M.

In one embodiment robust conditions for carrying out the method of the present invention include 4.5 to 4.9M urea, 95 to 135 mM β-mea, at ambient temperature for 4 to 8 hours, such as 6 hours, in particular at an antibody concentration of about 2.75 g/L.

In one embodiment robust conditions for carrying out the method of the present invention include 4.5 to 4.9M urea, 110 to 120 mM β-mea, at ambient temperature for 4 to 8 hours, such as 6 hours, in particular at an antibody concentration of about 2.75 g/L.

In one embodiment the method is performed at temperature about 20 to 25° C. in the presence of 115 mM of β-mercaptoethylamine and 4.7M of urea, for a period of about 6 hours.

Advantageously total antibody yield may be as high as 93% wherein 76% or more thereof is monomer.

Antibody molecule as employed herein refers to an antibody (i.e. a whole antibody) or a binding fragment thereof.

The term 'antibody' relates to intact (whole) antibodies i.e. comprising the elements of two heavy chains and two light chains, molecules comprising whole antibodies or a binding fragment thereof. Binding fragment as employed herein refers to antibody like molecule comprising one, two, three or more binding sites, wherein the molecule does not contain a full length heavy chain or light chain of a "whole antibody". In one embodiment the binding fragment does not comprise a $C_H2$ and/or a $C_H3$ domain(s). Binding fragments of antibodies include single chain antibodies (i.e. a full length heavy chain and light chain); Fab, modified Fab, Fab', modified Fab', F(ab')2, Fv, Fab-Fv, Fab-dsFv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217), for example the FabFv formats disclosed in WO2009/040562 and disulphide stabilised versions thereof as disclosed in WO2010/035012. The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain.

The methods for creating and manufacturing antibody fragments are well known in the art (see for example Verma et al., 1998, Journal of Immunological Methods, 216, 165-181). Other antibody fragments for use in the present disclosure include the Fab and Fab' fragments described in WO2005/003169, WO2005/003170 and WO2005/003171.

Typical Fab' molecule comprises a heavy and a light chain pair in which the heavy chain comprises a variable region $V_H$, a constant domain $C_H1$ and a hinge region and the light chain comprises a variable region $V_L$ and a constant domain $C_L$. In one embodiment there is provided a dimer of a Fab' for example dimerisation may be through the hinge.

In one embodiment the recombinantly expressed antibody molecule is a multispecific antibody molecule, such as a bispecific or trispecific antibody. "Bi-specific molecule" as employed herein refers to a molecule with two antigen binding sites, which may bind the same or different antigens. "Tri-specific molecule" as employed herein refers to a molecule with three antigen binding sites, which may bind the same o different antigens. "Multi-specific antibody" as employed herein refers to an antibody molecule as described herein which has two or more binding domains, for example two or three binding domains. In one embodiment the domains all bind the same antigen, including binding the same epitope on the antigen or binding different epitopes on the antigen.

"Antigen binding site" as employed herein refers to a portion of the molecule, which comprises a pair of variable regions, in particular a cognate pair, that interact specifically with the target antigen. Binding site, antigen binding site, binding domain, antigen binding domain are employed interchangeably herein unless the context indicates otherwise.

Thus in one embodiment the antibody molecule comprises a binding domain. A binding domain will generally comprise 6 CDRs, three from a heavy chain and three from a light chain. In one embodiment 3 CDRs from each chain are in a framework and together with that framework they form a variable region. Thus in one embodiment an antibody molecule comprises a binding domain specific for antigen comprising a light chain variable region and a heavy chain variable region. Active fragment as employed herein is synonymous with a binding fragment.

"Specifically" as employed herein is intended to refer to an antigen binding site that only recognises the antigen to which it is specific or a binding site that has significantly higher binding affinity to the antigen to which is specific compared to affinity to antigens to which it is non-specific, for example 5, 6, 7, 8, 9, 10 times higher binding affinity. Binding affinity may be measured by standard assay, for example surface plasmon resonance, such as BIAcore.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In the method of the present invention the antibody comprises at least one Fv (VH/VL pair) with specificity for an antigen of interest wherein said VH and VL are connected directly or indirectly via one or more linkers and are stabilised by a disulfide bond therebetween.

In one embodiment the antibody or binding fragment thereof comprises a further disulfide bond, for example the where the disulfide is an interchain disulfide bond such as between the heavy and the light chain and/or wherein the in the hinge region between two heavy chains.

In one embodiment the recombinantly expressed antibody molecule comprises one or more, for example one, two, three, four, five or six disulfide bonds. In one embodiment the disulfides are naturally occurring. In one embodiment one or more disulfides are engineered to be in a particular location. In one embodiment there is at least one naturally occurring disulfide bond and at least one engineered disulfide bond. An engineered disulfide bond as employed herein refers to where one or both sulphurs in the disulfide bonds was/were introduced by recombinant genetic engineering techniques.

The position of the disulfide bond between the VH and VL is not limited. Examples of locations for disulfide bonds in the variable domains include, but are not limited to, a position selected from the group comprising:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100 b+V_L49$;

$V_H98+V_L46$ see for example Protein Science 6, 781-788 Zhu et al (1997);

$V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995)

and a position or positions corresponding thereto in variable region pair located in the molecule.

Accordingly in one embodiment a variable domain pair (VH/VL) of the present invention may be linked by a disulfide bond between two cysteine residues, one in VH and one in VL, wherein the position of the pair of cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57. In one embodiment, the disulfide bond is formed between positions VH44 and VL100.

The amino acid pairs listed above are in the positions conducive to replacement by cysteines such that disulfide bonds can be formed. Cysteines can be engineered into these desired positions by known techniques. In one embodiment therefore an engineered cysteine according to the present disclosure refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N Y, 1989; Ausbel et al., Current Protocols in Molecular Biology, Greene Publishing & Wiley-Interscience, N Y, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

Generally the VH/VL pair, wherein the VH and VL are connected directly or indirectly via one or more linkers and are stabilised by a disulfide bond therebetween, is a complementary VH/VL pair which form an antigen binding site and bind the antigen co-operatively i.e. a complementary VH/VL pair which have affinity for the same antigen and bind antigen co-operatively. Typically they will be a VH/VL pair derived from the same antibody, for example an antibody generated in vivo by a host. Bind antigen co-operatively as employed herein refers to the variable regions together bind the target antigen specifically.

In one embodiment the antibody comprises at least one Fv wherein the VH is not fused at the C-terminus to a heavy chain constant domain CH1 and the VL is not fused at the C-terminus to a light chain constant region CL (C kappa or C lambda).

The VH and VL domains are capable of forming interactions, which result in multimer formation through interactions with VH or VL domains in other antibody molecules.

In the Fv the VH and VL domains may be connected directly to each other via a linker or indirectly via linkers to one or more further molecules. The connection between the VH and VL "fixes" or defines the relationship between a given VH and VL pair such that if said VH pairs with a VL in another molecule a multimer is formed because the relationship between the original VH and VL is maintained by the presence of the connection.

In contrast, in a Fv where VH and VL domains are not connected by one or more linkers the VH and VL domains are capable of "coming-apart" (also referred to as breathing)

and when they repair if one of the variable domains is not from the original pairing (but has the same sequence as the original variable region which it replaces) then the molecule will only reform as a monomer.

The linker referred to in the present invention is preferably not a disulfide bond. Suitable linkers for use in antibodies are well known in the art. The linker may comprise one or more amino acids. In a further embodiment the linker is a peptide linker comprising 2 to 40 amino acids, such as 2 to 30, 2 to 20 or 2 to 10 amino acids. Examples of peptide linkers include those disclosed below.

In one embodiment the linker is selected from a sequence shown in sequence 39 to 90.

| Hinge linker sequences | |
|---|---|
| SEQ ID NO: | SEQUENCE |
| 39 | DKTHTCAA |
| 40 | DKTHTCPPCPA |
| 41 | DKTHTCPPCPATCPPCPA |
| 42 | DKTHTCPPCPATCPPCPATCPPCPA |
| 43 | DKTHTCPPCPAGKPTLYNSLVMSDTAGTCY |
| 44 | DKTHTCPPCPAGKPTHVNVSVVMAEVDGTCY |
| 45 | DKTHTCCVECPPCPA |
| 46 | DKTHTCPRCPEPKSCDTPPPCPRCPA |
| 47 | DKTHTCPSCPA |

| Flexible linker sequences | |
|---|---|
| SEQ ID NO: | SEQUENCE |
| 48 | SGGGGSE |
| 49 | DKTHTS |
| 50 | (S)GGGGS |
| 51 | (S)GGGGSGGGGS |
| 52 | (S)GGGGSGGGGSGGGGS |
| 53 | (S)GGGGSGGGGSGGGGSGGGGS |
| 54 | (S)GGGGSGGGGSGGGGSGGGGSGGGGS |
| 55 | AAAGSG-GASAS |
| 56 | AAAGSG-XGGGS-GASAS |
| 57 | AAAGSG-XGGGSXGGGS-GASAS |
| 58 | AAAGSG-XGGGSXGGGSXGGGS-GASAS |
| 59 | AAAGSG-XGGGSXGGGSXGGGSXGGGS-GASAS |
| 60 | AAAGSG-XS-GASAS |
| 61 | PGGNRGTTTTRRPATTTGSSPGPTQSHY |
| 62 | ATTTGSSPGPT |
| 63 | ATTTGS |
| — | GS |

| Flexible linker sequences | |
|---|---|
| SEQ ID NO: | SEQUENCE |
| 64 | EPSGPISTINSPPSKESHKSP |
| 65 | GTVAAPSVFIFPPSD |
| 66 | GGGGIAPSMVGGGGS |
| 67 | GGGGKVEGAGGGGGS |
| 68 | GGGGSMKSHDGGGGS |
| 69 | GGGGNLITIVGGGGS |
| 70 | GGGGVVPSLPGGGGS |
| 71 | GGEKSIPGGGGS |
| 72 | RPLSYRPPFPFGFPSVRP |
| 73 | YPRSIYIRRRHPSPSLTT |
| 74 | TPSHLSHILPSFGLPTFN |
| 75 | RPVSPFTFPRLSNSWLPA |
| 76 | SPAAHFPRSIPRPGPIRT |
| 77 | APGPSAPSHRSLPSRAFG |
| 78 | PRNSIHFLHPLLVAPLGA |
| 79 | MPSLSGVLQVRYLSPPDL |
| 80 | SPQYPSPLTLTLPPHPSL |
| 81 | NPSLNPPSYLHRAPSRIS |
| 82 | LPWRTSLLPSLPLRRRP |
| 83 | PPLFAKGPVGLLSRSFPP |
| 84 | VPPAPVVSLRSAHARPPY |
| 85 | LRPTPPRVRSYTCCPTP- |
| 86 | PNVAHVLPLLTVPWDNLR |
| 87 | CNPLLPLCARSPAVRTFP |
| 88 | GGGGSGGGTGGGGS |

(S) is optional in sequences 50 to 54.

Examples of rigid linkers include the peptide sequences GAPAPAAPAPA (SEQ ID NO:89), PPPP (SEQ ID NO:90) and PPP.

In one aspect of the present invention, the Fv comprises a VH domain and VL domain which are connected directly by a single linker. Suitable linkers for directly connecting the VH domain and VL domain are described above.

In one embodiment the VH and VL form a disulphide-stabilised single chain variable fragment, also referred to as a dsscFv, molecule which is a single chain variable fragment with a peptide linker between the $V_H$ and $V_L$ variable domain and an inter-domain disulphide bond between said $V_H$ and $V_L$.

In this embodiment, the dsscFv molecule may be fused to one or more further molecules, preferably a second antibody or binding fragment thereof to form bi, tri or tetra-valent antibodies. The dsscFv is fused to one or more further molecules via one or more linkers which may be positioned in the VH domain, the VL domain or both the VH and VL. For example, one or more dsscFv molecules may be fused to the C-terminus or N-terminus of one or more chains of a whole antibody or binding fragment thereof. For example, two or more dsscFv molecules may be fused together to form a Diabody, a tandem scFV (bis-dsscFv) or a Minibody.

Antibody formats which may have a propensity to multimerise through an Fv region include the scFv, Diabody, tandem scFv, tandem scFv-Fc, scFv-Fc, scFv-Fc-scFv Fab-scFv, scDiabody, scDiabody-Fc, scDiabodyCH3, IgG-scFv, scFv-IgG, two-in-one IgG, Dual V domain IgG, IgG-V and V-Ig. When a disulfide bond is employed in the Fv or scFv to stabilise these constructs then it may be beneficial to employ the present method to improve the yield of monomer obtained.

In a further aspect of the present invention, each VH and VL comprises a linker which indirectly connect the VH and VL via a second molecule. In this aspect, the VH domain and the VL domain are linked to the second molecule via separate linkers. Suitable linkers for linking each variable domain to the second molecule are described above. The second molecule provides the indirect connection between the VH and VL. Each VL and VH is linked to the second molecule in a suitable position in order to allow the VH and VL domains to bind the target antigen co-operatively. The VH domain and VL domain are not connected directly to each other by a peptide bond or a peptide linker.

In this aspect, the second molecule is preferably a second antibody or binding fragment thereof to form bi, tri or tetra-valent antibodies. In one embodiment, the VH and VL domains are linked indirectly via a whole antibody or a Fab, modified Fab, Fab', modified Fab' or F(ab')2. For example, when the second antibody is a Fab the VH domain may be fused to the C-terminus of the heavy chain constant region such as the CH1 of the second antibody and the VL single domain antibody may be fused to the C-terminus of the light chain constant region (C kappa or C lambda) of the second antibody, thereby forming a Fab-dsFv. Fab-dsFv antibodies are described in detail in WO2010/035012 and WO2011/036460 both incorporated herein by reference.

The antibody may comprise further binding domains for example as per the disulfide stabilized DVD-Ig molecule as disclosed in WO2011/117653, or the so-called (FabFv)$_2$Fc described in WO2011/030107, each incorporated herein by reference. Thus antibody as employed herein includes bi, tri or tetra-valent antibodies.

Other suitable antibody formats which may be employed in the method of the present invention are selected from a dsscFv, a Fab-2xdsscFv, a Fab-dsscFv-dsFv, a Fab-dsscFv-sdAb, a Fab-dsscFv-scFv and a Fab-dsscFv.

Other suitable antibody formats which may be employed in the method of the present invention are described in WO2011/030107 which discloses FabFvFc and (FabFv)$_2$Fc antibodies, WO2011/061492 which discloses Fab-dsFv antibodies conjugated to PEG and WO2011/086091 which discloses Fab-dsFv-dsFv each incorporated herein by reference, wherein a disulfide bond is employed in the Fv or scFv.

Other suitable antibody formats which may be employed in the method of the present invention to improve monomer yield are described in WO2015/197772, incorporated herein by reference, which discloses a multi-specific antibody molecule comprising or consisting of:

a) a polypeptide chain of formula (I):

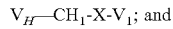
$V_H$—$CH_1$-X-$V_1$; and b) a polypeptide chain of formula (II):

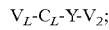
$V_L$-$C_L$-Y-$V_2$;

wherein:
$V_H$ represents a heavy chain variable domain;
$CH_1$ represents a domain of a heavy chain constant region, for example domain 1 thereof;
X represents a bond or linker;
Y represents a bond or linker;
$V_1$ represents a dsFv, a sdAb, a scFv or a dsscFv;
$V_L$ represents a light chain variable domain;
$C_L$ represents a domain from a light chain constant region, such as Ckappa;
$V_2$ represents a dsFv, a sdAb, a scFv or a dsscFv
wherein at least one of V1 and V2 is a dsscFv.

"Single chain variable fragment" or "scFv" as employed herein refers to a single chain variable fragment comprising or consisting of a heavy chain variable domain (VH) and a light chain variable domain (VL) which is stabilised by a peptide linker between the VH and VL variable domains. The VH and VL variable domains may be in any suitable orientation, for example the C-terminus of VH may be linked to the N-terminus of VL or the C-terminus of VL may be linked to the N-terminus of VH.

"Disulphide-stabilised single chain variable fragment" or "dsscFv" as employed herein refers to a single chain variable fragment which is stabilised by a peptide linker between the VH and VL variable domain and also includes an inter-domain disulphide bond between VH and VL.

"Disulphide-stabilised variable fragment" or "dsFv" as employed herein refers to a single chain variable fragment which does not include a peptide linker between the VH and VL variable domains and is instead stabilised by an inter-domain disulphide bond between VH and VL.

"Single domain antibody" or "sdAb" as employed herein refers to an antibody fragment consisting of a single monomeric variable antibody domain, such as VH or VL or VHH. Example antibody formats are shown in FIG. 18.

In one embodiment, both V1 and V2 are dsscFv and this antibody format may also be referred to herein as a Fab-2× dsscFv. The $V_H$ and $V_L$ variable domains may be in any suitable orientation, for example the C-terminus of $V_H$ may be linked to the N-terminus of $V_L$ or the C-terminus of $V_L$ may be linked to the N-terminus of $V_H$.

Figure 19:
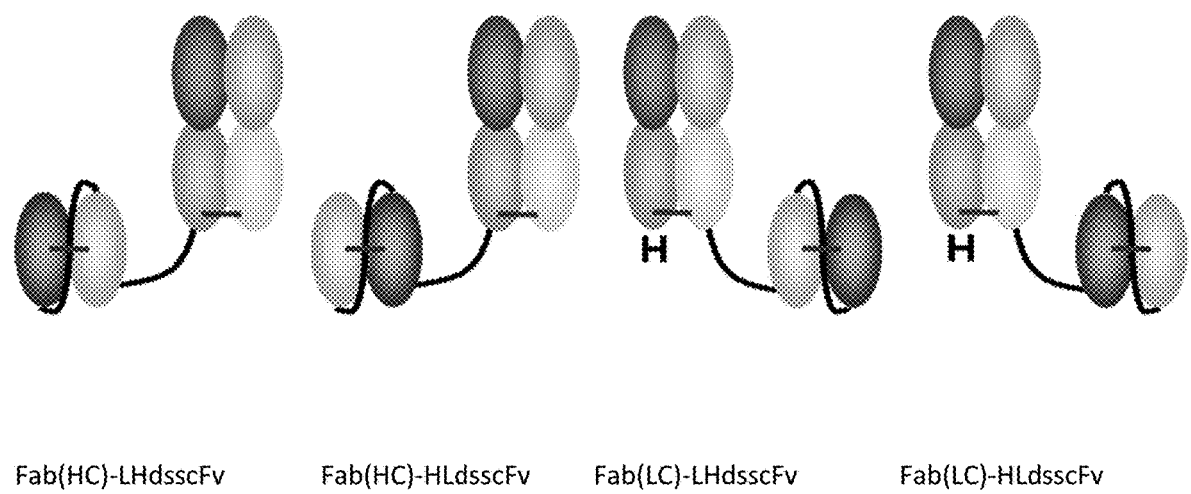
FIG. 19 shows example antibody formats.

Other suitable antibody formats which may be employed in the method of the present invention to improve monomer yield are described in Example 4 of WO2013/068571, incorporated herein by reference, which discloses a Fab-dsscFv antibody format. Example antibody formats are shown in FIG. 19.

In one embodiment the antibody does not comprise a $C_H2$ and/or $C_H3$ domain.

In one embodiment the antibody fragment is the so-called Fab-dsFv format, for example as disclosed in WO2010/035012 and WO2011/036460, each incorporated herein by reference.

In one embodiment the antibody is a disulfide stabilised Fab as disclosed in WO2011/117648. In one embodiment the antibody is not a disulfide stabilised Fab as disclosed in WO2011/117648.

In one embodiment the antibody comprises a binding domain specific to OX40.

In one embodiment the antibody comprises a binding domain specific to serum albumin.

In one embodiment the antibody comprises a binding domain specific to OX40 and a binding domain specific to serum albumin, in particular a Fab-dsFv format, such as wherein the serum albumin binding domain is the Fv portion, in particular the bispecific antibody A26Fab-645dsFv specific to OX40 and human serum albumin disclosed in WO2013/068563 incorporated herein by reference.

The present disclosure provides a bispecific antibody fusion protein which binds human OX40 and human serum albumin comprising:

a heavy chain comprising, in sequence from the N-terminal, a first heavy chain variable domain ($V_H1$), a $C_H1$ domain and a second heavy chain variable domain ($V_H2$), a light chain comprising, in sequence from the N-terminal, a first light chain variable domain ($V_L1$), a $C_L$ domain and a second light chain variable domain ($V_L2$), wherein said heavy and light chains are aligned such that $V_H1$ and $V_L1$ form a first antigen binding site and $V_H2$ and $V_L2$ form a second antigen binding site, wherein the antigen bound by the first antigen binding site is human OX40 and the antigen bound by the second antigen binding site is human serum albumin, in particular wherein the first variable domain of the heavy chain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain ($V_L1$) comprises the sequence given in SEQ ID NO:4 for CDR-L1, the sequence given in SEQ ID NO:5 for CDR-L2 and the sequence given in SEQ ID NO:6 for CDR-L3, wherein the second heavy chain variable domain ($V_H2$) has the sequence given in SEQ ID NO:11 and the second light chain variable domain ($V_L2$) has the sequence given in SEQ ID NO: 12 and the second heavy chain variable domain ($V_H2$) and second light chain variable domain ($V_L2$) are linked by a disulfide bond.

In one embodiment there is a peptide linker between the CH1 domain and the second heavy chain variable domain (VH2). In one embodiment there is a peptide linker between the CL domain and the second light chain variable domain (VL1). In one embodiment the first heavy chain variable domain (VH1) comprises the sequence given in SEQ ID NO:8. In one embodiment the first light chain variable domain (VL1) comprises the sequence given in SEQ ID NO:7. In one embodiment the heavy chain comprises or consists of the sequence given in SEQ ID NO:15. In one embodiment the light chain comprises or consists of the sequence given in SEQ ID NO:16.

In one embodiment the antibody molecule comprises a serum albumin binding domain, for example comprising one, two three heavy chain CDRs from the variable region shown in SEQ ID NO: 29 or 30, and one, two or three light chain CDRs from the variable region shown in SEQ ID NO: 31 or 32, in particular three heavy chain CDRs from the variable region shown in SEQ ID NO: 29 or 30, such as CDRH1 for CDRH1, CDRH2 for CDH2, CDRH3 for CDH3 and three light chain CDRs from the variable region shown in SEQ ID NO: 31 or 32, such as CDRL1 for CDRL1, CDRL2 for CDL2, CDRL3 for CDL3.

In one embodiment the antibody molecule comprises a heavy variable region shown in SEQ ID NO: 30. In one embodiment the antibody molecule comprises a light variable region shown in SEQ ID NO: 32. In one embodiment the antibody molecule comprises a heavy variable region shown in SEQ ID NO 30 and a light variable region shown in SEQ ID NO: 32.

In one embodiment the heavy chain comprises or consists of SEQ ID NO: 15 or 19. In one embodiment the light chain comprises or consists of SEQ ID NO: 16 or 20. In one embodiment the binding fragment antibody molecule comprises SEQ ID NO: 15 and 16, 15 and 20, 16 and 19 or 19 and 20. Thus in one embodiment there is provided a bispecific antibody fusion protein which binds human OX40 and human serum albumin, having a heavy chain comprising the sequence given in SEQ ID NO:15 and a light chain comprising the sequence given in SEQ ID NO:16.

In one embodiment the antibody molecule, such as a Fab-dsFv format is one disclosed in WO2014/019727, incorporated herein by reference.

In one embodiment the antibody molecule comprises a binding domain specific to human serum albumin, in particular with CDRs or variable regions as disclosed in WO2013/068571, incorporated herein by reference.

In one embodiment the antibody or fragment according to the present disclosure is monoclonal. Monoclonal antibodies may be prepared by any method known in the art such as the hybridoma technique (Kohler & Milstein, Nature, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies molecules employed in the methods of the present disclosure may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO92/02551, WO2004/051268 and WO2004/106377.

Humanized antibodies molecules are antibody molecules from non-human species having one or more complementarity determining regions (CDRs) from the non-human species and a framework region from a human immunoglobulin molecule which optionally comprise one or more donor residues from the non-human species (see, for example, U.S. Pat. No. 5,585,089). In one embodiment the antibody molecules which are subject to the method of the present disclosure are humanized.

The antibodies employed in the methods of the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO90/02809; WO91/10737; WO92/01047; WO92/18619; WO93/11236; WO95/15982; and WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

Transgenic mice, or other organisms, including other mammals, may also be used to generate humanized antibodies, for example using phage technology.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and/or constant region genes have been replaced by their human counterparts e.g. as described in general terms in EP0546073, U.S. Pat. Nos. 5,545,806, 5,569,825, 5,625,126, 5,633,425, 5,661,016, 5,770,429, EP 0438474 and EP0463151.

The antibody material for use in the methods of the present invention may be prepared by the use of recombinant DNA techniques involving the manipulation and re-expression of DNA encoding the antibody variable and constant region(s). Standard molecular biology techniques may be used to modify, add or delete amino acids or domains as desired. Any alterations to the variable or constant regions are still encompassed by the terms 'variable' and 'constant' regions as used herein.

The antibody starting material may be obtained from any species including, for example mouse, rat, rabbit, hamster, camel, llama, goat or human. Parts of the antibody may be obtained from more than one species, for example the antibody may be chimeric. In one example, the constant regions are from one species and the variable regions from another. The antibody starting material may also be modified. In another example, the variable region of the antibody has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibodies are well known in the art (see for example, Boss et al., U.S. Pat. No. 4,816,397; Cabilly et al., U.S. Pat. No. 6,331,415; Shrader et al., WO92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment the antibody comprises a variable domain pair forming a binding domain is a cognate pair. Cognate pair as employed herein is intended to refer to a natural pair of variable domains, that is to say isolated from a single antibody or antibody expressing cell. Variable domains may have been optimized and/or humanized. Optimised/humanized variable domains derived from a cognate pair will still be considered a cognate pair after optimization/humanization.

Thus the present disclosure extends to subjecting human, humanized or chimeric antibody molecules to the methods disclosed herein.

In one embodiment the antibody molecule specifically binds a target antigen. Specifically binds as employed herein is intended to refer to molecules having high affinity for a target antigen or ligand (to which it is specific) and which binds antigen or ligand to which it is not specific with a low or much lower affinity (or not at all). Methods of measuring affinity are known to those skilled in the art and include such assays as BIAcore™.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, PD-1, DC-SIGN, TL1A, DR3, IL-7 receptor A and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α and referred to herein as TNF or TNFα), tumor necrosis factor-β, colony stimulating factors such as G-CSF or GM-CSF, and platelet derived growth factors such as PDGF-α, and PDGF-β, WISP-1 and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment the method comprises the further step of purifying an antibody molecule to a standard suitable for administration to a human and then formulating the same.

The antibody molecules purified employing the methods described herein have a high binding affinity, in particular, nanomolar or picomolar.

Affinity may be measured using any suitable method known in the art, including BIAcore™. In one embodiment the antibody or binding fragment has a binding affinity of about 100 pM or better, for example about 50 pM or better, such as about 40 pM or better, in particular 30 pM or better. In one embodiment the antibody or binding fragment is fully human or humanised and has a binding affinity of about 100 pM or better.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

It will also be understood by one skilled in the art that the antibody may undergo a variety of posttranslational modifications. The type and extent of these modifications often depends on the host cell line used to express the molecule as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995). These post-translational changes can influence the properties of the molecule and thus impact on downstream processing.

In one embodiment the antibody composition employed in the method of the present disclosure does not comprising sodium acetate, for example at a concentration of 25 mM. In one embodiment the antibody composition employed in the method of the present disclosure does not comprise sodium chloride, for example at a concentration of 25 mM.

In one embodiment the conversion step according to the present disclosure is performed on clarified supernatant. Supernatant may be clarified by any suitable means, for example centrifugation, filtration or the like. In one embodiment the supernatant is clarified employing 0.22 micron filtration.

In one embodiment a step of protein A chromatography is carried out on the supernatant before the thermal conversion step. Protein A purification is particularly advantageous in the context of the type of antibody molecules disclosed herein (in particular those which do not comprise $C_H2$ $C_H3$ domains) because this technique allow multimer to be resolved from monomers.

The use of protein A chromatography can be used to recover a human VH3 domain-containing antibody which does not comprise an Fc region in monomeric form. An avidity effect has been observed between the binding of human VH3 domains and protein A. This finding is surprising given that it has not been described for the interaction between Fc regions and protein A and allows recovery of monomeric human VH3 domain-containing antibodies from a mixture containing monomeric and multimeric forms of the antibody.

Accordingly, the step of protein A purification may comprise a) applying a mixture comprising a human VH3 domain-containing antibody in monomeric and multimeric form to a protein A chromatography material wherein said protein A comprises domain D and/or E, under conditions that allow binding of said antibody to protein A, and b) recovering the human VH3 domain containing-antibody in monomeric form, wherein the human VH3 domain containing antibody does not contain an Fc region. Alternatively the step of protein A purification comprises a) applying a mixture comprising a human VH3 domain-containing antibody in monomeric and multimeric form to a protein A chromatography material wherein said protein A comprises domain D and/or E, b) allowing binding of said antibody to protein A, c) applying an elution buffer that selectively disrupts binding of the antibody in monomeric form, d) recovering the resulting eluate, and optionally e) applying a second elution buffer that disrupts binding of the antibody in multimeric form and recovering this second eluate, wherein the human VH3 domain-containing antibody does not contain an Fc region. In one embodiment, wherein the antibody is antibody A26Fab-645dsFv specific to OX40 and human serum albumin disclosed in WO2013/068563, the protein A purification is carried out as above wherein in step c) the elution buffer has a pH 3.5 to pH 4.2, preferably, pH 3.6 to pH 4.1, pH 3.7 to pH 4.0, preferably pH 3.8 to pH 3.9 or pH 3 to disrupt binding of the monomer and in optional step e) the elution buffer has a pH below 3.5, preferably below pH 3.4, preferably pH 2.8 to pH 3.2, preferably pH 2.9 to pH 3.1, preferably pH 3.0 that disrupts binding of the antibody in multimeric form.

Alternatively the step of protein A purification comprises a) applying a mixture comprising a human VH3 domain-containing antibody in monomeric and multimeric form to a protein A chromatography material wherein said protein A comprises domain D and/or E, b) allowing binding of the antibody in multimeric form, c) recovering the antibody in monomeric form in the flow-through, and optionally d) applying an elution buffer that selectively disrupts binding of the antibody in multimeric form, and e) recovering the eluate resulting from d); wherein the human VH3 domain-containing antibody does not contain an Fc region.

In an alternative embodiment, no protein A chromatography is carried out before the conversion step.

In one embodiment, the method comprises a further downstream processing step. In one embodiment the method comprises the further step of downstream purification, for example wherein the downstream processing comprises a chromatography step, such as hydrophobic interaction chromatography or ion exchange chromatography.

A downstream processing step means at least one step is employed subsequent performing the treatment with urea and/or guanidine and reducing agent to further purifying the antibody molecule. Examples of downstream processing includes one or more chromatography steps, for example size exclusion chromatography, ion exchange chromatography (such as anion exchange chromatography or cation exchange chromatography), hydrophobic interaction chromatography, affinity chromatography, such as protein-A chromatography (such as a MabSelect column). Techniques employed in downstream processing of polypeptides and proteins are well known to those skilled in the art.

In one embodiment the downstream processing comprises a chromatography step, in particular ion exchange chromatography. In one embodiment the method comprises an anion exchange chromatographic step followed by a cation exchange chromatographic step or vice versa. In one embodiment hydrophobic interaction chromatography is employed. In one embodiment mixed mode chromatography is employed. In one embodiment multiple chromatography steps are employed.

In one embodiment the method comprises a virus inactivation step, for example holding the composition containing the protein at a defined pH, for example low pH for a defined period.

In one embodiment the final downstream processing step is diafiltration step and buffer exchange to provide the final storage buffer and concentration for the protein.

In one embodiment the downstream processing comprises protein A (such as MabSelect column) purification, as described above before the conversion step.

In one embodiment the downstream processing further comprises a viral inactivation step, followed by ultrafiltration and buffer exchange, in turn followed by anion exchange chromatography and subsequent cation exchange chromatography and a viral filtration step.

In one embodiment the downstream processing following the conversion step comprises a viral inactivation step, followed by ultrafiltration and buffer exchange, in turn followed by anion exchange chromatography and subsequent cation exchange chromatography and a viral filtration step.

In one embodiment the downstream processing further comprises a viral inactivation step, followed by ultrafiltration and buffer exchange, in turn followed by cation exchange chromatography and subsequent anion exchange chromatography and a viral filtration step.

Other downstream processing steps include hydrophobic interaction chromatography (HIC) or mixed mode chromatography.

In one embodiment the final downstream processing step is diafiltration step and buffer exchange to provide the final storage buffer and concentration for the protein.

In one embodiment the method disclosed herein provided the further step of conjugating a purified monomeric antibody molecule to one or more effector molecules. The effector molecule may comprise a single effector molecule or two or more such molecules so linked as to form a single moiety that can be attached to the antibody molecule.

Where it is desired to obtain an antibody linked to an effector molecule, this may be prepared by standard chemical or recombinant DNA procedures in which the antibody is linked either directly or via a coupling agent to the effector molecule. Techniques for conjugating such effector molecules to an antibody are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO93/06231, WO92/22583, WO89/00195, WO89/01476 and WO03031581. Alternatively, where the effector molecule is a protein or polypeptide the linkage may be achieved using recombinant DNA procedures, for example as described in WO86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof. Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody of the disclosure and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example an antibody for use in the present invention is attached to poly(ethyleneglycol) (PEG) moieties. In one particular example the PEG molecules may be attached through any available amino acid side-chain or terminal amino acid functional group located in the antibody, for example any free amino, imino, thiol, hydroxyl or carboxyl group. Such amino acids may occur naturally in the antibody or may be engineered into the antibody using recombinant DNA methods (see for example U.S. Pat. Nos. 5,219,996; 5,667,425; WO98/25971). In one example the molecule of the present invention is a modified antibody wherein the modification is the addition to the C-terminal end of its heavy chain one or more amino acids to allow the attachment of an effector molecule. Multiple sites can be used to attach two or more PEG molecules. In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody. Each polymer molecule attached to the modified antibody may be covalently linked to the sulphur atom of a cysteine residue located in the antibody. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment the present disclosure extends to an antibody molecule obtained or obtainable from the method disclosed herein.

In one embodiment the method comprises the further step of formulating the antibody molecule obtained from the represent method including conjugated versions thereof, as a pharmaceutical formulation suitable for use in humans.

Thus the present invention also provides a process step for preparation of a pharmaceutical or diagnostic composition comprising adding and mixing the antibody of the present invention together with one or more of a pharmaceutically acceptable excipient, diluent or carrier.

The antibody molecule obtained from the method of the present disclosure may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody or composition according to the disclosure is employed in combination with a further pharmaceutically active agent, for example a corticosteroid (such as fluticasonase propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which an antibody of the present invention is administered depends on the nature of the condition to be treated, for example the extent of the disease/inflammation present and on whether the molecule is being used prophylactically or to treat an existing condition.

The frequency of dose will depend on the half-life of the antibody and the duration of its effect. If the antibody has a short half-life (e.g. 2 to 10 hours) it may be necessary to give one or more doses per day. Alternatively, if the antibody has a long half-life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody, for example if the pH of the formulation is 7 then a pI of from 8-9 or above may be appropriate. Whilst not wishing to be bound by theory it is thought that this may ultimately provide a final formulation with improved stability, for example the antibody remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active ingredient (such as the antibody) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody or binding fragment obtained from the method herein can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 mL of water so as to achieve a pH of about 4.0 to 5.0. A suspension can employ, for example, lyophilised molecule.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the molecule in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

Comprising in the context of the present specification is intended to meaning including. Where technically appropriate embodiments of the invention may be combined. Any positively recited embodiment herein may be employed as the basis of a negative disclaimer.

The invention will now be described with reference to the following examples, which are merely illustrative and should not in any way be construed as limiting the scope of the present invention.

Example 1: Preparation of Antibody Molecule Material

CHO expression and clarification of A26Fab-645dsFv The constructs which binds human OX40 and serum albumin having the light chain sequence A26 Fab Light-(3× G4S)-645dsFv(gL4) (SEQ ID NO:16) and the heavy chain sequence A26 Fab Heavy-(G4S,G4T,G4S)-645dsFv(gH5) (SEQ ID NO:15) was expressed in a stable dihydrofolate reductase (DHFR) deficient Chinese Hamster Ovary cell line (CHO DG44). This was generated by transfection using a Nucleofector (Lonza) following the manufacturer's instructions with a plasmid vector containing both the gene for DHFR as a selectable marker and the genes encoding the product. Transfected cells were selected in medium lacking hypoxanthine and thymidine, and in the presence of the DHFR inhibitor methotrexate.

The cell line was cultivated in medium containing 20 nM methotrexate throughout the inoculum stages. The cells are then cultivated in the absence of methotrexate. For the final culture step, the cells were cultivated in a 80 L stainless steel bioreactor for 14 days in medium in the absence of methotrexate. The bioreactor contents at day 14 were harvested by disc stack centrifugation, followed by multiple filtration steps to produce the clarified supernatant.

Protein-A Purification of Mammalian Expressed A26Fab-645dsFv

Clarified CHO supernatants were applied to a 9.4 ml HiScreen (2 columns in series) Mab Select chromatography resin (GE Healthcare) packed in a range of column sizes depending on the scale required. The columns were equilibrated in Delbeccos Phosphate Buffered Saline (PBS) pH7.4, or in 100 mM sodium phosphate, 150 mM NaCl pH 7.4. The column was washed with PBS the equilibration buffer after loading and the bound material was then eluted with 0.1M Sodium Citrate Buffer at pH 3.4. The collected elution peak was pH adjusted to ~pH 7 with 2M Tris/HCl pH 8.5. The pH adjusted elutions were buffer exchanged into PBS phosphate buffer at pH 7.4 using 10 kDa molecular weight cut off centrifugation concentrators or tangential flow ultrafiltration membranes.

Example 2: Effect of Only Reductant, and Combination of Reductant and Denaturant on Monomer Yield Reductant Only The feed was purified antibody as provided in Example 1, concentration 1 g/L and 15% monomer. The experiment was performed at room temperature in Eppendorfs with a feed volume of 1 mL. The reductant used was 50 mM β-mea. Before any analysis was performed the samples were buffer exchanged with PBS to remove the reductant.

The percentage monomer was analyzed over a period of 0 to 23 hours.

TABLE 1

The Percentage Monomer after Treatment with 50 mM β-mea

| Time (h) | Concentration of Antibody Molecule in g/L | % Monomer |
| --- | --- | --- |
| 0 | 14.8 | 25.2 |
| 1 | 14.8 | 25.1 |
| 2 | 14.8 | 25.0 |
| 3 | 14.8 | 24.9 |
| 4 | 14.9 | 25.1 |
| 5 | 14.9 | 25.0 |
| 6 | 14.9 | 25.1 |
| 23 | 14.9 | 25.0 |

Combination of Reductant and Denaturant

The feed was purified antibody as provided in Example 1, concentration 1.1 g/L and 14% monomer.

3M urea was used as the denaturant and 50 mM β-mea as the reductant. Urea was added first to the feed, followed by the reductant. Following addition of the reductant, time points were sampled up to 5 hours, the first immediately after the addition of β-mea (labelled 0 h). Every sample was buffer exchanged and then analysed by SE UPLC. The experiments were performed at room temperature.

The results are shown in Table 2:

| Time (h) | % Area by SE-UPLC | | | | | Total amount of protein (ug) | Amount of monomer (ug) |
| --- | --- | --- | --- | --- | --- | --- | --- |
| | % HMWS | % Quatramer | % Trimer | % Dimer | % Monomer | | |
| 0.0 | 29.7 | 16.8 | 20.5 | 18.9 | 14.2 | 1.1 | 0.2 |
| 0.5 | | | 3.5 | 8.6 | 76.6 | 0.8 | 0.6 |
| 1.0 | 0.5 | 0.5 | 2.1 | 8.5 | 80.3 | 0.8 | 0.7 |
| 1.5 | 0.7 | | 2.4 | 7.6 | 83.2 | 0.9 | 0.7 |
| 2.0 | 0.8 | 0.5 | 2.0 | 8.3 | 82.6 | 1.0 | 0.8 |
| 3.0 | 1.2 | 0.6 | 2.0 | 8.4 | 82.3 | 0.9 | 0.7 |
| 5.0 | 1.8 | 0.6 | 2.5 | 8.7 | 80.7 | 0.9 | 0.8 |

HMWS = high molecular weight species
SE-HPLC analysis was used to determine % monomer and monomer amount see also FIG. 1.

It can be seen that the use of 3M urea as the denaturant and 50 mM β-mea provided significantly improved percentage of monomer whilst also increasing monomer amount. The urea was capable of achieving conversion of multimers to monomers without reducing the disulfide bond between the heavy chains of the Fab.

Conclusion: β-mea was identified as the optimal reductant for the conversion reaction in order to reduce the Fv interchain disulphide bond while retaining the Fab interchain disulphide bond. Other reductant tested (data not shown) appeared to increase the % monomer by SE analysis but, as seen in subsequent SDS PAGE analysis, they reduce both the interchain disulphide bonds, hence are not useful in conversion of Fab-dsFv.

Combination of Reductant and Denaturant with Varying Concentrations:

A screening experiment was performed varying the concentration of denaturant and reductant in order to identify optimal conditions to convert multimeric species into monomers. The feed was purified antibody as provided in Example 1. Each experiment was performed at room temperature, with a 1200 rpm mixing rate, a feed concentration of 1.1 g/L and a 5 mL sample volume. Urea was added first to the feed, quickly followed by the reductant. Time course samples were taken from 0 to 5 hours. Samples were immediately frozen at −20° C. at the end of the conversion step. 1 day later the samples were 0.22 µm filtered and analysed by SE UPLC. The conversion reaction continued until the analysis because the denaturant and reductant were still present. Denaturants tested were urea and Guanidine hydrochloride (GuHCl).

TABLE 3

Experimental Plan for a Combination of Denaturant and Reductant

| β-mEA concentration (mM) | Denaturant concentration (M) | |
|---|---|---|
| | Urea | GuHCl |
| 0 | 1.0 | 1.0 |
| 10 | 1.0 | 1.0 |
| 50 | 1.0 | 1.0 |
| 0 | 3.0 | 1.8 |
| 10 | 3.0 | 1.8 |
| 50 | 3.0 | 1.8 |
| 0 | 5.0 | 2.5 |
| 10 | 5.0 | 2.5 |
| 50 | 5.0 | 2.5 |

The results of size exclusion chromatography performed on the samples is shown in FIGS. 2A-E.

Figure 2A:
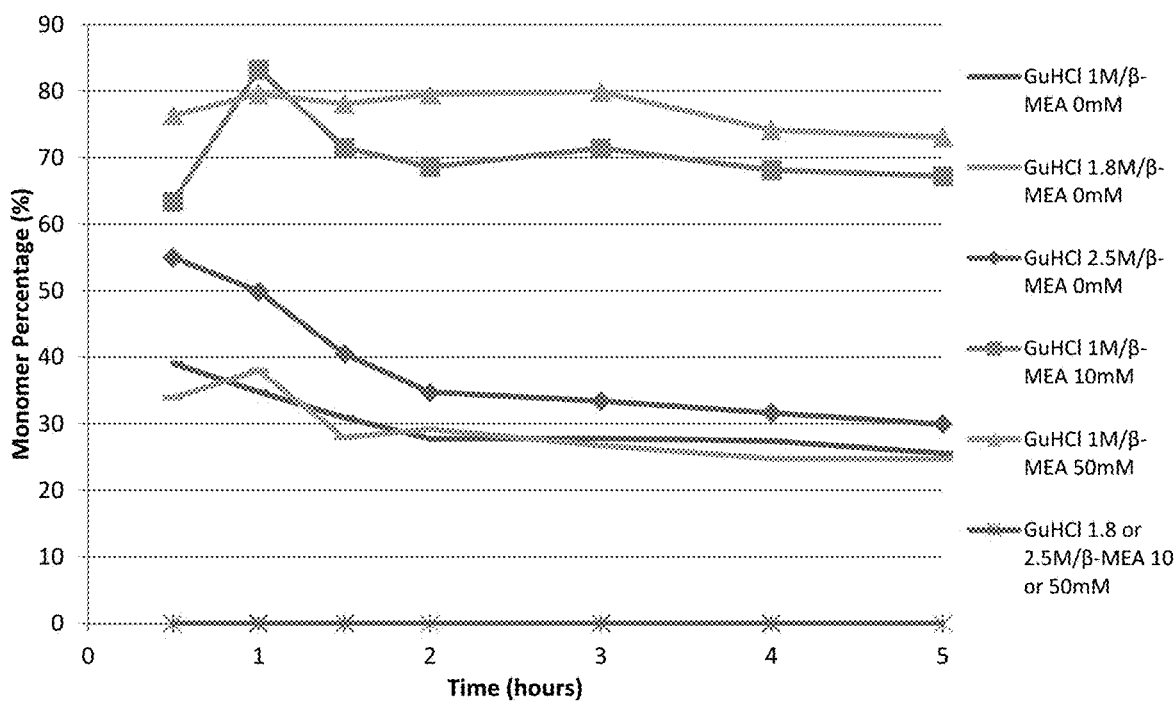
FIG. 2A+2B shows % monomer and monomer concentration respectively obtained for antibody A26 Fab-645dsFv after performing a conversion employing β-mea and guanidine.
Figure 2B:
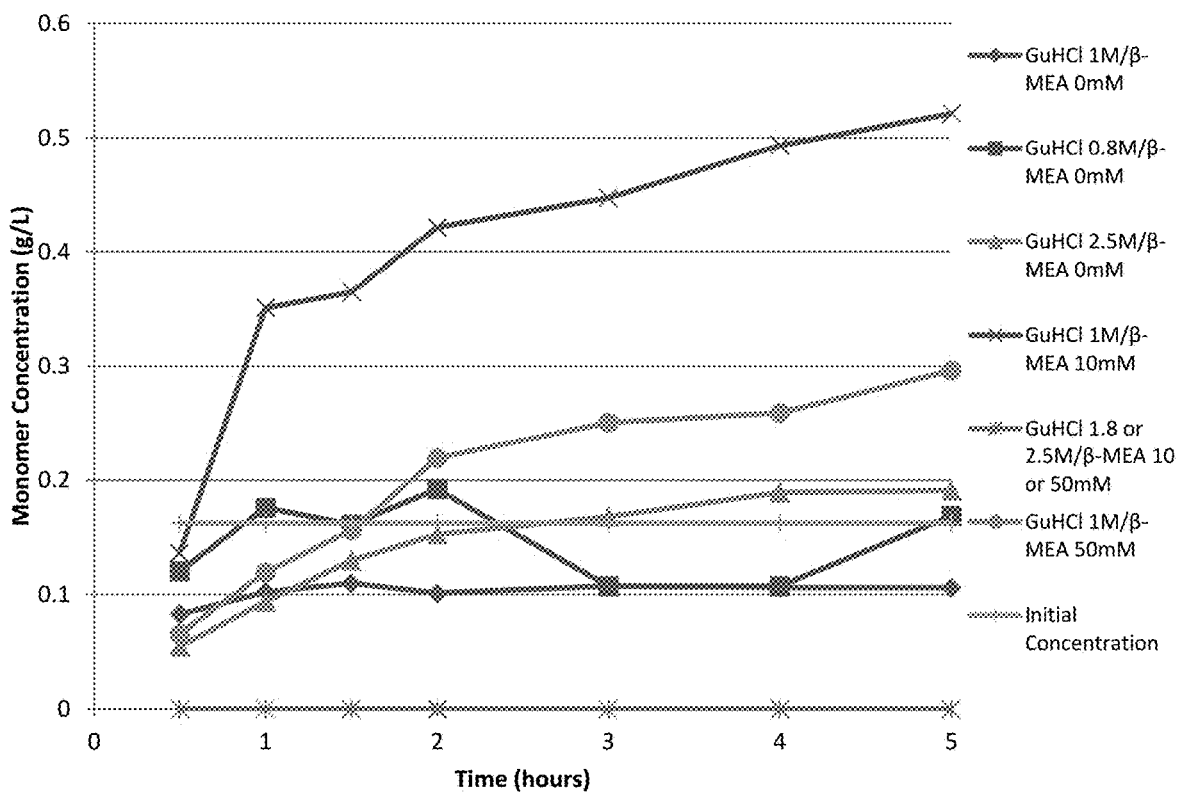
FIG. 2C+D shows the % monomer and yield respectively obtained for antibody A26 Fab-645dsFv after performing a conversion employing β-mea and urea.
FIG. 2E shows the amount of monomer obtained for antibody A26 Fab-645dsFv after performing a conversion employing β-mea and urea.

1M guanadine with 10 mM β-mea gave the highest monomer yield (see FIG. 2B).

Figure 2C:
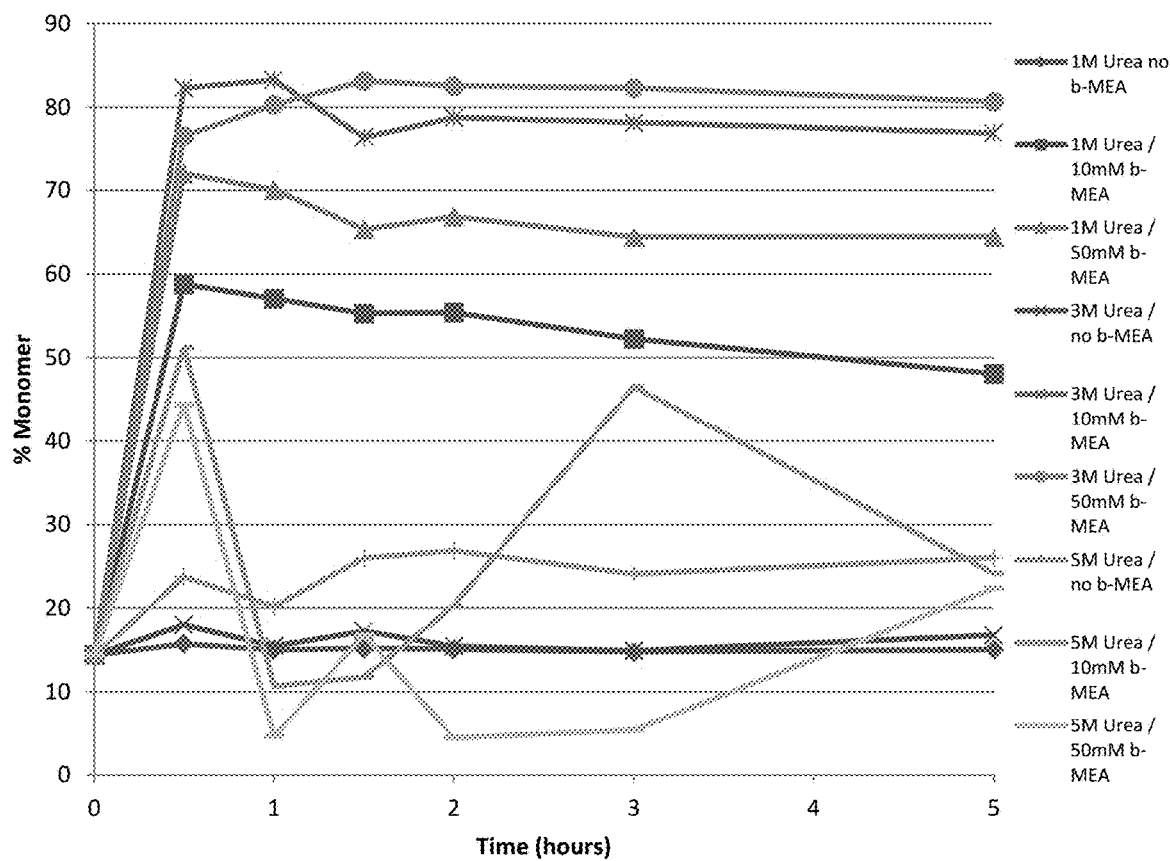
Figure 2D:
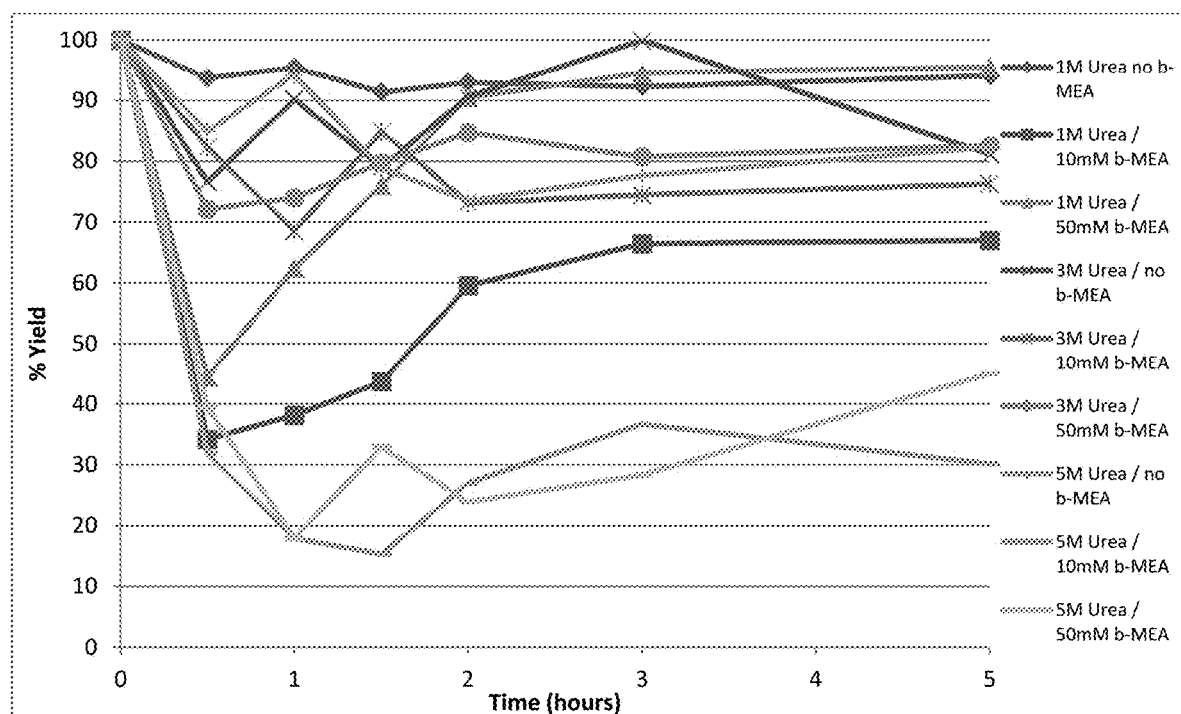
Figure 2E:
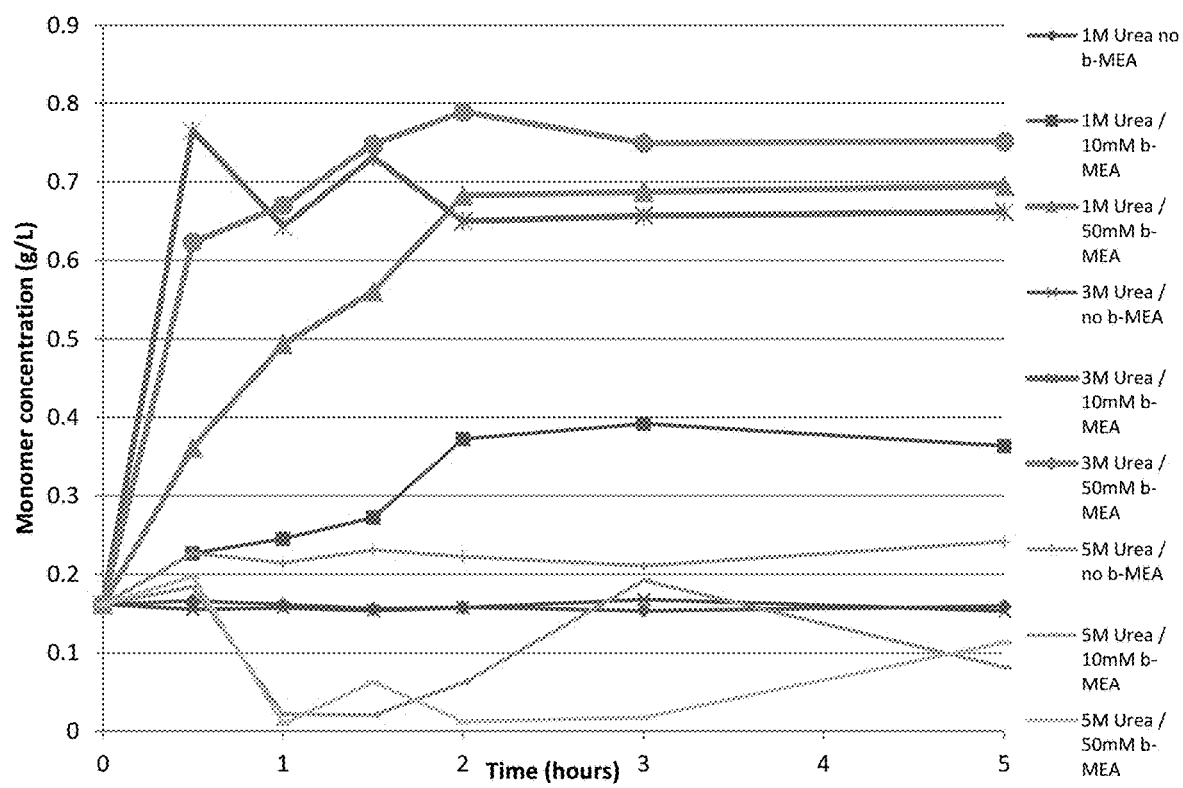

81% monomer was seen in the 3M urea and 50 mM β-mea sample (see FIG. 2C). Even with only 10 mM β-mea 77% monomer was seen in the 3M urea sample (FIG. 2C). The 1M urea samples had still significant increase in % monomer but lower % monomer compared to the 3M urea samples.

As shown in FIGS. 2 D and 2 E, showing % yield and monomer concentration, with 3M urea, 50 mM β-mea there was 84.7% for the yield and 0.79 g/L of monomer after 2 h (5 times higher than the feed). There were also high monomer recoveries in the 3M urea, 10 mM β-mea and the 1M urea, 50 mM β-mea samples. 5M urea resulted in some product loss in these samples.

Conclusion: The results using 3M urea as the denaturant were very promising and provided a 5-fold increase in monomer whilst a 4 fold increase in monomer was seen with guanidine.

Example 3: Urea Conversion Time Course

Figure 3:
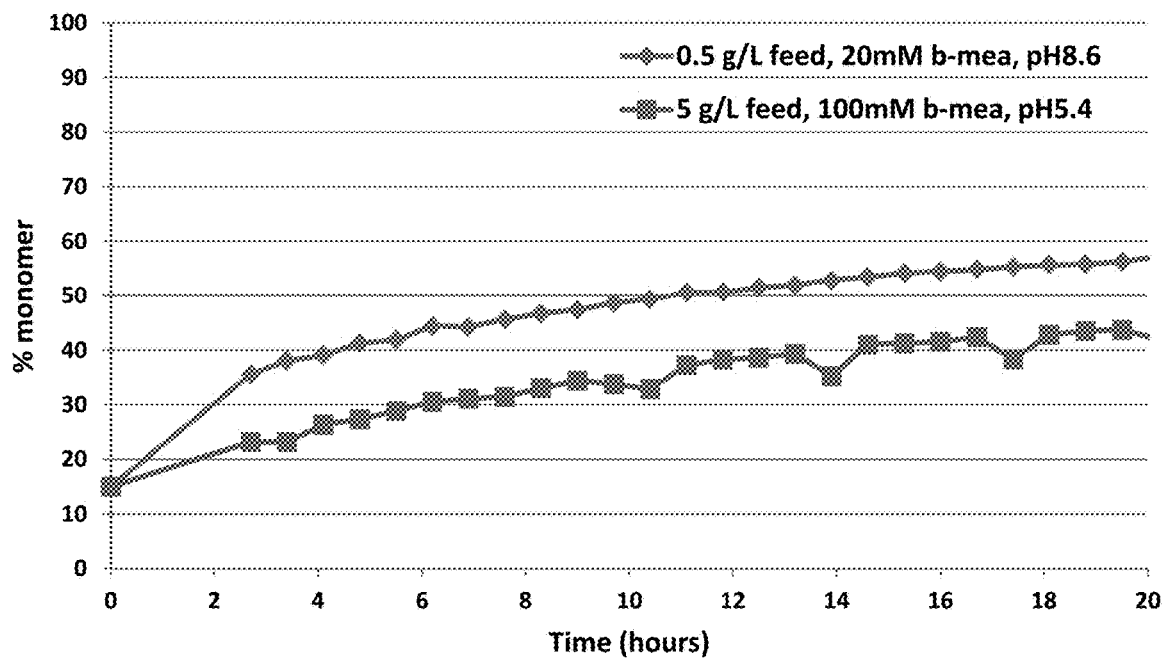
FIG. 3 shows a time course of % monomer in a composition of antibody A26 Fab-645dsFv during a conversion step employing β-mea and urea.
Figure 4:
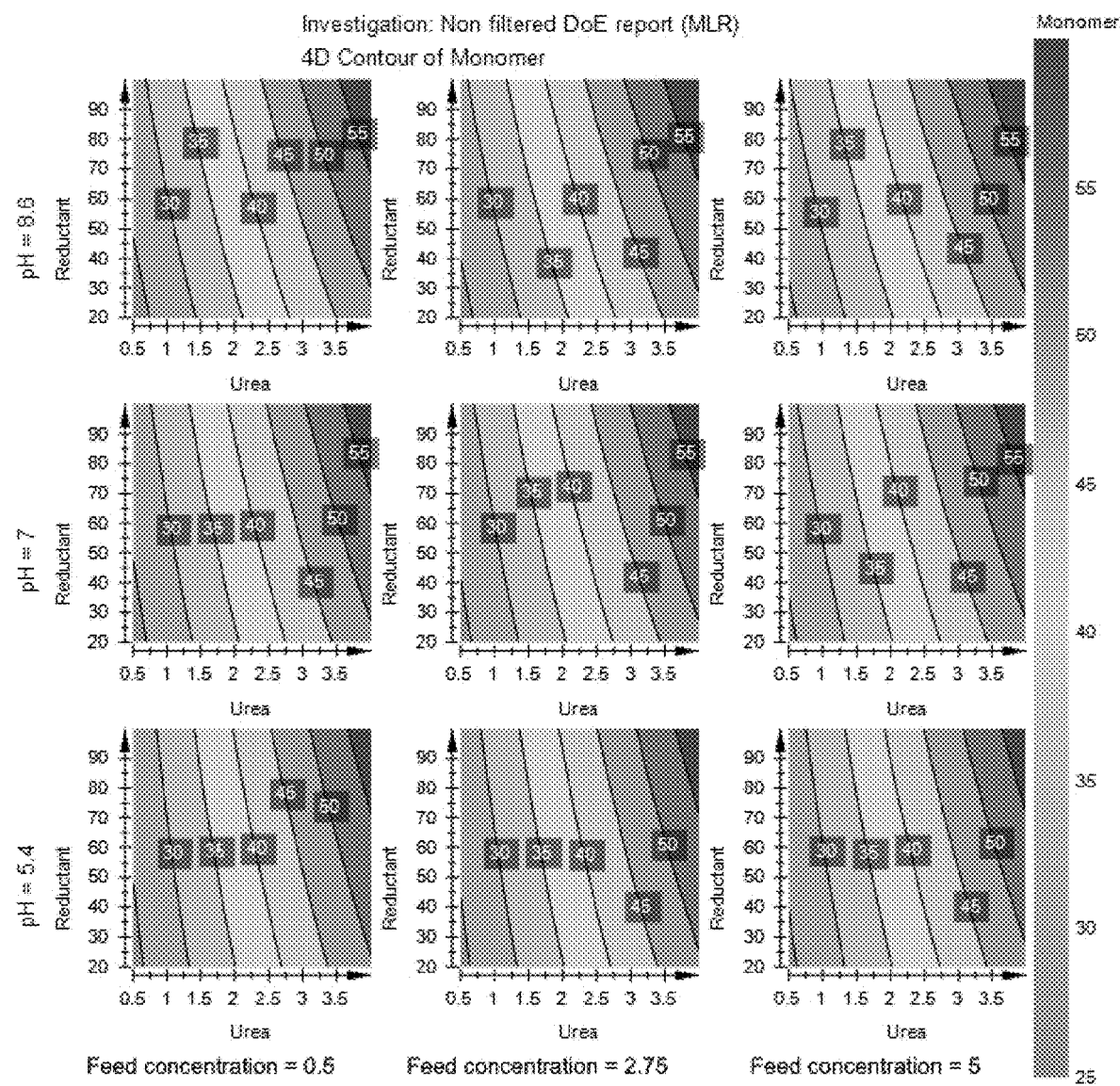
FIG. 4 shows a contour plot for % monomer yield for a range of parameters.

A time course study for the urea conversion was performed on SE UPLC column. The feed was purified antibody as provided in Example 1. Two samples were prepared in 1.5 mL vials and run on SE UPLC column. Urea was added first to the feed, quickly followed by the reductant. Time points were performed every 40 minutes. The conditions for the samples were:

0.5 g/L feed concentration, 20 mM β-mea concentration, pH 8.6, 4M Urea concentration 5.0 g/L feed concentration, 100 mM β-mea concentration, pH 5.4, 4M Urea concentration The temperature of the sample compartment was set to 10° C., which would have reduced the speed of the reaction, with respect to reaction in room temperature. The results obtained from the SE-UPLC analysis are shown in FIG. 3.

Example 4: Parameter Screening—1

In order to find the optimum conditions for the conversion step where β-mea is used as reductant and urea as denaturant, parameters thought to have the greatest effect on the conversion reaction were investigated. These were feed concentration, urea concentration, β-mea concentration and pH, see table 3. The feed was purified antibody as provided in Example 1. The feed material contained 15% monomer and the time used for all conversion steps was 5 hours. Urea was added first to the feed, quickly followed by the reductant.

TABLE 4

Parameter ranges screened

| Factors | Levels |
|---|---|
| Feed concentration | 0.5-5 g/L |
| β-mea concentration | 20-100 mM |
| Urea concentration | 0.5-4M |
| pH | 5.4-8.6 |

The conversion steps were performed in a 96 deep well plate, each experiment was repeated, and the experiments prepared using the TECAN robot. The experiments were performed at room temperature and the samples analyzed by SE UPLC. Responses measured were % monomer, total yield and monomer yield.

The experimental design is shown in Table 5:

| Exp Name | Feed conc. (g/L) | pH | β-mea conc. (mM) | Urea conc. (M) |
|---|---|---|---|---|
| N1 | 0.5 | 5.4 | 20 | 0.5 |
| N2 | 5.0 | 5.4 | 20 | 0.5 |
| N3 | 0.5 | 8.6 | 20 | 0.5 |
| N4 | 5.0 | 8.6 | 20 | 0.5 |
| N5 | 0.5 | 5.4 | 100 | 0.5 |
| N6 | 5.0 | 5.4 | 100 | 0.5 |
| N7 | 0.5 | 8.6 | 100 | 0.5 |
| N8 | 5.0 | 8.6 | 100 | 0.5 |
| N9 | 0.5 | 5.4 | 20 | 4.0 |
| N10 | 5.0 | 5.4 | 20 | 4.0 |
| N11 | 0.5 | 8.6 | 20 | 4.0 |
| N12 | 5.0 | 8.6 | 20 | 4.0 |
| N13 | 0.5 | 5.4 | 100 | 4.0 |
| N14 | 5.0 | 5.4 | 100 | 4.0 |
| N15 | 0.5 | 8.6 | 100 | 4.0 |
| N16 | 5.0 | 8.6 | 100 | 4.0 |
| N17 | 2.75 | 7.0 | 60 | 2.25 |
| N18 | 2.75 | 7.0 | 60 | 2.25 |
| N19 | 2.75 | 7.0 | 60 | 2.25 |

The samples were analyzed by SE-HPLC and the results are shown in Table 6.

TABLE 6

Results for the 1st Parameter Ranges Screening

| | Feed | | | | Un filtered samples | | |
|---|---|---|---|---|---|---|---|
| Exp Name | concentration (g/L) | pH | Reductant (mM) | Urea (M) | Monomer (%) | Yield (%) | Monomer Yield (A) |
| N1 | 0.5 | 5.4 | 20 | 0.5 | 24.0 | 114.0 | 27.4 |
| N2 | 5.0 | 5.4 | 20 | 0.5 | 22.4 | 110.0 | 25.3 |
| N3 | 0.5 | 8.6 | 20 | 0.5 | 23.0 | 107.8 | 28.8 |
| N4 | 5.0 | 8.6 | 20 | 0.5 | 24.2 | 103.4 | 27.9 |
| N5 | 0.5 | 5.4 | 100 | 0.5 | 26.8 | 106.1 | 52.4 |
| N6 | 5.0 | 5.4 | 100 | 0.5 | 27.9 | 107.4 | 50.7 |
| N7 | 0.5 | 8.6 | 100 | 0.5 | 27.0 | 97.8 | 55.2 |
| N8 | 5.0 | 8.6 | 100 | 0.5 | 29.7 | 94.4 | 57.1 |
| N9 | 0.5 | 5.4 | 20 | 4.0 | 49.4 | 99.8 | 22.3 |
| N10 | 5.0 | 5.4 | 20 | 4.0 | 49.1 | 93.6 | 22.6 |
| N11 | 0.5 | 8.6 | 20 | 4.0 | 47.2 | 99.7 | 27.8 |
| N12 | 5.0 | 8.6 | 20 | 4.0 | 48.8 | 93.5 | 27.7 |
| N13 | 0.5 | 5.4 | 100 | 4.0 | 56.5 | 96.2 | 47.3 |
| N14 | 5.0 | 5.4 | 100 | 4.0 | 58.0 | 91.5 | 44.6 |
| N15 | 0.5 | 8.6 | 100 | 4.0 | 60.5 | 89.2 | 51.7 |
| N16 | 5.0 | 8.6 | 100 | 4.0 | 58.4 | 85.2 | 49.7 |
| N17 | 2.8 | 7.0 | 60 | 2.3 | 42.4 | 100.8 | 42.8 |
| N18 | 2.8 | 7.0 | 60 | 2.3 | 42.4 | 101.4 | 43.0 |
| N19 | 2.8 | 7.0 | 60 | 2.3 | 42.3 | 101.7 | 43.1 |

The contour plot for % monomer yield is given in FIG. 16.

The optimal conditions for maximizing the % monomer was the highest reductant concentration (100 mM β-mea) and the highest denaturant concentration (4M urea).

Urea concentration had a strong positive effect on % monomer. β-mea concentration had a weaker positive impact on % monomer. From this 1st screening of parameter ranges, further ranges were chosen for a subsequent 2nd screening. These were 80-150 mM for β-mea concentration and 2.5 to 5M for urea concentration. These ranges were chosen as they were the limit for the protein to prevent single chain formation.

Example 5: Parameter Screening—2

In order to find the optimal conditions for maximizing monomer yield, a second parameter ranges screening was performed by selecting promising ranges from Example 4. The ranges chosen for the second screening are shown in Table 7.

TABLE 7

Parameters for the $2^{nd}$ Screening

| Factors | Levels |
|---|---|
| β-mea concentration | 80-150 mM |
| Urea concentration | 2.5-5M |
| pH | 5.4-8.6 |

The feed was purified antibody as provided in Example 1. The conversion steps were performed in a 96 deep well plate, each experiment was repeated, and the experiments prepared using the TECAN robot. The feed material contained 15% monomer and the time used for all conversion steps was 5 hours. Urea was added first to the feed, quickly followed by the reductant. The experiment was performed at room temperature and the samples analyzed by SE UPLC after filtration. The model was fitted using multiple linear regressions.

The results obtained in this study are shown in Table 8.

TABLE 8

Results for the 2nd Parameter Ranges Screening

| Exp No | Urea conc. (M) | pH | B-mea conc. (mM) | % yield | % monomer yield | % monomer |
|---|---|---|---|---|---|---|
| 1 | 2.5 | 5.4 | 80 | 72.9 | 29.8 | 40.9 |
| 2 | 5.0 | 5.4 | 80 | 88.6 | 68.4 | 77.2 |
| 3 | 2.5 | 8.6 | 80 | 76.5 | 33.1 | 43.3 |
| 4 | 5.0 | 8.6 | 80 | 89.6 | 68.3 | 76.3 |
| 5 | 2.5 | 5.4 | 150 | 78.5 | 35.5 | 45.2 |
| 6 | 5.0 | 5.4 | 150 | 86.0 | 69.0 | 80.3 |
| 7 | 2.5 | 8.6 | 150 | 79.9 | 38.2 | 47.8 |
| 8 | 5.0 | 8.6 | 150 | 87.8 | 70.1 | 79.9 |
| 9 | 2.5 | 7.0 | 115 | 78.6 | 36.2 | 46.1 |
| 10 | 5.0 | 7.0 | 115 | 88.0 | 69.1 | 78.6 |
| 11 | 3.8 | 5.4 | 115 | 86.6 | 52.1 | 60.2 |
| 12 | 3.8 | 8.6 | 115 | 88.6 | 55.7 | 62.9 |
| 13 | 3.8 | 7.0 | 80 | 86.5 | 52.2 | 60.3 |
| 14 | 3.8 | 7.0 | 150 | 90.2 | 60.1 | 66.6 |
| 15 | 3.8 | 7.0 | 115 | 89.8 | 57.4 | 63.9 |
| 16 | 3.8 | 7.0 | 115 | 89.3 | 57.1 | 64.0 |
| 17 | 3.8 | 7.0 | 115 | 90.4 | 58.2 | 64.4 |

As in the previous screening study, urea concentration had the strongest (positive) effect on % monomer, while β-mea had a much smaller (positive) effect across the ranges investigated. Changing the β-mea concentration from 80 to 150 mM had little effect on the conversion reaction.

Figure 5:
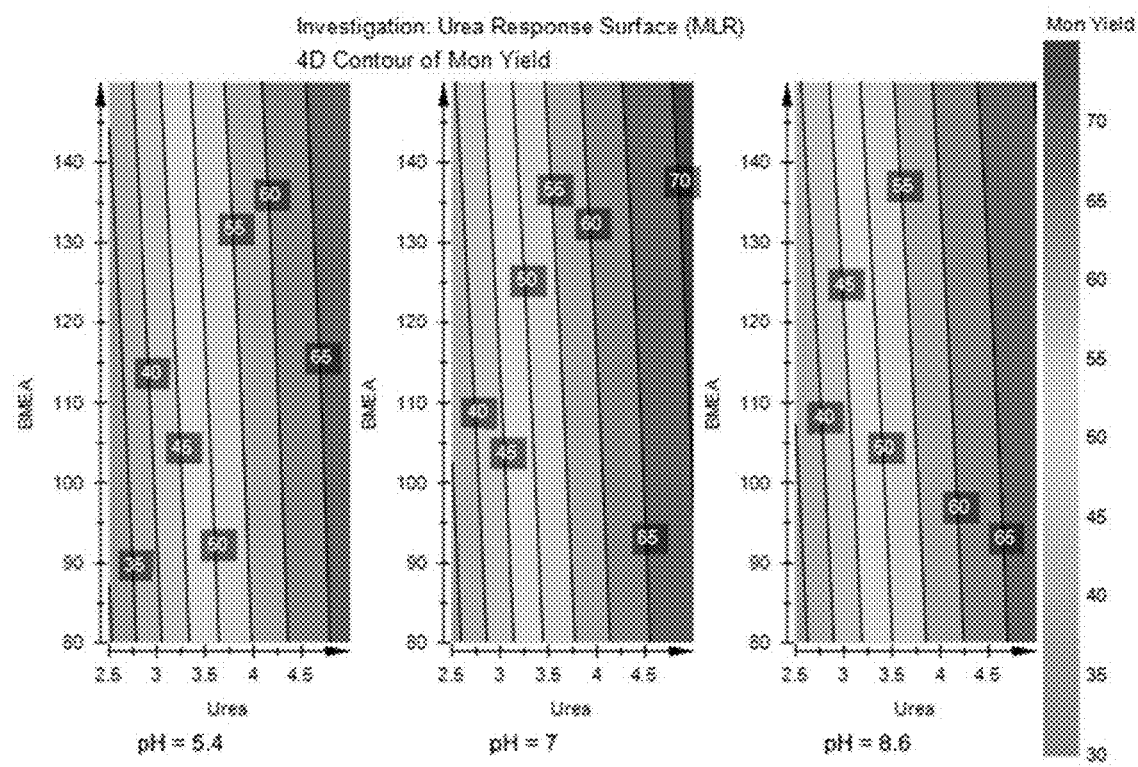
FIG. 5 shows a contour plot for % monomer yield for a range of parameters.

In the experiments containing 2.5 M urea had low yields, while all other experiments with Urea concentrations of 3.8 M and above all had similar significantly improved yields. The contour plot for % monomer yield is shown in FIG. 5.

Hence it was found that where a Fab-dsFv conversion was made by treating the recombinantly expressed polypeptide with β-mea in 80 to 150 mM and urea in 3.8 M to 5M, percentage of monomer was increased.

Example 6: Robustness Testing

Figure 6:
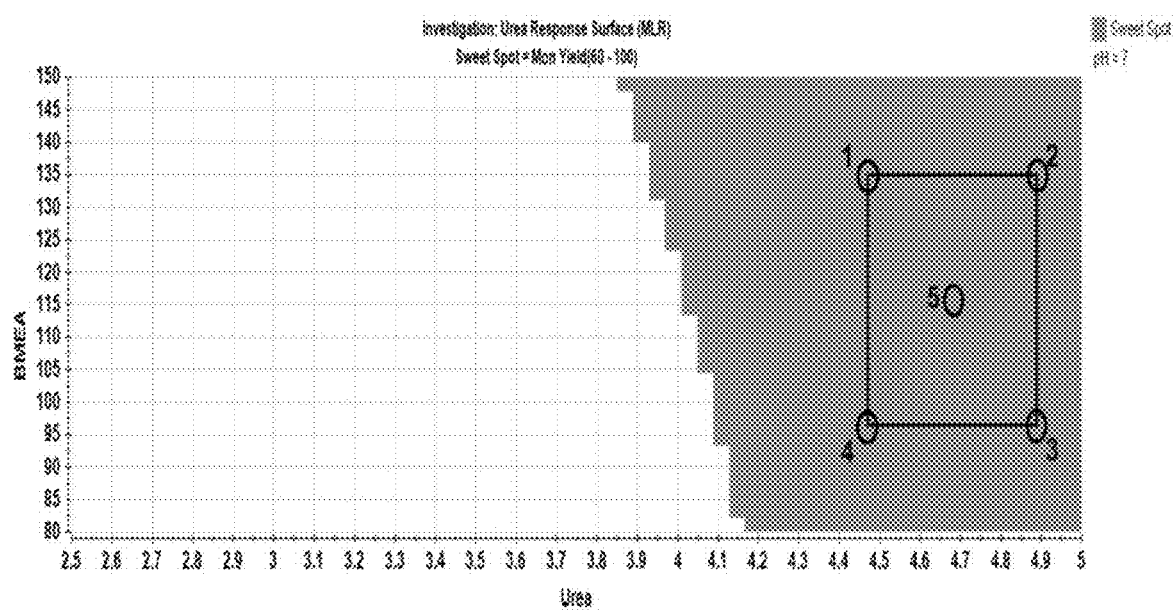
FIG. 6 shows a sweet spot plot monomer yield for urea concentration and β-mea concentration.

A sweet spot plot across the experimental space for monomer yields of 60% and above found in Example 5, is given in FIG. 6.

Five experimental points in this area were chosen to confirm the results from Example 5 and to provide a robust space in which to perform the conversion step. pH was shown to have no significant effect on monomer yield so all experiments were run at pH 7.

The feed was purified antibody as provided in Example 1. The feed concentration for the samples was 2.75 g/L and 15% of this was monomer. The experimental points and results from the SE UPLC analysis are shown in Table 9. The conversion step was run for 6 hours.

TABLE 9

Experiment results for robustness tests

| | Factors | | | Responses | | |
|---|---|---|---|---|---|---|
| Experiment | Urea conc. (M) | pH | β-mea conc. (mM) | Yield (%) | % Monomer | Monomer yield (%) |
| 1 | 4.5 | 7.0 | 135 | 89.8 | 80.7 | 72.5 |
| 2 | 4.9 | 7.0 | 135 | 88.1 | 87.0 | 76.7 |
| 3 | 4.9 | 7.0 | 95 | 87.4 | 83.7 | 73.2 |
| 4 | 4.5 | 7.0 | 95 | 89.1 | 80.0 | 71.3 |
| 5 | 4.7 | 7.0 | 115 | 92.9 | 81.8 | 75.9 |

Across the five experiments the monomer yield varied from 71 to 77%. The yield and % monomer responses were also fairly consistent across the experiments.

Figure 7:
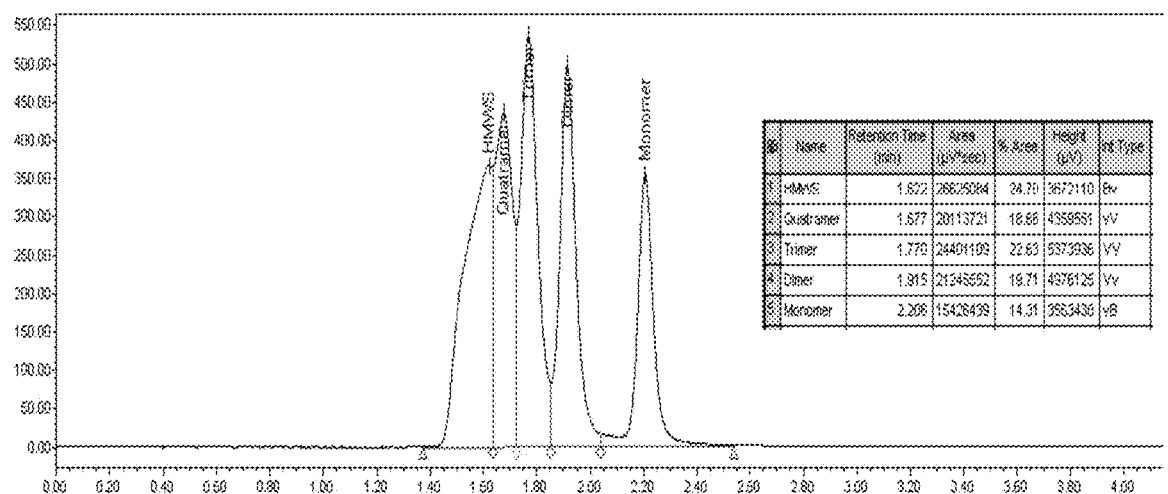
FIG. 7 show SE-UPLC chromatogram feed material prior to conversion step.
Figure 8:
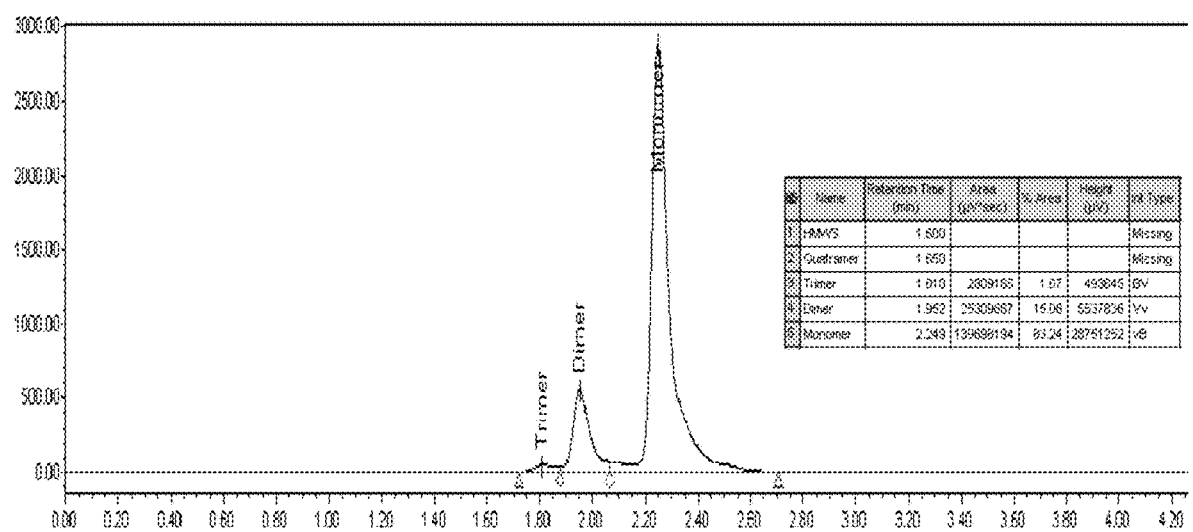
FIG. 8 shows SE-UPLC chromatogram of the sample after the conversion step, wherein the test conditions were 4.7 M Urea and 115 mM β-mea.

The SE-UPLC chromatograms of the samples before and after a conversion step from Experiment 5 in Table 9 using 4.7M urea and 115 mM β-mea are shown in FIG. 7 and FIG. 8.

Example 7: Conversion at 2 L Scale

CHO expression and clarification of A26Fab-645dsFv was carried out as in Example 1 to provide clarified culture fluid as the feed for the 2 L scale experiment. A conversion experiment was performed in a 2 L fermentation vessel, using a conversion volume of 2 L. The concentration of antibody was 2.2 g/L, of which 30% was monomer. The experimental conditions are shown in table 10, and the conversion step was performed for 17 h. In the experiment the reductant β-mea was added first, followed by Urea. The samples were analyzed by SE UPLC.

TABLE 10

Experimental conditions for 2 L conversion experiment

| Urea conc. (M) | PH | ° C. | β-mea conc. (mM) |
|---|---|---|---|
| 3.0 | 7 | Room temp | 50 |

TABLE 11

Experimental results for 2 L conversion experiment

| | Cell Culture Fluid Load (Pre Conversion Step) | | | | Cell Culture Fluid Post Conversion | | | | |
|---|---|---|---|---|---|---|---|---|---|
| Titre (g/L) | Ab load (g) | % Monomer | Monomer load (g) | Titre (g/L) | Ab recovered (g) | Ab Yield (%) | % Monomer | Monomer recovered (g) | Monomer yield (%) |
| 2.20 | 4.40 | 30.2 | 1.33 | 1.68 | 3.36 | 76.4 | 78.3 | 2.63 | 198.0 |

It was possible to scale up the conversion step to 2 L scale, in vessels representative of those used at manufacturing scale. It was possible to significantly increase the amount of monomer following the conversion step with β-mea and Urea.

Conclusion:

Robust conditions for the conversion step were identified, which were: 4.5 to 4.9 M Urea, 95 to 135 mM β-mea, 6 hours, feed conc. 2.75 g/L.

Most robust conditions were identified to be: 4.7 M Urea, 115 mM β-mea, 6 hours, feed conc. 2.75 g/L.

Using these most robust conditions, the % monomer was surprisingly increased from 15% to 82%. The yield for the conversion step was 93%, resulting in a monomer yield of 76%. The monomer concentration in the feed was 0.4 g/L, and the monomer concentration in the product after conversion was 2.0 g/L. This is an unexpected 5 fold increase in the amount of monomer after the conversion step.

The conversion step was successfully scaled up to 2 L scale using 3M Urea and 50 mM β-mea, using vessels representative of those at manufacturing scale.

The invention claimed is:

1. A method of increasing the percentage of monomer in a composition of recombinantly expressed antibody molecules characterised in that the antibody molecule comprises at least one Fv comprising one VH and one VL and having specificity for an antigen of interest wherein said VH and VL are connected directly via one or more linkers and are stabilised by a disulfide bond therebetween and comprises a dsscFv, Fab-2xdsscFv, Fab-dsscFv-dsFv, Fab-dsscFv-sdAb, Fab-dsscFv-scFv or Fab-dsscFv, said method comprises:
   a) a conversion step of treating the composition of recombinantly expressed antibody molecules with a denaturant selected from urea at a concentration of 1 to 5 molar and/or guanidine hydrochloride at a concentration of 1 to 2 molar;
   b) wherein step a) is performed in the presence of a reducing agent or after treatment with a reducing agent, the reducing agent having a concentration of 10 to 150 millimolar.

2. The method according to claim 1, wherein the reducing agent is selected from the group consisting of: glutathione (GSH), ethylsulfite, 2-mercaptoethanol (BME), 2-mercaptoethylamine (BMEA), cysteine-HCl and dithiothreitol (DTT).

3. The method according to claim 2, wherein the reducing agent is selected from 2-mercaptoethanol (BME) and 2-mercaptoethylamine (BMEA).

4. The method according to claim 3, wherein the 2-mercaptoethylamine is 95 to 135 millimolar.

5. The method according to claim 1, wherein the denaturant is urea and is at a concentration of 1 to 5 molar.

6. The method according to claim 1, wherein the denaturant is Guanidine hydrochloride and is at a concentration of 1 to 2 molar.

7. The method according to claim 1, wherein step a) is carried out for a period of 2 to 70 hours.

8. The method according to claim 1, wherein the method is performed at room temperature.

9. The method according to claim 1, wherein the antibody is at a concentration in the range 0.5 g/L to 5 g/L.

10. The method according to claim 1, wherein the conversion step is performed in the presence of concomitant stirring.

11. The method according to claim 10, wherein the stirring rate is between 100 and 1200 rpm.

12. The method according to claim 1, comprising a further step of downstream purification.

13. The method according to claim 12, wherein downstream processing comprises chromatography.

14. The method according to claim 1, wherein the denaturant is urea and is at a concentration of 3 to 5 molar; or a concentration of 4.5 to 4.9 molar.

15. The method according to claim 1, wherein the denaturant is urea and is at a concentration of 4.5 to 4.9 molar.

* * * * *

SEQUENCE LISTING

<160> NUMBER OF SEQ ID NOS: 90

<210> SEQ ID NO 1
<211> LENGTH: 5
<212> TYPE: PRT
<213> ORGANISM: Artificial
<220> FEATURE:
<223> OTHER INFORMATION: CDRH1

<400> SEQUENCE: 1

Asn Tyr Gly Ile His
1               5

<210> SEQ ID NO 2
<211> LENGTH: 17
<212> TYPE: PRT

```
<213> ORGANISM: Artificial
<220> FEATURE:
<223> OTHER INFORMATION: CDRH2

<400> SEQUENCE: 2

Ser Ile Ser Pro Ser Gly Gly Leu Thr Tyr Tyr Arg Asp Ser Val Lys
1               5                   10                  15

Gly

<210> SEQ ID NO 3
<211> LENGTH: 8
<212> TYPE: PRT
<213> ORGANISM: Artificial
<220> FEATURE:
<223> OTHER INFORMATION: CDRH3

<400> SEQUENCE: 3

Gly Gly Glu Gly Ile Phe Asp Tyr
1               5

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

Arg Ala Thr Gln Ser Ile Tyr Asn Ala Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDRL2

<400> SEQUENCE: 5

Asn Ala Asn Thr Leu His Thr
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

Gln Gln Tyr Tyr Asp Tyr Pro Leu Thr
1               5

<210> SEQ ID NO 7
<211> LENGTH: 108
<212> TYPE: PRT
<213> ORGANISM: Artificial
<220> FEATURE:
<223> OTHER INFORMATION: Light chain variable region of antibody A26

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30
```

```
Leu Ala Trp Tyr Gln Gln Lys Pro Gly Lys Ala Pro Lys Leu Leu Ile
            35                  40                  45

Tyr Asn Ala Asn Thr Leu His Thr Gly Val Pro Ser Arg Phe Ser Ala
 50                  55                  60

Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg
            100                 105
```

```
<210> SEQ ID NO 8
<211> LENGTH: 117
<212> TYPE: PRT
<213> ORGANISM: Artificial
<220> FEATURE:
<223> OTHER INFORMATION: Heavy chain variable region of antibody A26

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
 50                  55                  60

Lys Gly Arg Phe Thr Ile Ser Arg Asp Asp Ala Lys Asn Ser Pro Tyr
 65                  70                  75                  80

Leu Gln Met Asn Ser Leu Arg Ala Glu Asp Thr Ala Val Tyr Tyr Cys
                 85                  90                  95

Ala Thr Gly Gly Glu Gly Ile Phe Asp Tyr Trp Gly Gln Gly Thr Leu
            100                 105                 110

Val Thr Val Ser Ser
        115
```

```
<210> SEQ ID NO 9
<211> LENGTH: 214
<212> TYPE: PRT
<213> ORGANISM: Artificial
<220> FEATURE:
<223> OTHER INFORMATION: Light chain of anti-OX40 antibody Fab component

<400> SEQUENCE: 9

Asp Ile Gln Met Thr Gln Ser Pro Ser Ser Leu Ser Ala Ser Val Gly
 1               5                  10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
 50                  55                  60

Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 220
<212> TYPE: PRT
<213> ORGANISM: Artificial
<220> FEATURE:
<223> OTHER INFORMATION: Heavy chain of anti-OX40 antibody Fab component

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 11
<211> LENGTH: 121
<212> TYPE: PRT
<213> ORGANISM: Artificial
```

<220> FEATURE:
<223> OTHER INFORMATION: Heavy chain of anti-albumin Fv component

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 12
<211> LENGTH: 112
<212> TYPE: PRT
<213> ORGANISM: Artificial
<220> FEATURE:
<223> OTHER INFORMATION: Light chain of anti-albumin Fv component

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ser Ile
                85                  90                  95

Ser Asp Thr Thr Phe Gly Cys Gly Thr Lys Val Glu Ile Lys Arg Thr
            100                 105                 110

<210> SEQ ID NO 13
<211> LENGTH: 16
<212> TYPE: PRT
<213> ORGANISM: Artificial
<220> FEATURE:
<223> OTHER INFORMATION: Linker 1

<400> SEQUENCE: 13

Ser Gly Gly Gly Gly Ser Gly Gly Gly Gly Thr Gly Gly Gly Gly Ser
1               5                   10                  15

<210> SEQ ID NO 14
<211> LENGTH: 15
<212> TYPE: PRT
<213> ORGANISM: Artificial
<220> FEATURE:

<223> OTHER INFORMATION: Linker 2

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 357
<212> TYPE: PRT
<213> ORGANISM: Artificial
<220> FEATURE:
<223> OTHER INFORMATION: A26 Fab Heavy-(G4S,G4T,G4S)-645dsFv(gH5)

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Thr Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

```
Gly Tyr Ser Thr Ala Pro Tyr Phe Asp Leu Trp Gly Gln Gly Thr Leu
            340                 345                 350

Val Thr Val Ser Ser
        355

<210> SEQ ID NO 16
<211> LENGTH: 341
<212> TYPE: PRT
<213> ORGANISM: Artificial
<220> FEATURE:
<223> OTHER INFORMATION: A26 Fab Light-(3xG4S)-645dsFv(gL4)

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Asp Ile Gln Met Thr Gln Ser Pro Ser Ser Val
225                 230                 235                 240

Ser Ala Ser Val Gly Asp Arg Val Thr Ile Thr Cys Gln Ser Ser Pro
                245                 250                 255

Ser Val Trp Ser Asn Phe Leu Ser Trp Tyr Gln Gln Lys Pro Gly Lys
            260                 265                 270

Ala Pro Lys Leu Leu Ile Tyr Glu Ala Ser Lys Leu Thr Ser Gly Val
        275                 280                 285

Pro Ser Arg Phe Ser Gly Ser Gly Ser Gly Thr Asp Phe Thr Leu Thr
    290                 295                 300

Ile Ser Ser Leu Gln Pro Glu Asp Phe Ala Thr Tyr Tyr Cys Gly Gly
305                 310                 315                 320

Gly Tyr Ser Ser Ile Ser Asp Thr Thr Phe Gly Cys Gly Thr Lys Val
                325                 330                 335
```

Glu Ile Lys Arg Thr
            340

<210> SEQ ID NO 17
<211> LENGTH: 119
<212> TYPE: PRT
<213> ORGANISM: Artificial
<220> FEATURE:
<223> OTHER INFORMATION: 645gH1 heavy chain variable domain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115

<210> SEQ ID NO 18
<211> LENGTH: 110
<212> TYPE: PRT
<213> ORGANISM: Artificial
<220> FEATURE:
<223> OTHER INFORMATION: 645gL1 light chain variable domain

<400> SEQUENCE: 18

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Cys Gly Thr Lys Val Glu Ile Lys
            100                 105                 110

<210> SEQ ID NO 19
<211> LENGTH: 355
<212> TYPE: PRT
<213> ORGANISM: Artificial
<220> FEATURE:
<223> OTHER INFORMATION: A26 Fab Heavy-( 3xG4S)-645dsFv(gH1)

<400> SEQUENCE: 19

```
Glu Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
            35                  40                  45

Ala Ser Ile Ser Pro Ser Gly Gly Leu Thr Tyr Tyr Arg Asp Ser Val
50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Ser Gly Gly Gly
210                 215                 220

Gly Ser Gly Gly Gly Gly Ser Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
            275                 280                 285

Ala Ser Gly Thr Thr Phe Tyr Ala Thr Trp Ala Lys Gly Arg Phe Thr
290                 295                 300

Ile Ser Arg Asp Ser Thr Thr Val Tyr Leu Gln Met Asn Ser Leu Arg
305                 310                 315                 320

Ala Glu Asp Thr Ala Val Tyr Tyr Cys Ala Arg Thr Val Pro Gly Tyr
                325                 330                 335

Ser Thr Ala Pro Tyr Phe Asp Leu Trp Gly Gln Gly Thr Leu Val Thr
            340                 345                 350

Val Ser Ser
        355

<210> SEQ ID NO 20
<211> LENGTH: 340
<212> TYPE: PRT
<213> ORGANISM: Artificial
<220> FEATURE:
<223> OTHER INFORMATION: A26 Fab Light-(3xG4S)-645dsFv(gL1)

<400> SEQUENCE: 20
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Thr Gln Ser Ile Tyr Asn Ala
             20                  25                  30

Leu Ala Trp Tyr Gln Gln Lys Pro Gly Lys Ala Pro Lys Leu Leu Ile
             35                  40                  45

Tyr Asn Ala Asn Thr Leu His Thr Gly Val Pro Ser Arg Phe Ser Ala
 50                  55                  60

Ser Gly Ser Gly Thr Asp Ser Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
             130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
             195                 200                 205

Phe Asn Arg Gly Glu Cys Ser Gly Gly Gly Ser Gly Gly Gly Gly
210                 215                 220

Ser Gly Gly Gly Gly Ser Asp Ile Val Met Thr Gln Ser Pro Ser Ser
225                 230                 235                 240

Val Ser Ala Ser Val Gly Asp Arg Val Thr Ile Thr Cys Gln Ser Ser
             245                 250                 255

Pro Ser Val Trp Ser Asn Phe Leu Ser Trp Tyr Gln Gln Lys Pro Gly
             260                 265                 270

Lys Ala Pro Lys Leu Leu Ile Tyr Glu Ala Ser Lys Leu Thr Ser Gly
             275                 280                 285

Val Pro Ser Arg Phe Lys Gly Ser Gly Ser Gly Thr Asp Phe Thr Leu
             290                 295                 300

Thr Ile Ser Ser Leu Gln Pro Glu Asp Phe Ala Thr Tyr Tyr Cys Gly
305                 310                 315                 320

Gly Gly Tyr Ser Ser Ile Ser Asp Thr Thr Phe Gly Cys Gly Thr Lys
             325                 330                 335

Val Glu Ile Lys
             340

<210> SEQ ID NO 21
<211> LENGTH: 1137
<212> TYPE: DNA
<213> ORGANISM: Artificial
<220> FEATURE:
<223> OTHER INFORMATION: Heavy chain A26-645(gH5) including E.coli OmpA
      leader

<400> SEQUENCE: 21
atgaagaaga ctgctatagc gatcgcagtg gcgctagctg gtttcgccac cgtggcgcaa    60
```

```
gctgaagttc agctggtcga gtctggaggc gggcttgtcc agcctggagg gagcctgcgt    120
ctctcttgtg cagcaagcgg tttcacgttc accaactacg gtatccactg gattcgtcag    180
gcaccaggta aggtctggaa tgggtagcc tctatctctc cgtctggtgg tctgacgtac     240
taccgtgact ctgtcaaagg tcgtttcacc atctctcgtg atgacgcgaa aaactctccg    300
tacctgcaaa tgaactctct gcgtgcagaa gataccgcag tgtactactg cgctactggt    360
ggtgaaggta tcttcgacta ctggggtcag ggtaccctgg taactgtctc gagcgcttct    420
acaaagggcc caagcgtttt cccactggct ccgtcctcta aatccacctc tggtggtacg    480
gctgcactgg gttgcctggt gaaagactac ttcccagaac cagttaccgt gtcttggaac    540
tctggtgcac tgacctctgg tgttcacacc tttccagcag ttctccagtc ttctggtctg    600
tactccctgt ctagcgtggt taccgttccg tcttcttctc tgggtactca gacctacatc    660
tgcaacgtca accacaaacc gtccaacacc aaggtcgaca aaaaagtcga gccgaaatcc    720
tgtagtggag gtggggctc aggtggaggc gggaccggtg gaggtggcag cgaggttcaa     780
ctgcttgagt ctggaggagg cctagtccag cctggaggga gcctgcgtct ctcttgtgca    840
gtaagcggca tcgacctgag caattacgcc atcaactggg tgagacaagc tccggggaag    900
tgtttagaat ggatcggtat aatatgggcc agtgggacga ccttttatgc tacatgggcg    960
aaaggaaggt ttacaattag ccgggacaat agcaaaaaca ccgtgtatct ccaaatgaac   1020
tccttgcgag cagaggacac ggcggtgtac tattgtgctc gcactgtccc aggttatagc   1080
actgcaccct acttcgatct gtggggacaa gggaccctgg tgactgtttc aagttaa     1137
```

<210> SEQ ID NO 22
<211> LENGTH: 1074
<212> TYPE: DNA
<213> ORGANISM: Artificial
<220> FEATURE:
<223> OTHER INFORMATION: Heavy chain A26-645(gH5)

<400> SEQUENCE: 22

```
gaagttcagc tggtcgagtc tggaggcggg cttgtccagc ctggagggag cctgcgtctc     60
tcttgtgcag caagcggttt cacgttcacc aactacggta tccactggat tcgtcaggca    120
ccaggtaaag gtctggaatg ggtagcctct atctctccgt ctggtggtct gacgtactac    180
cgtgactctg tcaaaggtcg tttcaccatc tctcgtgatg acgcgaaaaa ctctccgtac    240
ctgcaaatga actctctgcg tgcagaagat accgcagtgt actactgcgc tactggtggt    300
gaaggtatct tcgactactg gggtcagggt accctggtaa ctgtctcgag cgcttctaca    360
aagggcccaa gcgttttccc actggctccg tcctctaaat ccacctctgg tggtacggct    420
gcactgggtt gcctggtgaa agactacttc ccagaaccag ttaccgtgtc ttggaactct    480
ggtgcactga cctctggtgt tcacaccttt ccagcagttc tccagtcttc tggtctgtac    540
tccctgtcta gcgtggttac cgttccgtct tcttctctgg gtactcagac ctacatctgc    600
aacgtcaacc acaaaccgtc caacaccaag gtcgacaaaa agtcgagcc gaaatcctgt     660 agtggaggtg ggggctcagg tggaggcggg accggtggag gtggcagcga ggttcaactg    720
cttgagtctg gaggaggcct agtccagcct ggagggagcc tgcgtctctc ttgtgcagta    780
agcggcatcg acctgagcaa ttacgccatc aactgggtga gacaagctcc ggggaagtgt    840
ttagaatgga tcggtataat atgggccagt gggacgacct tttatgctac atgggcgaaa    900 ggaaggtttta caattagccg ggacaatagc aaaaacaccg tgtatctcca aatgaactcc    960
ttgcgagcag aggacacggc ggtgtactat tgtgctcgca ctgtcccagg ttatagcact   1020
```

```
gcaccctact tcgatctgtg gggacaaggg accctggtga ctgtttcaag ttaa         1074
```

<210> SEQ ID NO 23
<211> LENGTH: 1089
<212> TYPE: DNA
<213> ORGANISM: Artificial
<220> FEATURE:
<223> OTHER INFORMATION: Light chain A26-645(gL4) including E.coli OmpA
      leader

<400> SEQUENCE: 23

```
atgaaaaaga cagctatcgc aattgcagtg gcgttggctg gtttcgcgac cgttgcgcaa    60
gctgatatcc agatgaccca gagcccaagc agtctctccg ccagcgtagg cgatcgtgtg   120
actattacct gtcgtgcaac ccagagcatc tacaacgctc tggcttggta tcagcagaaa   180
ccgggtaaag cgccaaaact cctgatctac aacgcgaaca ctctgcatac tggtgttccg   240
tctcgtttct ctgcgtctgg ttctggtacg gactctactc tgaccatctc ctctctccag   300
ccggaagatt tcgcgaccta ctactgccag cagtactacg attacccact gacgtttggt   360
ggtggtacca agttgagat caaacgtacg gttgcagctc catccgtctt catctttcca    420
ccgtctgacg aacagctcaa atctggtact gcttctgtcg tttgcctcct gaacaacttc   480
tatccgcgtg aagcgaaagt ccagtggaaa gtcgacaacg cactccagtc tggtaactct   540
caggaatctg tgaccgaaca ggactccaaa gactccacct actctctgtc tagcaccctg   600
actctgtcca agcagacta cgagaaacac aaagtgtacg cttgcgaagt acccatcag    660
ggtctgagct ctccggttac caaatccttt aatagagggg agtgtggtgg cggtggcagt   720
ggtggtggag gttccggagg tggcggttca gacatacaaa tgacccagag tccttcatcg   780
gtatccgcgt ccgttggcga tagggtgact attacatgtc aaagctctcc tagcgtctgg   840
agcaattttc tatcctggta tcaacagaaa ccggggaagg ctccaaaact tctgatttat   900
gaagcctcga aactcaccag tggagttccg tcaagattca gtggctctgg atcagggaca   960
gacttcacgt tgacaatcag ttcgctgcaa ccagaggact ttgcgaccta ctattgtggt  1020
ggaggttaca gtagcataag tgatacgaca tttgggtgcg gtactaaggt ggaaatcaaa  1080
cgtacctaa                                                         1089
```

<210> SEQ ID NO 24
<211> LENGTH: 1026
<212> TYPE: DNA
<213> ORGANISM: Artificial
<220> FEATURE:
<223> OTHER INFORMATION: Light chain A26-645(gL4)

<400> SEQUENCE: 24

```
gatatccaga tgacccagag cccaagcagt ctctccgcca gcgtaggcga tcgtgtgact    60
attacctgtc gtgcaaccca gagcatctac aacgctctgg cttggtatca gcagaaaccg   120
ggtaaagcgc caaaactcct gatctacaac gcgaacactc tgcatactgg tgttccgtct   180
cgtttctctg cgtctggttc tggtacggac tctactctga ccatctcctc tctccagccg   240
gaagatttcg cgacctacta ctgccagcag tactacgatt acccactgac gtttggtggt   300
ggtaccaaag ttgagatcaa acgtacggtt gcagctccat ccgtcttcat ctttccaccg   360
tctgacgaac agctcaaatc tggtactgct tctgtcgttt gcctcctgaa caacttctat   420
ccgcgtgaag cgaaagtcca gtggaaagtc gacaacgcac tccagtctgg taactctcag   480
gaatctgtga ccgaacagga ctccaaagac tccacctact ctctgtctag caccctgact   540
```

-continued

```
ctgtccaaag cagactacga gaaacacaaa gtgtacgctt gcgaagttac ccatcagggt      600
ctgagctctc cggttaccaa atcctttaat agaggggagt gtggtggcgg tggcagtggt      660
ggtggaggtt ccggaggtgg cggttcagac atacaaatga cccagagtcc ttcatcggta      720
tccgcgtccg ttggcgatag ggtgactatt acatgtcaaa gctctcctag cgtctggagc      780
aattttctat cctggtatca acagaaaccg ggaaggctc caaaacttct gatttatgaa       840
gcctcgaaac tcaccagtgg agttccgtca agattcagtg ctctggatc agggacagac       900 ttcacgttga caatcagttc gctgcaacca gaggactttg cgacctacta ttgtggtgga      960
ggttacagta gcataagtga tacgacattt gggtgcggta ctaaggtgga aatcaaacgt     1020
acctaa                                                                1026

<210> SEQ ID NO 25
<211> LENGTH: 1131
<212> TYPE: DNA
<213> ORGANISM: Artificial
<220> FEATURE:
<223> OTHER INFORMATION: Heavy chain A26-645(gH5) including B72.3 leader
      sequence

<400> SEQUENCE: 25
atggaatggt cctgggtctt cctgtttttc ctttctgtca aaccggggt gcacagcgag        60 gtgcagctcg tcgagtctgg aggcgggctt gtccagcctg agggagcct gcgtctctct      120 tgtgcagcaa gcggtttcac gttcaccaac tacggtatcc actggattcg tcaggcacca     180
ggtaaaggtc tggaatgggt agcctctatc tctccgtctg gtggtctgac gtactaccgt     240
gactctgtca aggtcgtttt caccatctct cgtgatgacg cgaaaaactc tccgtacctg     300
cagatgaact ctctgcgtgc agaagatacc gcagtgtact actgcgctac tggtggtgaa     360
ggtatcttcg actactgggg tcagggtacc ctggtaactg tctcaagcgc ttctacaaag     420
ggcccatcgg tcttccccct ggcaccctcc tccaagagca cctctggggg cacagcggcc     480
ctgggctgcc tggtcaagga ctacttcccc gaaccggtga cggtgtcgtg aactcaggc     540 gccctgacca gcggcgtgca caccttcccg gctgtcctac agtcctctgg actctactcc     600
ctcagcagcg tggtgaccgt gccctccagc agcttgggca cccagaccta catctgcaac     660
gtgaatcaca agcccagcaa caccaaggtg gacaagaaag ttgagcccaa atcttgttcc     720
ggaggtggcg gttccggagg tggcggtacc ggtggcggtg gatccgaagt ccagctgctt     780
gaatccggag gcggactcgt gcagcccgga ggcagtcttc gcttgtcctg cgctgtatct     840
ggaatcgacc tgagcaatta cgccatcaac tgggtgagac aggcacctgg gaaatgcctc     900
gaatggatcg gcattatatg ggctagtggg acgacctttt atgctacatg ggcgaagggt     960
agattcacaa tctcacggga taatagtaag aacacagtgt acctgcagat gaactccctg    1020
cgagcagagg ataccgccgt ttactattgt gctcgcactg tcccaggtta tagcactgca    1080
ccctactttg atctgtgggg gcagggcact ctggtcaccg tctcgagttg a             1131

<210> SEQ ID NO 26
<211> LENGTH: 1074
<212> TYPE: DNA
<213> ORGANISM: Artificial
<220> FEATURE:
<223> OTHER INFORMATION: Heavy chain A26-645(gH5)

<400> SEQUENCE: 26
gaggtgcagc tcgtcgagtc tggaggcggg cttgtccagc ctggagggag cctgcgtctc       60
```
tcttgtgcag caagcggttt cacgttcacc aactacggta tccactggat cgtcaggca      120 ccaggtaaag gtctggaatg ggtagcctct atctctccgt ctggtggtct gacgtactac      180
cgtgactctg tcaaaggtcg tttcaccatc tctcgtgatg acgcgaaaaa ctctccgtac      240
ctgcagatga actctctgcg tgcagaagat accgcagtgt actactgcgc tactggtggt      300
gaaggtatct tcgactactg gggtcagggt accctggtaa ctgtctcaag cgcttctaca      360
aagggcccat cggtcttccc cctggcaccc tcctccaaga gcacctctgg ggcacagcg       420 gccctgggct gcctggtcaa ggactacttc cccgaaccgg tgacggtgtc gtggaactca      480
ggcgccctga ccagcggcgt gcacaccttc ccggctgtcc tacagtcctc tggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt      660 tccggaggtg gcggttccgg aggtggcggt accggtggcg gtggatccga agtccagctg      720
cttgaatccg gaggcggact cgtgcagccc ggaggcagtc ttcgcttgtc ctgcgctgta      780
tctggaatcg acctgagcaa ttacgccatc aactgggtga cacaggcacc tgggaaatgc      840
ctcgaatgga tcggcattat atgggctagt gggacgacct tttatgctac atgggcgaag      900
ggtagattca caatctcacg ggataatagt aagaacacag tgtacctgca gatgaactcc      960
ctgcgagcag aggataccgc cgtttactat tgtgctcgca ctgtcccagg ttatagcact     1020
gcaccctact tgatctgtgt gggcaggggc actctggtca ccgtctcgag ttga           1074

<210> SEQ ID NO 27
<211> LENGTH: 1086
<212> TYPE: DNA
<213> ORGANISM: Artificial
<220> FEATURE:
<223> OTHER INFORMATION: Light chain A26-645(gL4) including B72.3 leader
      sequence

<400> SEQUENCE: 27
atgtcagttc ccacacaggt gctgggcctg cttctgttgt ggctcaccga tgctaggtgt       60
gatatccaga tgacccagag tccaagcagt ctctccgcca cgtaggcga tcgtgtgact       120 attacctgtc gtgcaaccca gagcatctac aacgctctgg cttggtatca gcagaaaccg      180
ggtaaagcgc caaaactcct gatctacaac gcgaacactc tgcataccgg tgttccgtct      240
cgtttctctg cgtctggttc tggtacggac tctactctga ccatctcctc tctgcagccg      300
gaagatttcg cgacctacta ctgccagcag tactacgatt acccactgac gtttggtggt      360
ggtaccaaag ttgagatcaa acgtacggtg gctgcaccat ctgtcttcat cttccccca      420 tctgatgagc agttgaagtc tggcactgcc tctgttgtgt gcctgctgaa taacttctac      480
cctagagagg ccaaagtcca gtggaaggtg gataacgccc ttcaatccgg aaactcccag      540
gagagtgtca ctgagcagga ctcaaaggac tccacctata gccttagcag cacactgaca      600
ctgagcaagg ctgactacga aaacacaag gtctacgcct cgaagtgac acatcaaggc       660 ctgagctcac ccgtgacaaa gagctttaac aggggagagt gtggtggagg tggctctggc      720
ggtggtggct ccggaggcgg aggaagcgac atccagatga cccagagccc ttcctctgta      780
agcgccagtg tcggagacag agtgactatt acctgccaaa gctccccttc agtctggtcc      840 aatttctat cctggtacca gcaaaagccc ggaaaggctc ctaaattgct gatctacgaa       900
gcaagcaaac tcaccagcgg cgtgcccagc aggttcagcg cagtgggtc tggaactgac       960 tttaccctga caatctcctc actccagccc gaggacttcg ccacctatta ctgcggtgga     1020

```
ggttacagta gcataagtga tacgacattt ggatgcggca ctaaagtgga aatcaagcgt    1080
acctga                                                               1086
```

```
<210> SEQ ID NO 28
<211> LENGTH: 1026
<212> TYPE: DNA
<213> ORGANISM: Artificial
<220> FEATURE:
<223> OTHER INFORMATION: Light chain A26-645(gL4)

<400> SEQUENCE: 28
gatatccaga tgacccagag tccaagcagt ctctccgcca gcgtaggcga tcgtgtgact      60
attacctgtc gtgcaaccca gagcatctac aacgctctgg cttggtatca gcagaaaccg     120
ggtaaagcgc caaaactcct gatctacaac gcgaacactc tgcataccgg tgttccgtct     180
cgtttctctg cgtctggttc tggtacggac tctactctga ccatctcctc tctgcagccg     240
gaagatttcg cgacctacta ctgccagcag tactacgatt acccactgac gtttggtggt     300
ggtaccaaag ttgagatcaa acgtacggtg gctgcaccat ctgtcttcat cttcccccca     360
tctgatgagc agttgaagtc tggcactgcc tctgttgtgt gcctgctgaa taacttctac     420
cctagagagg ccaaagtcca gtggaaggtg gataacgccc ttcaatccgg aaactcccag     480
gagagtgtca ctgagcagga ctcaaaggac tccacctata gccttagcag cacactgaca     540
ctgagcaagg ctgactacga aaacacaag gtctacgcct gcgaagtgac acatcaaggc     600
ctgagctcac ccgtgacaaa gagctttaac aggggagagt gtggtggagg tggctctggc     660
ggtggtggct ccggaggcgg aggaagcgac atccagatga cccagagccc ttcctctgta     720
agcgccagtg tcggagacag agtgactatt acctgccaaa gctccccttc agtctggtcc     780
aattttctat cctggtacca gcaaaagccc ggaaaggctc ctaaattgct gatctacgaa     840
gcaagcaaac tcaccagcgg cgtgcccagc aggttcagcg cagtgggtc tggaactgac     900 tttaccctga caatctcctc actccagccc gaggacttcg ccacctatta ctgcggtgga     960
ggttacagta gcataagtga tacgacattt ggatgcggca ctaaagtgga aatcaagcgt    1020
acctga                                                               1026
```

```
<210> SEQ ID NO 29
<211> LENGTH: 121
<212> TYPE: PRT
<213> ORGANISM: Artificial
<220> FEATURE:
<223> OTHER INFORMATION: Heavy chain variable domain of anti-albumin
      antibody (no ds)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95
```

```
Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120
```

<210> SEQ ID NO 30
<211> LENGTH: 121
<212> TYPE: PRT
<213> ORGANISM: Artificial
<220> FEATURE:
<223> OTHER INFORMATION: Heavy chain variable domain of anti-albumin antibody (ds)

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120
```

<210> SEQ ID NO 31
<211> LENGTH: 112
<212> TYPE: PRT
<213> ORGANISM: Artificial
<220> FEATURE:
<223> OTHER INFORMATION: Light chain variable domain of anti-albumin antibody (no ds)

<400> SEQUENCE: 31

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys Arg Thr
            100                 105                 110
```

<210> SEQ ID NO 32
<211> LENGTH: 112
<212> TYPE: PRT
<213> ORGANISM: Artificial

<220> FEATURE:
<223> OTHER INFORMATION: Light chain variable domain of anti-albumin antibody (ds)

<400> SEQUENCE: 32

Asp Ile Gln Met Thr Gln Ser Pro Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
            85                  90                  95

Ser Asp Thr Thr Phe Gly Cys Gly Thr Lys Val Glu Ile Lys Arg Thr
            100                 105                 110

<210> SEQ ID NO 33
<211> LENGTH: 16
<212> TYPE: PRT
<213> ORGANISM: Artificial
<220> FEATURE:
<223> OTHER INFORMATION: Linker 1

<400> SEQUENCE: 33

Ser Gly Gly Gly Gly Ser Gly Gly Gly Gly Thr Gly Gly Gly Gly Ser
1               5                   10                  15

<210> SEQ ID NO 34
<211> LENGTH: 15
<212> TYPE: PRT
<213> ORGANISM: Artificial
<220> FEATURE:
<223> OTHER INFORMATION: Linker 2

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 789
<212> TYPE: DNA
<213> ORGANISM: Artificial
<220> FEATURE:
<223> OTHER INFORMATION: 645 gH5gL4

<400> SEQUENCE: 35
gaggttcagc tgctggagtc tggaggcggg cttgtccagc ctggagggag cctgcgtctc      60
tcttgtgcag taagcggcat cgacctgtcc aactacgcga ttaactgggt acgtcaggca     120
ccgggtaaag gtctggaatg gatcggcatc atctgggcct ctggtacgac cttctacgct    180
acttgggcca aggtcgtttt caccatctcc cgtgacaact ctaaaaacac cgtgtacctg    240
cagatgaact ctctgcgtgc ggaagacact gcggtttact attgcgcgcg taccgttccg    300
ggctattcta ctgcaccgta cttcgacctg tggggtcagg gtactctggt accgtctcg    360 agtggaggtg gcggttctgg cggtggcggt tccggtggcg gtggatcggg aggtggcggt    420
tctgatatcc agatgaccca gagtccaagc agtgtttccg ccagcgtagg cgatcgtgtg    480

```
actattacct gtcagtcctc tccgagcgtt tggtccaact tcctgagctg gtaccagcag    540
aaaccgggta agccccgaa actgctgatc tacgaggcgt ctaaactgac ctctggtgta    600
ccgtcccgtt tctctggctc tggctctggt acggacttca ctctgaccat ctcctctctg    660
cagccggaag actttgcaac gtactactgc ggtggtggtt actcttccat ctctgacacc    720
acgttcggtg gaggcaccaa agttgaaatc aaacgtacgc atcaccatca ccatcaccat    780
caccatcac                                                           789
```

<210> SEQ ID NO 36
<211> LENGTH: 263
<212> TYPE: PRT
<213> ORGANISM: Artificial
<220> FEATURE:
<223> OTHER INFORMATION: 645 gH5gL4

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Tyr Ser Ser Ile Ser Asp Thr
225                 230                 235                 240

Thr Phe Gly Gly Gly Thr Lys Val Glu Ile Lys Arg Thr His His His
                245                 250                 255

His His His His His
            260
```

<210> SEQ ID NO 37
<211> LENGTH: 789
<212> TYPE: DNA
<213> ORGANISM: Artificial
<220> FEATURE:

<223> OTHER INFORMATION: 645 gH5gL4ds

<400> SEQUENCE: 37

```
gaggttcagc tgctggagtc tggaggcggg cttgtccagc tggagggag cctgcgtctc    60
tcttgtgcag taagcggcat cgacctgtcc aactacgcga ttaactgggt acgtcaggca   120
ccgggtaaat gcctggaatg gatcggcatc atctgggcct ctggtacgac cttctacgct   180
acttgggcca aggtcgtttt caccatctcc cgtgacaact ctaaaaacac cgtgtacctg   240
cagatgaact ctctgcgtgc ggaagacact gcggtttact attgcgcgcg taccgttccg   300
ggctattcta ctgcaccgta cttcgacctg tggggtcagg gtactctggt taccgtctcg   360
agtggaggtg gcggttctgg cggtggcggt tccggtggcg gtggatcggg aggtggcggt   420
tctgatatcc agatgaccca gagtccaagc agtgtttccg ccagcgtagg cgatcgtgtg   480
actattacct gtcagtcctc tccgagcgtt tggtccaact tcctgagctg gtaccagcag   540
aaaccgggta agcccccgaa actgctgatc tacgaggcgt ctaaactgac ctctggtgta   600
ccgtcccgtt tctctggctc tggctctggt acggacttca ctctgaccat ctcctctctg   660
cagccggaag actttgcaac gtactactgc ggtggtggtt actcttccat ctctgacacc   720
acgttcggtt gtggcaccaa agttgaaatc aaacgtacgc atcaccatca ccatcaccat   780
caccatcac                                                          789
```

<210> SEQ ID NO 38
<211> LENGTH: 263
<212> TYPE: PRT
<213> ORGANISM: Artificial
<220> FEATURE:
<223> OTHER INFORMATION: 645 gH5gL4ds

<400> SEQUENCE: 38

```
Glu Val Gln Leu Leu Glu Ser Gly Gly Gly Leu Val Gln Pro Gly Gly
  1               5                  10                  15

Ser Leu Arg Leu Ser Cys Ala Val Ser Gly Ile Asp Leu Ser Asn Tyr
             20                  25                  30

Ala Ile Asn Trp Val Arg Gln Ala Pro Gly Lys Cys Leu Glu Trp Ile
         35                  40                  45

Gly Ile Ile Trp Ala Ser Gly Thr Thr Phe Tyr Ala Thr Trp Ala Lys
     50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Gly Gly Gly Ser Gly Gly Gly Gly
        115                 120                 125

Gly Gly Ser Gly Gly Gly Gly Ser Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
```

```
              195                 200                 205
Ser Gly Thr Asp Phe Thr Leu Thr Ile Ser Ser Leu Gln Pro Glu Asp
    210                 215                 220

Phe Ala Thr Tyr Tyr Cys Gly Gly Tyr Ser Ser Ile Ser Asp Thr
225                 230                 235                 240

Thr Phe Gly Cys Gly Thr Lys Val Glu Ile Lys Arg Thr His His His
                245                 250                 255

His His His His His His His
            260

<210> SEQ ID NO 39
<211> LENGTH: 8
<212> TYPE: PRT
<213> ORGANISM: Artificial
<220> FEATURE:
<223> OTHER INFORMATION: Hinge Linker

<400> SEQUENCE: 39

Asp Lys Thr His Thr Cys Ala Ala
1               5

<210> SEQ ID NO 40
<211> LENGTH: 11
<212> TYPE: PRT
<213> ORGANISM: Artificial
<220> FEATURE:
<223> OTHER INFORMATION: Hinge Linker

<400> SEQUENCE: 40

Asp Lys Thr His Thr Cys Pro Pro Cys Pro Ala
1               5                   10

<210> SEQ ID NO 41
<211> LENGTH: 18
<212> TYPE: PRT
<213> ORGANISM: Artificial
<220> FEATURE:
<223> OTHER INFORMATION: Hinge Linker

<400> SEQUENCE: 41

Asp Lys Thr His Thr Cys Pro Pro Cys Pro Ala Thr Cys Pro Pro Cys
1               5                   10                  15

Pro Ala

<210> SEQ ID NO 42
<211> LENGTH: 25
<212> TYPE: PRT
<213> ORGANISM: Artificial
<220> FEATURE:
<223> OTHER INFORMATION: Hinge Linker

<400> SEQUENCE: 42

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 43
<211> LENGTH: 30
<212> TYPE: PRT
<213> ORGANISM: Artificial
<220> FEATURE:
<223> OTHER INFORMATION: Hinge Linker
```

```
<400> SEQUENCE: 43

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 44
<211> LENGTH: 31
<212> TYPE: PRT
<213> ORGANISM: Artificial
<220> FEATURE:
<223> OTHER INFORMATION: Hinge Linker

<400> SEQUENCE: 44

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 45
<211> LENGTH: 15
<212> TYPE: PRT
<213> ORGANISM: Artificial
<220> FEATURE:
<223> OTHER INFORMATION: Hinge Linker

<400> SEQUENCE: 45

Asp Lys Thr His Thr Cys Cys Val Glu Cys Pro Pro Cys Pro Ala
1               5                   10                  15

<210> SEQ ID NO 46
<211> LENGTH: 26
<212> TYPE: PRT
<213> ORGANISM: Artificial
<220> FEATURE:
<223> OTHER INFORMATION: Hinge Linker

<400> SEQUENCE: 46

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 47
<211> LENGTH: 11
<212> TYPE: PRT
<213> ORGANISM: Artificial
<220> FEATURE:
<223> OTHER INFORMATION: Hinge Linker

<400> SEQUENCE: 47

Asp Lys Thr His Thr Cys Pro Ser Cys Pro Ala
1               5                   10

<210> SEQ ID NO 48
<211> LENGTH: 7
<212> TYPE: PRT
<213> ORGANISM: Artificial
<220> FEATURE:
<223> OTHER INFORMATION: Linker

<400> SEQUENCE: 48

Ser Gly Gly Gly Gly Ser Glu
1               5
```

```
<210> SEQ ID NO 49
<211> LENGTH: 6
<212> TYPE: PRT
<213> ORGANISM: Artificial
<220> FEATURE:
<223> OTHER INFORMATION: Linker

<400> SEQUENCE: 49

Asp Lys Thr His Thr Ser
1               5

<210> SEQ ID NO 50
<211> LENGTH: 6
<212> TYPE: PRT
<213> ORGANISM: Artificial
<220> FEATURE:
<223> OTHER INFORMATION: Linker

<400> SEQUENCE: 50

Ser Gly Gly Gly Gly Ser
1               5

<210> SEQ ID NO 51
<211> LENGTH: 11
<212> TYPE: PRT
<213> ORGANISM: Artificial
<220> FEATURE:
<223> OTHER INFORMATION: Linker

<400> SEQUENCE: 51

Ser Gly Gly Gly Gly Ser Gly Gly Gly Gly Ser
1               5                   10

<210> SEQ ID NO 52
<211> LENGTH: 16
<212> TYPE: PRT
<213> ORGANISM: Artificial
<220> FEATURE:
<223> OTHER INFORMATION: Linker

<400> SEQUENCE: 52

Ser Gly Gly Gly Gly Ser Gly Gly Gly Gly Ser Gly Gly Gly Gly Ser
1               5                   10                  15

<210> SEQ ID NO 53
<211> LENGTH: 21
<212> TYPE: PRT
<213> ORGANISM: Artificial
<220> FEATURE:
<223> OTHER INFORMATION: Linker

<400> SEQUENCE: 53

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 54
<211> LENGTH: 26
<212> TYPE: PRT
<213> ORGANISM: Artificial
<220> FEATURE:
<223> OTHER INFORMATION: Linker

<400> SEQUENCE: 54

Ser Gly Gly Gly Gly Ser Gly Gly Gly Gly Ser Gly Gly Gly Gly Ser
```

```
                1               5                  10                 15
Gly Gly Gly Gly Ser Gly Gly Gly Gly Ser
            20                  25

<210> SEQ ID NO 55
<211> LENGTH: 11
<212> TYPE: PRT
<213> ORGANISM: Artificial
<220> FEATURE:
<223> OTHER INFORMATION: Linker

<400> SEQUENCE: 55

Ala Ala Ala Gly Ser Gly Gly Ala Ser Ala Ser
1               5                   10

<210> SEQ ID NO 56
<211> LENGTH: 16
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 56

Ala Ala Ala Gly Ser Gly Xaa Gly Gly Gly Ser Gly Ala Ser Ala Ser
1               5                   10                  15

<210> SEQ ID NO 57
<211> LENGTH: 21
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 57

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 58
<211> LENGTH: 26
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
```

```
<400> SEQUENCE: 58

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 59
<211> LENGTH: 31
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 59

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 60
<211> LENGTH: 13
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 60

Ala Ala Ala Gly Ser Gly Xaa Ser Gly Ala Ser Ala Ser
1               5                   10

<210> SEQ ID NO 61
<211> LENGTH: 28
<212> TYPE: PRT
<213> ORGANISM: Artificial
<220> FEATURE:
<223> OTHER INFORMATION: Linker

<400> SEQUENCE: 61

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 62
<211> LENGTH: 11
<212> TYPE: PRT
<213> ORGANISM: Artificial
<220> FEATURE:
```

<223> OTHER INFORMATION: Linker

<400> SEQUENCE: 62

Ala Thr Thr Thr Gly Ser Ser Pro Gly Pro Thr
1               5                   10

<210> SEQ ID NO 63
<211> LENGTH: 6
<212> TYPE: PRT
<213> ORGANISM: Artificial
<220> FEATURE:
<223> OTHER INFORMATION: Linker

<400> SEQUENCE: 63

Ala Thr Thr Thr Gly Ser
1               5

<210> SEQ ID NO 64
<211> LENGTH: 21
<212> TYPE: PRT
<213> ORGANISM: Artificial
<220> FEATURE:
<223> OTHER INFORMATION: Linker

<400> SEQUENCE: 64

Glu Pro Ser Gly Pro Ile Ser Thr Ile Asn Ser Pro Pro Ser Lys Glu
1               5                   10                  15

Ser His Lys Ser Pro
            20

<210> SEQ ID NO 65
<211> LENGTH: 15
<212> TYPE: PRT
<213> ORGANISM: Artificial
<220> FEATURE:
<223> OTHER INFORMATION: Linker

<400> SEQUENCE: 65

Gly Thr Val Ala Ala Pro Ser Val Phe Ile Phe Pro Pro Ser Asp
1               5                   10                  15

<210> SEQ ID NO 66
<211> LENGTH: 15
<212> TYPE: PRT
<213> ORGANISM: Artificial
<220> FEATURE:
<223> OTHER INFORMATION: Linker

<400> SEQUENCE: 66

Gly Gly Gly Gly Ile Ala Pro Ser Met Val Gly Gly Gly Gly Ser
1               5                   10                  15

<210> SEQ ID NO 67
<211> LENGTH: 15
<212> TYPE: PRT
<213> ORGANISM: Artificial
<220> FEATURE:
<223> OTHER INFORMATION: Linker

<400> SEQUENCE: 67

Gly Gly Gly Gly Lys Val Glu Gly Ala Gly Gly Gly Gly Gly Ser
1               5                   10                  15

<210> SEQ ID NO 68
<211> LENGTH: 15
<212> TYPE: PRT

<213> ORGANISM: Artificial
<220> FEATURE:
<223> OTHER INFORMATION: Linker

<400> SEQUENCE: 68

Gly Gly Gly Gly Ser Met Lys Ser His Asp Gly Gly Gly Gly Ser
1               5                   10                  15

<210> SEQ ID NO 69
<211> LENGTH: 15
<212> TYPE: PRT
<213> ORGANISM: Artificial
<220> FEATURE:
<223> OTHER INFORMATION: Linker

<400> SEQUENCE: 69

Gly Gly Gly Gly Asn Leu Ile Thr Ile Val Gly Gly Gly Gly Ser
1               5                   10                  15

<210> SEQ ID NO 70
<211> LENGTH: 15
<212> TYPE: PRT
<213> ORGANISM: Artificial
<220> FEATURE:
<223> OTHER INFORMATION: Linker

<400> SEQUENCE: 70

Gly Gly Gly Gly Val Val Pro Ser Leu Pro Gly Gly Gly Gly Ser
1               5                   10                  15

<210> SEQ ID NO 71
<211> LENGTH: 12
<212> TYPE: PRT
<213> ORGANISM: Artificial
<220> FEATURE:
<223> OTHER INFORMATION: Linker

<400> SEQUENCE: 71

Gly Gly Glu Lys Ser Ile Pro Gly Gly Gly Gly Ser
1               5                   10

<210> SEQ ID NO 72
<211> LENGTH: 18
<212> TYPE: PRT
<213> ORGANISM: Artificial
<220> FEATURE:
<223> OTHER INFORMATION: Linker

<400> SEQUENCE: 72

Arg Pro Leu Ser Tyr Arg Pro Pro Phe Pro Phe Gly Phe Pro Ser Val
1               5                   10                  15

Arg Pro

<210> SEQ ID NO 73
<211> LENGTH: 18
<212> TYPE: PRT
<213> ORGANISM: Artificial
<220> FEATURE:
<223> OTHER INFORMATION: Linker

<400> SEQUENCE: 73

Tyr Pro Arg Ser Ile Tyr Ile Arg Arg Arg His Pro Ser Pro Ser Leu
1               5                   10                  15

Thr Thr

-continued

```
<210> SEQ ID NO 74
<211> LENGTH: 18
<212> TYPE: PRT
<213> ORGANISM: Artificial
<220> FEATURE:
<223> OTHER INFORMATION: Linker

<400> SEQUENCE: 74

Thr Pro Ser His Leu Ser His Ile Leu Pro Ser Phe Gly Leu Pro Thr
1               5                   10                  15

Phe Asn

<210> SEQ ID NO 75
<211> LENGTH: 18
<212> TYPE: PRT
<213> ORGANISM: Artificial
<220> FEATURE:
<223> OTHER INFORMATION: Linker

<400> SEQUENCE: 75

Arg Pro Val Ser Pro Phe Thr Phe Pro Arg Leu Ser Asn Ser Trp Leu
1               5                   10                  15

Pro Ala

<210> SEQ ID NO 76
<211> LENGTH: 18
<212> TYPE: PRT
<213> ORGANISM: Artificial
<220> FEATURE:
<223> OTHER INFORMATION: Linker

<400> SEQUENCE: 76

Ser Pro Ala Ala His Phe Pro Arg Ser Ile Pro Arg Pro Gly Pro Ile
1               5                   10                  15

Arg Thr

<210> SEQ ID NO 77
<211> LENGTH: 18
<212> TYPE: PRT
<213> ORGANISM: Artificial
<220> FEATURE:
<223> OTHER INFORMATION: Linker

<400> SEQUENCE: 77

Ala Pro Gly Pro Ser Ala Pro Ser His Arg Ser Leu Pro Ser Arg Ala
1               5                   10                  15

Phe Gly

<210> SEQ ID NO 78
<211> LENGTH: 18
<212> TYPE: PRT
<213> ORGANISM: Artificial
<220> FEATURE:
<223> OTHER INFORMATION: Linker

<400> SEQUENCE: 78

Pro Arg Asn Ser Ile His Phe Leu His Pro Leu Leu Val Ala Pro Leu
1               5                   10                  15

Gly Ala

<210> SEQ ID NO 79
<211> LENGTH: 18
<212> TYPE: PRT
<213> ORGANISM: Artificial
```

<220> FEATURE:
<223> OTHER INFORMATION: Linker

<400> SEQUENCE: 79

Met Pro Ser Leu Ser Gly Val Leu Gln Val Arg Tyr Leu Ser Pro Pro
1               5                   10                  15

Asp Leu

<210> SEQ ID NO 80
<211> LENGTH: 18
<212> TYPE: PRT
<213> ORGANISM: Artificial
<220> FEATURE:
<223> OTHER INFORMATION: Linker

<400> SEQUENCE: 80

Ser Pro Gln Tyr Pro Ser Pro Leu Thr Leu Thr Leu Pro Pro His Pro
1               5                   10                  15

Ser Leu

<210> SEQ ID NO 81
<211> LENGTH: 18
<212> TYPE: PRT
<213> ORGANISM: Artificial
<220> FEATURE:
<223> OTHER INFORMATION: Linker

<400> SEQUENCE: 81

Asn Pro Ser Leu Asn Pro Pro Ser Tyr Leu His Arg Ala Pro Ser Arg
1               5                   10                  15

Ile Ser

<210> SEQ ID NO 82
<211> LENGTH: 17
<212> TYPE: PRT
<213> ORGANISM: Artificial
<220> FEATURE:
<223> OTHER INFORMATION: Linker

<400> SEQUENCE: 82

Leu Pro Trp Arg Thr Ser Leu Leu Pro Ser Leu Pro Leu Arg Arg Arg
1               5                   10                  15

Pro

<210> SEQ ID NO 83
<211> LENGTH: 18
<212> TYPE: PRT
<213> ORGANISM: Artificial
<220> FEATURE:
<223> OTHER INFORMATION: Linker

<400> SEQUENCE: 83

Pro Pro Leu Phe Ala Lys Gly Pro Val Gly Leu Leu Ser Arg Ser Phe
1               5                   10                  15

Pro Pro

<210> SEQ ID NO 84
<211> LENGTH: 18
<212> TYPE: PRT
<213> ORGANISM: Artificial
<220> FEATURE:
<223> OTHER INFORMATION: Linker

<400> SEQUENCE: 84

```
Val Pro Pro Ala Pro Val Val Ser Leu Arg Ser Ala His Ala Arg Pro
1               5                   10                  15

Pro Tyr

<210> SEQ ID NO 85
<211> LENGTH: 17
<212> TYPE: PRT
<213> ORGANISM: Artificial
<220> FEATURE:
<223> OTHER INFORMATION: Linker

<400> SEQUENCE: 85

Leu Arg Pro Thr Pro Pro Arg Val Arg Ser Tyr Thr Cys Cys Pro Thr
1               5                   10                  15

Pro

<210> SEQ ID NO 86
<211> LENGTH: 18
<212> TYPE: PRT
<213> ORGANISM: Artificial
<220> FEATURE:
<223> OTHER INFORMATION: Linker

<400> SEQUENCE: 86

Pro Asn Val Ala His Val Leu Pro Leu Leu Thr Val Pro Trp Asp Asn
1               5                   10                  15

Leu Arg

<210> SEQ ID NO 87
<211> LENGTH: 18
<212> TYPE: PRT
<213> ORGANISM: Artificial
<220> FEATURE:
<223> OTHER INFORMATION: Linker

<400> SEQUENCE: 87

Cys Asn Pro Leu Leu Pro Leu Cys Ala Arg Ser Pro Ala Val Arg Thr
1               5                   10                  15

Phe Pro

<210> SEQ ID NO 88
<211> LENGTH: 15
<212> TYPE: PRT
<213> ORGANISM: Artificial
<220> FEATURE:
<223> OTHER INFORMATION: Linker

<400> SEQUENCE: 88

Gly Gly Gly Gly Ser Gly Gly Gly Thr Gly Gly Gly Gly Ser
1               5                   10                  15

<210> SEQ ID NO 89
<211> LENGTH: 11
<212> TYPE: PRT
<213> ORGANISM: Artificial
<220> FEATURE:
<223> OTHER INFORMATION: linker

<400> SEQUENCE: 89

Gly Ala Pro Ala Pro Ala Ala Pro Ala Pro Ala
1               5                   10

<210> SEQ ID NO 90
```

```
<211> LENGTH: 4
<212> TYPE: PRT
<213> ORGANISM: Artificial
<220> FEATURE:
<223> OTHER INFORMATION: linker

<400> SEQUENCE: 90

Pro Pro Pro Pro
1
```